US010552969B2

(12) United States Patent
Simpson et al.

(10) Patent No.: US 10,552,969 B2
(45) Date of Patent: Feb. 4, 2020

(54) SYSTEM, METHOD AND COMPUTER-ACCESSIBLE MEDIUM FOR TEXTURE ANALYSIS OF HEPATOPANCREATOBILIARY DISEASES

(71) Applicant: MEMORIAL SLOAN-KETTERING CANCER CENTER, New York, NY (US)

(72) Inventors: Amber Lea Simpson, New York, NY (US); Richard Kinh Gian Do, New York, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 0 days.

(21) Appl. No.: 15/577,101

(22) PCT Filed: May 26, 2016

(86) PCT No.: PCT/US2016/034356
§ 371 (c)(1),
(2) Date: Nov. 27, 2017

(87) PCT Pub. No.: WO2016/191567
PCT Pub. Date: Dec. 1, 2016

(65) Prior Publication Data
US 2019/0019300 A1    Jan. 17, 2019

Related U.S. Application Data

(60) Provisional application No. 62/166,433, filed on May 26, 2015.

(51) Int. Cl.
*G06K 9/00* (2006.01)
*G06T 7/45* (2017.01)
(Continued)

(52) U.S. Cl.
CPC .............. *G06T 7/45* (2017.01); *A61B 6/032* (2013.01); *A61B 6/50* (2013.01); *A61B 6/5217* (2013.01);
(Continued)

(58) Field of Classification Search
CPC ............................................ G06T 2207/10081
See application file for complete search history.

(56) References Cited

U.S. PATENT DOCUMENTS

2005/0180621 A1    8/2005  Raman et al.
2008/0031506 A1    2/2008  Agatheeswaran et al.
(Continued)

OTHER PUBLICATIONS

International Search Report for International Application No. PCT/US2016/034356 dated Oct. 30, 2016.
(Continued)

*Primary Examiner* — Oneal R Mistry
(74) *Attorney, Agent, or Firm* — Hunton Andrews Kurth LLP

(57) ABSTRACT

An exemplary system, method and computer-accessible medium for determining the pixel variation of a tissue(s) in an image(s) can be provided, which can include, for example, receiving first imaging information related to the image(s), segmenting a region(s) of interest from the image(s), generating second imaging information by subtracting a structure(s) from the region(s) of interest, and determining the pixel variation based on the second imaging information. The tissue(s) can include a liver and/or a pancreas. A treatment characteristic(s) can be determined based on the pixel variation, which can include (i) a sufficiency of the tissue(s), (ii) a response to chemotherapy by the tissue(s), (iii) a recurrence of cancer in the tissue(s), or (iv) a measure of a genomic expression of the tissue(s).

26 Claims, 57 Drawing Sheets

(51) Int. Cl.
| | |
|---|---|
| *G06T 7/11* | (2017.01) |
| *G06K 9/46* | (2006.01) |
| *G06T 7/00* | (2017.01) |
| *G06T 7/155* | (2017.01) |
| *G06T 7/40* | (2017.01) |
| *G06T 7/194* | (2017.01) |
| *G16H 30/20* | (2018.01) |
| *A61B 6/03* | (2006.01) |
| *A61B 6/00* | (2006.01) |

(52) U.S. Cl.
CPC .............. *A61B 6/54* (2013.01); *G06K 9/46* (2013.01); *G06T 7/0012* (2013.01); *G06T 7/0014* (2013.01); *G06T 7/11* (2017.01); *G06T 7/155* (2017.01); *G06T 7/194* (2017.01); *G06T 7/40* (2013.01); *G16H 30/20* (2018.01); *G06T 2207/10072* (2013.01); *G06T 2207/10081* (2013.01); *G06T 2207/20224* (2013.01); *G06T 2207/30004* (2013.01); *G06T 2207/30056* (2013.01); *G06T 2207/30096* (2013.01)

(56) References Cited

U.S. PATENT DOCUMENTS

| | | | |
|---|---|---|---|
| 2008/0119718 | A1 | 5/2008 | Hundley et al. |
| 2013/0317352 | A1* | 11/2013 | Case .................. A61B 8/0841 600/424 |
| 2013/0329973 | A1* | 12/2013 | Cao .................... A61B 5/0033 382/128 |
| 2017/0091574 | A1* | 3/2017 | Udupa .................... G06T 7/11 |
| 2017/0236283 | A1* | 8/2017 | Lambin ................ G06T 7/0016 382/131 |

OTHER PUBLICATIONS

International Written Opinion for International Application No. PCT/US2016/034356 dated Oct. 30, 2016.
Gomez-Romero, Manuel et al., "Optical Analysis of Computed Tomography Images of the Liver Predicts Fibrosis Stage and Distribution in Chronic Hepatitis C," Hepatology, vol. 47, pp. 810-816, 2008.
Ganeshan, Balaji et al., "Dynamic Contrast-Enhanced Texture Analysis of the Liver: Initial Assessment in Colorectal Cancer," Investigative Radiol, vol. 46, pp. 160-168, 2011.
Miles, Kenneth A. et al., "Colorectal Cancer: Texture Analysis of Portal Phase Hepatic CT Images as a Potential Marker of Survival," Radiology, vol. 250, pp. 444-452, 2009.
Davnall, Fergus et al., "Assessment of Tumor Heterogeneity: An Emerging Imaging Tool for Clinical Practice?," Insights into Imaging, vol. 3, pp. 573-589, 2012.
Mascaux, Celine et al., "EGFR Protein Expression in Non-small Cell Lung Cancer Predicts Response to an EGFR Tyrosine Kinase Inhibitor-A Novel Antibody for Immunohistochemistry or AQUA Technology," Clin Cancer Res., vol. 17, pp. 7796-7807, 2011.
Tortara, Giampaolo et al., "Combined Targeting of EGFR-Dependent and VEGF-Dependent Pathways: Rationale Preclinical Studies and Clinical Applications," Nature Clinical Practice Oncology, vol. 5, pp. 521-530, 2008.
Agrawal, Shefali et al., "CD24 Expression is an Independent Prognostic Marker in Cholangiocarcinoma," Journal Gastrointest Surg., vol. 11, pp. 445-451, 2007.
Keeratichamroen, Siriporn et al., "Expression of CD24 in Cholangiocarcinoma Cells is Associated with Disease Progression and Reduced Patient Survival," International Journal of Oncology, vol. 39, pp. 873-881, 2011.
Davenport, Matthew S. et al., "Repeatability of Diagnostic Features and Scoring Systems for Hepatocellular Carcinoma by using MR Imaging," Radiology, vol. 272, pp. 132-142, 2014.
Gatenby, Robert A. et al., "Quantitative Imaging in Cancer Evolution and Ecology," Radiology, vol. 269, No. 1, pp. 8-15, 2013.
Segal, E. et al., "Decoding Global Gene Expression Programs in Liver Cancer by Noninvasive Imaging," Nature Biotechnology, vol. 25, pp. 675-680, 2007.
Diehn, Maximillian et al., "Identification of Noninvasive Imaging Surrogates for Brain Tumor Gene-Expression Modules," Proc Natl Acad Sci USA, vol. 105, 5213-5218, 2008.
Cuzick, Jack et al., "Prognostic Value of a Combined Estrogen Receptor, Progesterone Receptor, Ki-67, and Human Epidermal Growth Factor Receptor 2 Immunohistochemical Score and Comparison with the Genomic Health Recurrence Score in Early Breast Cancer," Journal of Clinical Oncology: Official Journal of the American Society of Clinical Oncology, vol. 29, pp. 4273-4278, 2011.
Yoshikawa, D. et al., "Clinicopathological and Prognostic Significance of EGFR, VEGF, and HER2 Expression in Cholangiocarcinoma," British Journal of Cancer, vol. 98, pp. 418-425, 2008
Thelen, Armin et al., "Tumor-Associated Angiogenesis and Lymphangiogenesis Correlate with Progression of Intrahepatic Cholangiocarcinoma," Am Journal Gastroenterol, vol. 105, pp. 1123-1132, 2010.
Jarnagin, W.R. et al., "Regional Chemotherapy for Unresectable Primary Liver Cancer: Results of a Phase II Clinical Trial and Assessment of DCE-MRI as a Biomarker of Survival," Annals of Oncology: Official Journal of the European Society for Medical Oncology/ESMO, vol. 20, pp. 1589-1595, 2009.
Kemeny, Nancy E. et al., "Treating Primary Liver Cancer with Hepatic Arterial Infusion of Floxuridine and Dexamethasone: Does the Addition of Systemic Bevacizumab Improve Results?," Oncology, vol. 80, p. 153-159, 2011.
Simpson, Amber L. et al., "Liver Planning Software Accurately Predicts Postoperative Liver Volume and Measures Early Regeneration," Journal Am Coll Surg. vol. 219, pp. 199-207, 2014.
Marotta, Lauren L.C. et al., "The JAK2/STAT3 Signaling Pathway is Required for Growth of CD44(+)CD24(-31 ) Stem Cell-Like Breast Cancer Cells in Human Tumors," Journal Clin Invest, vol. 121, pp. 2723-2735, 2011.
Shia, J. et al., "Epidermal Growth Factor Receptor Expression and Gene Amplification in Colorectal Carcinoma: An Immunohistochemical and Chromogenic in Situ Hybridization Study," Modern Pathology: An Official Journal of the United States and Canadian Academy of Pathology, Inc., vol. 18, pp. 1350-1356, 2005.
Yopp, Adam C. et al., "Antiangiogenic Therapy for Primary Liver Cancer: Correlation of Changes in Dynamic Contrast-Enhanced Magnetic Resonance Imaging with Tissue Hypoxia Markers and Clinical Response," Ann Surg Oncol, vol. 18, pp. 2192-2199, 2011.
Zhou, Sheng et al., "MDM2 Regulates Vascular Endothelial Growth Factor mRNA Stabilization in Hypoxia," Mol Cell Biol, vol. 31, pp. 4928-4937, 2011.
Lee, J.H. et al., "Hypoxia Activates Tumor Suppressor p53 by Inducing ATR-Chk1 Kinase Cascade-Mediated Phosphorylation and Consequent 14-3-3Gamma Inactivation of MDMX Protein," Journal Biol Chem. vol. 287, pp. 20898-20903, 2012.
Cleven, Arjen H.G. et al., "Stromal Expression of Hypoxia Regulated Proteins is an Adverse Prognostic Factor in Colorectal Carcinomas," Cellular Oncology: The Official Journal of the International Society for Cellular Oncology, vol. 29, pp. 229-240, 2007.
Thomas, Shibu et al., "CD24 is an Effector of HIF-1-Driven Primary Tumor Growth and Metastasis," Cancer Res., vol. 72, pp. 5600-5612, 2012.
Parez-Sayans, Mario et al., "The Role of Carbonic Anhydrase IX in Hypoxia Control in OSCC," Journal of Oral Pathology & Medicine: Official Publication of the International Association of Oral Pathologists and the American Academy of Oral Pathology, vol. 42, pp. 1-8, 2013.
Ding, Zhenyu et al., "Expression and Significance of Hypoxia-Inducible Factor-1 Alpha and MDR1/P-Glycoprotein in Human Colon Carcinoma Tissue and Cells," Journal of Cancer Research and Clinical Oncology, vol. 136, pp. 1697-16707, 2010.
Marme, Dieter et al., "Tumor Angiogenesis: Basic Mechanisms and Cancer Therapy," Springer-Verlag, pp. 1-17, 2008.

(56) References Cited

OTHER PUBLICATIONS

Ratti, Francesca et al., "Hilar Cholangiocarcinoma: Preoperative Liver Optimization with Multidisciplinary Approach. Toward a Better Outcome," World Journal Surg, vol. 37, pp. 1388-1396, 2013.
Aguirre, Diego A. et al., "Liver Fibrosis: Noninvasive Diagnosis with Double Contrast Material-Enhanced MR Imaging," Radiology, vol. 239, pp. 425-437, 2006.
Lubner, Meghan G. et al., "CT Textural Analysis of Hepatic Metastatic Colorectal Cancer: Pre-Treatment Tumor Heterogeneity Correlates with Pathology and Clinical Outcomes," Abdom Imaging, vol. 40, pp. 2331-2337, May 13, 2015.
Miles, Kenneth A. et al., "Colorectal Cancer: Texture Analysis of Portal Phase Hepatic CT Images as a Potential Marker of Survival," Radiology, vol. 250, No. 2, pp. 444-452, 2009.
Hayano, Koichi et al., "Fractal Analysis of Contrast-Enhanced CT Images to Predict Survival of Patients with Hepatocellular Carcinoma Treated with Sunitinib," Dig Dis Sci., vol. 59, No. 8, pp. 1996-2003, Aug. 2014.
Ng, Francesca et al., "Assessment of Primary Colorectal Cancer Heterogeneity by using Whole-Tumor Texture Analysis: Contrast-Enhanced CT Texture as a Biomarker of 5-year Survival," Radiology, vol. 266, No. 1, pp. 177-184, Jan. 2013.
Wu, Zhuo et al., "Hepatitis C Related Chronic Liver Cirrhosis: Feasibility of Texture Analysis of MR Images for Classification of Fibrosis Stage and Necroinflammatory Activity Grade," PLoS One, vol. 10, No. 3, pp. 1-11, 2015.
Simpson, Amber L. et al., "Texture Analysis of Preoperative CT Images for Prediction of Postoperative Hepatic Insufficiency: A Preliminary Study," Journal Am Coll Surg., vol. 220, No. 3, pp. 339-46, 2015.
Rao, Sheng-Xiang et al., "Whole-Liver CT Texture Analysis in Colorectal Cancer: Does the Presence of Liver Metastases affect the Texture of the Remaining Liver?," United Eur Gastroenterol Journal, vol. 2, No. 6, pp. 530-538, Dec. 2014.
Leen, Edward "The Detection of Occult Liver Metastases of Colorectal Carcinoma," Journal Hepatobiliary Pancreat Surg., vol. 6, No. 1, pp. 7-15, 1999.
Zakaria, Shaheen et al., "Hepatic Resection for Colorectal Metastases: Value for Risk Scoring Systems?," Ann Surg., vol. 246, No. 2, pp. 183-191, 2007.
Rees, Myrddin et al., "Evaluation of Long-Term Survival after Hepatic Resection for Metastatic Colorectal Cancer: A Multifactorial Model of 929 Patients," Ann Surg., vol. 247, No. 1, pp. 125-135, 2008.
Nordinger, Bernard et al., "Surgical Resection of Colorectal Carcinoma Metastases to the Liver. A Prognostic Scoring System to Improve Case Selection, Based on 1568 Patients," Association Française de Chirurgie. Cancer., vol. 77, No. 7, pp. 1254-1262, Apr. 1996.
Goere, Diane et al., "Adjuvant Chemotherapy After Resection of Colorectal Liver Metastases in Patients at High risk of Hepatic Recurrence: A Comparative Study Between Hepatic Arterial Infusion of Oxaliplatin and Modern Systemic Chemotherapy," Ann Surg., vol. 257, No. 1, pp. 114-120, 2013.
Kemeny, Nancy et al., "Hepatic Arterial Infusion of Chemotherapy after Resection of Hepatic Metastases from Colorectal Cancer," New Engl Journal Med., vol. 341, No. 27, pp. 2039-2048, 1999.
D'Angelica, Michael et al. "Effect on Outcome of Recurrence Patterns After Hepatectomy for Colorectal Metastases,"Ann Surg Oncol., vol. 18, No. 4, pp. 1096-1103, Apr. 2011.
Fong, Yuman et al., "Clinical Score for Predicting Recurrence after Hepatic Resection for Metastatic Colorectal Cancer: Analysis of 1001 Consecutive Cases," Ann Surg., vol. 230, No. 3, pp. 309-321,1999.
Mella, J. et al., "Population-Based Audit of Colorectal Cancer Management in two UK Health Regions," Cancer Working Group, Royal College of Surgeons of England Clinical Epidemiology and Audit Unit., British Journal Surg., vol. 84, No. 12, pp. 1731-1736, Dec. 1997.

Siegel, Rebecca et al., "Cancer Treatment and Survivorship Statistics," 2012. CA Cancer Journal Clin., vol. 62, No. 4, pp. 220-241, Aug. 2012.
Zhao, Tiansuo et al. "LASP1 is a HIF-1 Target Gene Critical for Metastasis of Pancreatic Cancer," Cancer Res [Internet]. Nov. 10, 2014[Accessed on Mar. 19, 2018]; <http://cancerres.aacrjournals.org/cgi/doi/10.1158/0008-5472.CAN-14-2040>.
Harrison, Louis B. et al., "Impact of Tumor Hypoxia and Anemia on Radiation Therapy Outcomes," The Oncologist, vol. 7, No. 6, pp. 492-508, 2002.
Song, Xianrang et al., "Hypoxia-Induced Resistance to Cisplatin and Doxorubicin in Non-small Cell Lung Cancer is Inhibited by Silencing of HIF-1Alpha Gene," Cancer Chemother Pharmacol., vol. 58, No. 6, pp. 776-784, Dec. 2006.
Aerts, Hugo J.W.L. et al., "Decoding Tumour Phenotype by Non-invasive Imaging using a Quantitative Radiomics Approach,"Nat Commun., vol. 5, pp. 1-8, 2014
Hata, Hiroyuki et al., "Fibrous Stroma and Vascularity of Pancreatic Carcinoma: Correlation with Enhancement Patterns on CT," Abdom Imaging., vol. 35, No. 2, pp. 172-180, Apr. 2010.
Harrori, Yuki et al., "Poorly Enhanced Areas of Pancreatic Adenocarcinomas on Late-Phase Dynamic Computed Tomography: Comparison with Pathological Findings," Pancreas, vol. 39, No. 8, pp. 1263-1270, Nov. 2010.
Chicklore, Sugama et al., "Quantifying Tumour Heterogeneity in 18F-FDG PET/CT Imaging by Texture Analysis," Eur Journal Nucl Med Mol Imaging, vol. 40, No. 1, pp. 133-140, Jan. 2013.
Dang, M. et al., "MRI Texture Analysis Predicts p53 Status in Head and Neck Squamous Cell Carcinoma," Am Journal Neuroradiol [Internet] [Accessed on Dec. 17, 2014] <:http://www.ajnr.org/cgi/doi/10.3174/ajnr.A4110>.
Yamamoto, Tatsuma et al., "Preoperative FDG-PET Predicts Early Recurrence and a Poor Prognosis After Resection of Pancreatic Adenocarcinoma," Ann Surg Oncol [Internet] [Accessed on Dec. 17, 2014], <http://link.springer.com/10.1245/s10434-014-4046-2>.
O'Reilly, Eileen M. et al., "A Single-Arm, Nonrandomized Phase II Trial of Neoadjuvant Gemcitabine and Oxaliplatin in Patients With Resectable Pancreas Adenocarcinoma," Ann Surg., vol. 260, No. 1, pp. 142-148, Jul. 2014.
Callery, Mark P. et al., "Pretreatment Assessment of Resectable and Borderline Resectable Pancreatic Cancer: Expert Consensus Statement," Ann Surg Oncol., vol. 16, No. 7, pp. 1727-1733, Jul. 2009.
Leen-Kiat, Soh et al., "Identifying Classes in SAR Sea Ice Imagery using Correlated Texture," IEEE, 1997 [Accessed on Dec. 17, 2014]. pp. 1177-1179. <http://ieeexplore.ieee.org/Ipdocs/epic03/wrapper.htm?arnumber=606389>.
Haralick, Robert M. "Statistical and Structural Approaches to Texture," Proceedings of the IEEE, vol. 67, No. 5, pp. 786-804, May 1979.
Haralick, Robert M. et al., "Textural Features for Image Classification," IEEE Transactions on Systems, Man, Cybernetics, vol. 3, No. 6, pp. 610-622, 1973.
Lambrechts, Diether et al., "Markers of Response for the Antiangiogenic Agent Bevacizumab," Journal of Clinical Oncology: Official Journal of the American Society of Clinical Oncology, vol. 31, No. 9, pp. 1219-1230, Mar. 20, 2013.
Banik, Shantanu et al., "Detection of Architectural Distortion in Prior Mammograms," IEEE Transactions of Medical Imaging, vol. 30, No. 2, pp. 279-294, 2011.
Banik, Shantanu et al., "Measures of Angular Spread and Entropy for the Detection of Architectural Distortion in Prior Mammograms," International Journal of Computer assisted Radiology and Surgery, vol. 8, No. 1, pp. 121-134, 2013.
Yang, Xiaofeng et al., "Ultrasound GLCM Texture Analysis of Radiation-Induced Parotid-Gland Injury in Head-and-Neck Cancer Radiotherapy: An in Vivo Study of Late Toxicity," Med Phys, vol. 39, pp. 5732-5739, 2012.
Midya, Abhishek et al., "Classification of Benign and Malignant Masses in Mammograms using Multi-Resolution Analysis of Oriented Patterns," In IEEE 12th International Symposium on Biomedical Imaging (ISBI), pp. 411-414 2015.

(56) References Cited

OTHER PUBLICATIONS

Chakraborty, Jayasree et al., "Statistical Measures of Orientation of Texture for the Detection of Architectural Distortion in Prior Mammograms of Interval Cancer," Journal of Electronic Imaging, vol. 1, No. 3, pp. 1-13, 2012.
Tang, Xiaoou "Texture Information in Run-Length Matrices," IEEE Transactions on Image Processing, vol. 7, No. 11, pp. 1602-1609, 1998.
Haralick, Robert M. et al., "Textural Features for Image Classification," Systems, Man and Cybernetics, IEEE Transactions On., vol. SMC-3, No. 6, pp. 610-621, Nov. 1973.
Wolf, Patrick S. et al., "Preoperative Chemotherapy and the Risk of Hepatotoxicity and Morbidity after Liver Resection for Metastatic Colorectal Cancer: A Single Institution Experience," Journal Am Coll Surg., vol. 216, No. 1, pp. 41-49, 2013.
Chakraborty, Jayasree et al., "Texture Analysis for Survival Prediction of Pancreatic Ductal Adenocarcinoma Patients with Neoadjuvant Chemotherapy," In SPIE Medical Imaging, vol. 9784, pp. 1-6, 2015.
Pang, Kwok, Kuen et al., "MR Imaging of the Musculoskeletal Soft Tissue Mass: Is Heterogeneity a Sign of Malignancy?," Journal of the Chinese Medical Association, vol. 66, No. 11, pp. 655-661, 2003.
Lloyd, Mark C. et al., "Using Image Analysis as a Tool for Assessment of Prognostic and Predictive Biomarkers for Breast Cancer: How reliable is it?," Journal of Pathology Informatics, vol. 1, pp. 1-29, 2013.
Balagurunathan, Yoganand et al., "Reproducibility and Prognosis of Quantitative Features Extracted from CT Images," Translational Oncology, vol. 7, No. 1, pp. 72-87, 2014.
Erkan, Mert et al., "Cancer-Stellate Cell Interactions Perpetuate the Hypoxia-Fibrosis Cycle in Pancreatic Ductal Adenocarcinoma," Neoplasia, vol. 11, No. 5, pp. 497-508, 2009.
Yoon, Soon Ho et al., "Small (i=20mm) Pancreatic Adenocarcinomas: Analysis of Enhancement Patterns and Secondary Signs with Multiphasic Multidetector CT," Radiology, vol. 259, No. 2, pp. 442-452, 2011.
Al-Hawary, Mahmoud M. et al., "Pancreatic Ductal Adenocarcinoma Radiology Reporting Template: Consensus Statement of the Society of Abdominal Radiology and the American Pancreatic Association," Radiology, vol. 270, No. 1, pp. 248-260, 2014.
Bilici, Ahmet, "Prognostic Factors Related with Survival in Patients with Pancreatic Adenocarcinoma," World Journal of Gastroenterology, vol. 20, No. 31, pp. 10802-10812, 2014.
Hallemeier, Christopher. L et al., "Preoperative CA 19-9 Level is an Important Prognostic Factor in Patients with Pancreatic Adenocarcinoma Treated with Surgical Resection and Adjuvant Concurrent Chemoradiotherapy," American Journal of Clinical Oncology, vol. 34, No. 6, pp. 567-572, 2011.
Brennan, Murray F. et al., "Prognostic Nomogram for Patients undergoing Resection for Adenocarcinoma of the Pancreas," Annals of Surgery, vol. 240, No. 2, pp. 293-298, 2011.
A. C. Society, "Cancer Facts & Figures, 2014," Atlanta American Cancer Society, pp. 1-72, 2014.
Lehmann, Kuno et al., "Chemotherapy Before Liver Resection of Colorectal Metastases: Friend or Foe?," Ann Surg. vol. 255, No. 2, pp. 237-247, Feb. 2012.
Kanemitsu, Yukihide et al., "Prognostic Models for Predicting Death after Hepatectomy in Individuals with Hepatic Metastases from Colorectal Cancer," World J Surg., vol. 32, No. 6, pp. 1097-1107, Jun. 2008.
Yamaguchi, Tatsuro et al., "A New Classification System for Liver Metastases from Colorectal Cancer in Japanese Multicenter Analysis," Hepatogastroenterology, vol. 55, No. 81, pp. 173-178, Feb. 2008.
Lorenz, Matthias et al., "Randomized Trial of Surgery Versus Surgery Followed by Adjuvant Hepatic Arterial Infusion with 5-Fluorouracil and Folinic Acid for Liver Metastases of Colorectal Cancer," German Cooperative on Liver Metastases (Arbeitsgruppe Lebermetastasen). Ann Surg., vol. 228, No. 6, pp. 756-762, Dec. 1998.

Costa-Silva, Bruno et al., "Pancreatic Cancer Exosomes Initiate Pre-Metastatic Niche Formation in the Liver," Nat Cell Biol., vol. 17, No. 6, pp. 1-7, 2015.
Van Der Wal, Gesiena E. et al., "Reply to Letter: Markers of Angiogenesis in Synchronous and in Metachronous Colorectal Hepatic Metastases," Ann Surg. vol. 261, No. 1, :e20-e21, Jan. 2015.
Van Der Wal, Gesiena et al., "Angiogenesis in Synchronous and Metachronous Colorectal Liver Metastases: The Liver as a Permissive Soil," Ann Surg., vol. 255, No. 1, pp. 86-94, Jan. 2012.
Poultsides, George A. et al., "Pathologic Response to Preoperative Chemotherapy in Colorectal Liver Metastases: Fibrosis, not Necrosis, Predicts Outcome," Ann Surg Oncol. vol. 19, No. 9, pp. 2797-7804, 2012.
Basch, Ethan et al., "Development of the National Cancer Institute's Patient-Reported Outcomes Version of the Common Terminology Criteria for Adverse Events (PRO-CTCAE)," Journal Natl Cancer Inst., vol. 106, No. 9, pp. 1-11, Sep. 2014.
Gonzalez, Rafael C. et al., "Digital Image Processing," 3rd ED. Upper Saddle River, N.J: Prentice Hall, pp. 1-954 2008.
Russ, John C. "The Image Processing Handbook," 6th ED, Boca Raton: CRC Press; pp. 1-878,2011.
Hunter, L.A. et al., "High Quality Machine Robust Image Features: Identification in Non-small Cell Lung Cancer Computed Tomography Images," Med Phys, vol. 40, pp. 1-13, 2013.
Chun, Yun Shin et al., "Association of Computed Tomography Morphologic Criteria with Pathologic Response and Survival in Patients Treated with Bevacizumab for Colorectal Liver Metastases," JAMA. American Medical Association, vol. 302, No. 21, pp. 2338-2344, Dec. 2009.
Kleiner, David E. et al., "Design and Validation of a Histological Scoring System for Nonalcoholic Fatty Liver Disease," Hepatology, vol. 41, No. 6, pp. 1313-1321, 2005.
Rubbia-Brandt, L. et al., "Severe Hepatic Sinusoidal Obstruction Associated with Oxaliplatin-Based Chemotherapy in Patients with Metastatic Colorectal Cancer," Ann Oncol., vol. 15, No. 3, pp. 460-466, 2004.
Hoshino, Ayuko et al., "Tumour Exosome Integrins Determine Organotropic Metastasis," Nature, pp. 1-19, 2015.
Pietikainen, Matti et al., "Local Binary Patterns for Still Images," In Computer Vision Using Local Binary Patterns, Computational Imaging and Vision 40, pp. 1-212, Springer London, 2011.
National Comprehensive Cancer Network. NCCN Clinical Practice Guidelines in Oncology, Version 3.2014. [Accessed on Internet] [Accessed on Aug. 20, 2014] <http://www.nccn.org/professionals/physician_gls/pdf/colon.pdf>.
Duda, R. O. et al., "Pattern Classification," Wiley-Interscience, New York, NY, 2nd ed. pp. 1-674, 2001.
Wong, J.S. et al., "Liver Stiffness Measurement by Transient Elastography as a Predictor on Posthepatectomy Outcomes," Ann. Surg., vol. 257, pp. 922-928, 2013.
Buczkowski, Stephane et al., "The Modified Boxcounting Method: Analysis of Some Characteristic Parameters," Pattern Recognition, vol. 31, pp. 411-418, 1998.
Ojala, Timo et al.,"A Comparative Study of Texture Measures with Classification based on Feature Distributions," Pattern Recognition vol. 29, pp. 51-59, 1996.
Iwatsuki, Shunzaburo et al., "Hepatic Resection for Metastatic Colorectal Adenocarcinoma: A Proposal of a Prognostic Scoring System," Journal Am Coll Surg., vol. 189, No. 3, pp. 291-299, Sep. 1999.
Eveno, Clarisse et al., "Proof of Prometastatic Niche Induction by Hepatic Stellate Cells," Journal Surg Res., vol. 194, No. 2., pp. 496-504, Apr. 2015.
Ba-Ssalamah, Ahmed et al., "Texture-Based Classification of Different Gastric Tumors at Contrast-Enhanced CT," Eur J Radiol., Elsevier Ireland Ltd; vol. 82., No. 10., pp. e537-43, 2013.
Ganeshan, B. et al., "Hepatic Entropy and Uniformity: Additional Parameters that can Potentially Increase the Effectiveness of Contrast Enhancement during Abdominal CT," Clin Radiol., vol. 62, No. 8, pp. 761-768, Aug. 2007.

(56) References Cited

OTHER PUBLICATIONS

Conzelmann, M. et al., "Detection of Disseminated Tumour Cells in the Liver of Colorectal Cancer Patients," Journal Eur Soc Surg Oncol Br Assoc Surg Oncol., vol. 31, No. 1., pp. 38-44, Feb. 2005.
House, Michael G. et al., "Survival After Hepatic Resection for Metastatic Colorectal Cancer: Trends in Outcomes for 1,600 Patients during Two Decades at a Single Institution," Journal Am Coll Surg. vol. 210, No. 5., pp. 744-752, 2010.
Huang, Yu-Len et al., "Diagnosis of Hepatic Tumors with Texture Analysis in Nonenhanced Computed Tomography Images," Acad Radiol, vol. 13, pp. 713-720, 2006.
Su, Min-Cheng et al., "CD24 Expression is a Prognostic Factor in Intrahepatic Cholangiocarcinoma," Cancer Letters, vol. 235, pp. 34-39, 2006.
Ohanian, Philippe P. et al., "Performance Evaluation for Four Classes of Textural Features," Pattern Recognition, vol. 25, pp. 819-833, 1992.
Martin II, Robert CG et al., "Achieving R0 Resection for Locally Advanced Gastric Cancer: Is It Worth the Risk of Multiorgan Resection?," Journal Am Coll Surg, vol. 194, pp. 568-577, 2002.
Barry, Brian et al., "Quantifying Liver Fibrosis Through the Application of Texture Analysis to Diffusion Weighted Imaging," Magnetic Resonance Imaging, vol. 32, pp. 84-90, 2014.
Allen, Peter J. et al., "Importance of Response to Neoadjuvant Chemotherapy in Patients Undergoing Resection of Synchronous Colorectal Liver Metastases," Journal Gastrointest Surg Off Journal Soc Surg Aliment Tract, vol. 7, No. 1, pp. 109-115; Discussion No. 116-117, Jan. 2003.
Kemeny, N. et al., "Phase I Trial of Systemic Oxaliplatin Combination Chemotherapy With Hepatic Arterial Infusion in Patients With Unresectable Liver Metastases From Colorectal Cancer," Journal Clin Oncol., vol. 23, No. 22, pp. 4888-4896, Jun. 2005.
Portier, G. et al., "Multicenter Randomized Trial of Adjuvant Fluorouracil and Folinic Acid Compared with Surgery Alone after Resection of Colorectal Liver Metastases: FFCD ACHBTH AURC 9002 Trial," Journal Clin Oncol. vol. 24, No. 31, pp. 4976-4982, 2006.
Swinson, Deb et al., "Carbonic Anhydrase IX Expression, A Novel Surrogate Marker of Tumor Hypoxia, Is Associated with a Poor Prognosis in Non-Small-Cell Lung Cancer," Journal Clin Oncol Off J Am Soc Clin Oncol. vol. 21, No. 3 ,pp. 473-482 Feb. 1, 2003.
D'Angelica, Michael I. et al., "Phase II Trial of Hepatic Artery Infusional and Systemic Chemotherapy for Patients with Unresectable Hepatic Metastases from Colorectal Cancer: Conversion to Resection and Long-Term Outcomes," Ann Surg. vol. 261, No. 2, pp. 353-360, 2015.
Callery, Mark P. et al., "Pretreatment Assessment of Resectable and Borderline Resectable Pancreatic Cancer: Expert Consensus Statement," Annals of Surgical Oncology, vol. 16, No. 7, pp. 1727-1733, 2009.
Spiteri, M. et al., "Pancreatic Cancer Early Detection: Expanding Higher-Risk Group with Clinical and Metabolomics Parameters," Journal of Medical Imaging, vol. 2, No. 4, 044502-1-044502-9, 2015
Antonelli, Michela et al., "Feature Selection Based on Fuzzy Mutual Information," In Fuzzy Logic and Applications, Lecture Notes in Computer Science 8256, Springer International Publishing, pp. 36-43, 2013.
Peng, Hanchuan et al., "Feature Selection based on Mutual Information: Criteria of Max-Dependency, Max-Relevance, and Min-Redundancy," IEEE Transactions on Pattern Analysis and Machine Intelligence, vol. 27, No. 8, pp. 1226-1238, 2005.
Al-Ani, Ahmed et al., "A Population Based Feature Subset Selection Algorithm Guided by Fuzzy Feature Dependency," in Advanced Machine Learning Technologies and Applications, vol. 322, pp. 430-438, 2012.
Khushaba, Rami N. et al., "Driver Drowsiness Classification using Fuzzy Wavelet Packet based Feature Extraction Algorithm," IEEE Transaction on Biomedical Engineering, vol. 58, No. 1, pp. 121-131, 2011.
Costa, Alceu Ferraz et al., "An Efficient Algorithm for Fractal Analysis of Textures," In Proceedings of the 25th SIBGRAPI Conference on Graphics, Patterns and Images (SIBGRAPI 2012), pp. 39-46, 2012.
Prigarin, S. M. et al., "Estimation of Fractal Dimension: A Survey with Numerical Experiments and Software Description," International Journal of Biomathematics and Biostatistics, vol. 2, No. 1, pp. 167-180, 2013.
Al-Kadi, Omar S. et al., "Texture Analysis of Aggressive and Nonaggressive Lung Tumor CE CT Images," IEEE Transactions on Biomedical Engineering, vol. 55, No. 7, pp. 1822-1830, 2008.
Ahonen, Timo et al., "Rotation Invariant Image Description with Local Binary Pattern Histogram Fourier Features," In Proceedings of 16th Scandinavian Conference on Image Analysis (SCIA 2009), vol. 5575, pp. 61-70, 2009.
Yang, Xiaofeng et al., "Ultrasound GLCM Texture Analysis of Radiation-Induced Parotid-Gland Injury in Head and-Neck Cancer Radiotherapy: An in Vivo Study of Late Toxicity," Medical Physics, vol. 39, No. 9, pp. 5732-5739, 2012.
O'Conner, JPB et al., "DCE-MRI Biomarkers of Tumour Heterogeneity Predict CRC Liver Metastasis Shrinkage Following Bevacizumab and FOLFOX-6," British Journal Cancer, vol. 105, pp. 139-145, 2011.
Harrison, Lara CV et a., "Non-Hodgkin Lymphoma Response Evaluation with MRI Texture Classification," Journal Experiment Clin Cancer Res, vol. 28, No. 87, pp. 1-13, 2009.
Julesz, B. et al., "Inability of Humans to Discriminate Between Visual Textures that Agree in Second-Order Statistics-Revisited," Perception, vol. 2 pp. 391-405, 1973.
Lock, J.F. et al., "The Costs of Postoperative Liver Failure and the Economic Impact of Liver Function Capacity After Extended Liver Resection—A Single-Center Experience," Langenbecks Arch Surg., vol. 394, No. 6, pp. 1047-1056, 2009.
Van Den Broek, Maartje A.J. et al., "Liver Failure after Partial Hepatic Resection: Definition, Pathophysiology, Risk Factors and Treatment," Liver Int, vol. 28, pp. 767-780, 2008.
Haralick, Robert M. "Statistical and Structural Approaches to Texture," Proc IEEE., vol. 67, No. 5, pp. 786-804, 1979.
Haralick, Robert M. et al., "Textural Features for Image Classification," Syst Man Cybern IEEE Trans., vol. SMC-3, No. 6, pp. 610-621, Nov. 1973.
Soh-Leen-Kiat "Texture Analysis of SAR Sea Ice Imagery using Gray Level Co-Occurrence Matrices," IEEE Transactions on Geoscience and Remote Sensing, pp. 780-795, 1999.
Rubbia-Brandt, L. et al., "Severe Hepatic Sinusoidal Obstruction Associated with Oxaliplatin-Based Chemotherapy in Patients with Metastatic Colorectal Cancer," Ann Oncol., vol. 15, pp. 460-466, 2004.
Kleinder, David E. et al., "Design and Validation of a Histological Scoring System for Nonalcoholic Fatty Liver Disease," Hepatology, vol. 41, pp. 1313-1321, 2005.
Wibmer, Andreas et al., "Liver Failure after Major Liver Resection: Risk Assessment by using Preoperative Gadoxetic Acid-Enhanced 3-T MR Imaging," Radiology, vol. 269, pp. 777-786, 2013.
Marsman, H.A. et al. "Hepatic Steatosis Assessment with CT or MRI in Patients with Colorectal Liver Metastases after Neoadjuvant Chemotherapy," Journal Surg Oncol, vol. 04, pp. 10-16, 2011.
Lam, C.M. et al., "Major Hepatectomy for Hepatocellular Carcinoma in Patients with an Unsatisfactory Indocyanine Green Clearance Test," British Journal Surg, vol. 86, pp. 1012-1017, 1999.
Hoekstra, Lisette T. et al., "Physiological and Biochemical Basis of Clinical Liver Function Tests: A Review," Ann Surg, vol. 257, pp. 27-36, 2013.
Shoup, Margo et al., "Volumetric Analysis Predicts Hepatic Dysfunction in Patients undergoing Major Liver Resection," Journal Gastrointest Surg, vol. 7, pp. 325-330, 2003.
Kishi, Yoji et al., "Three Hundred and One Consecutive Extended Right Hepatectomies: Evaluation of Outcome based on Systematic Liver Volumetry,". Ann Surg, vol. 250, pp. 540-548, 2009.
Schindl, M.J. et al. "The Value of Residual Liver Volume as a Predictor of Hepatic Dysfunction and Infection after Major Liver Resection," Gut, vol. 54, pp. 289-296, 2005.

(56) References Cited

OTHER PUBLICATIONS

Jarnagin, William R. et al., "Improvement in Perioperative Outcome after Hepatic Resection: Analysis of 1,803 Consecutive Cases over the Past Decade," Ann Surg., vol. 236, pp. 397-406, Discussion 406-407, 2002.

Dokmak, Safi et al., "2012 Liver Resections in the 21st Century: We are far from Zero Mortality," HPB, vol. 15, pp. 908-915, 2013.

Howlader, N. et al., (eds), "SEER Cancer Statistics Review," 1975-2012, National Cancer Institute.

\* cited by examiner

| TEXTURE FEATURE | NLI | LI |
|---|---|---|
| CONTRAST | 0.55 | 1.27 |
| CORRELATION | 0.07 | 0.02 |
| ENTROPY | 0.46 | 0.54 |
| HOMOGENEITY | 0.79 | 0.65 |
| ENERGY | 0.36 | 0.13 |

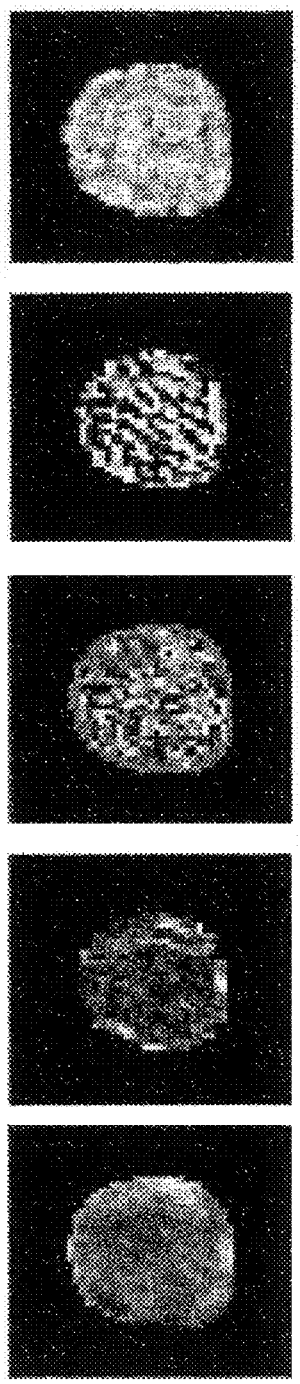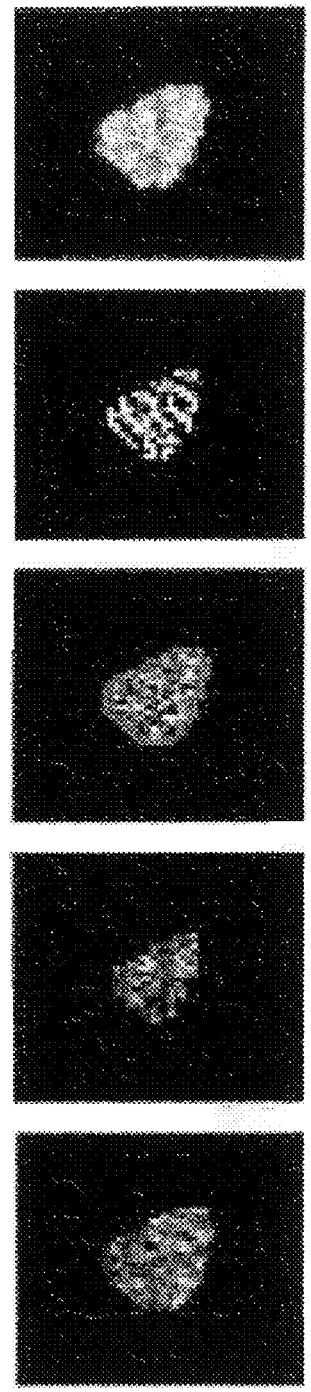

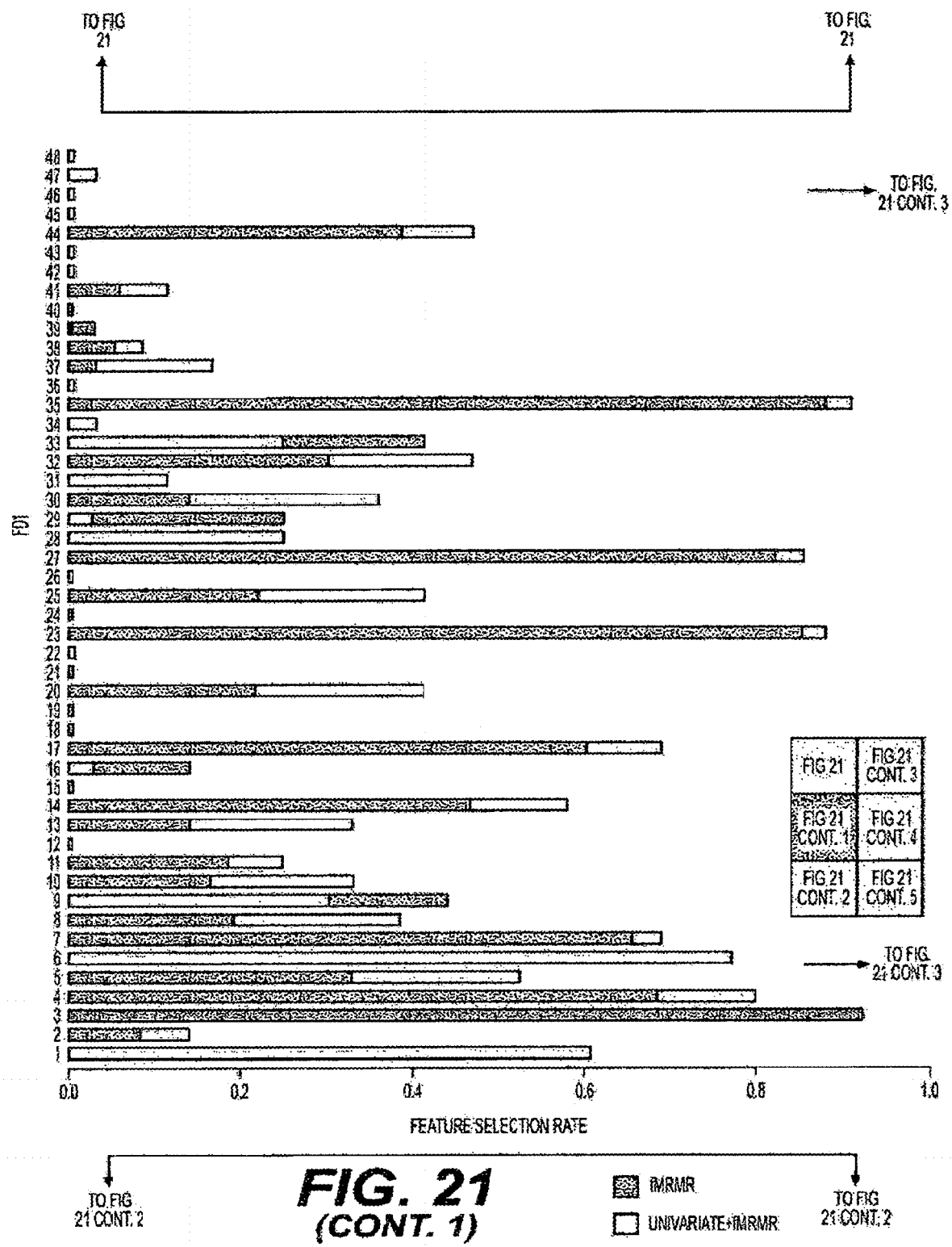
FIG. 21 (CONT. 1)

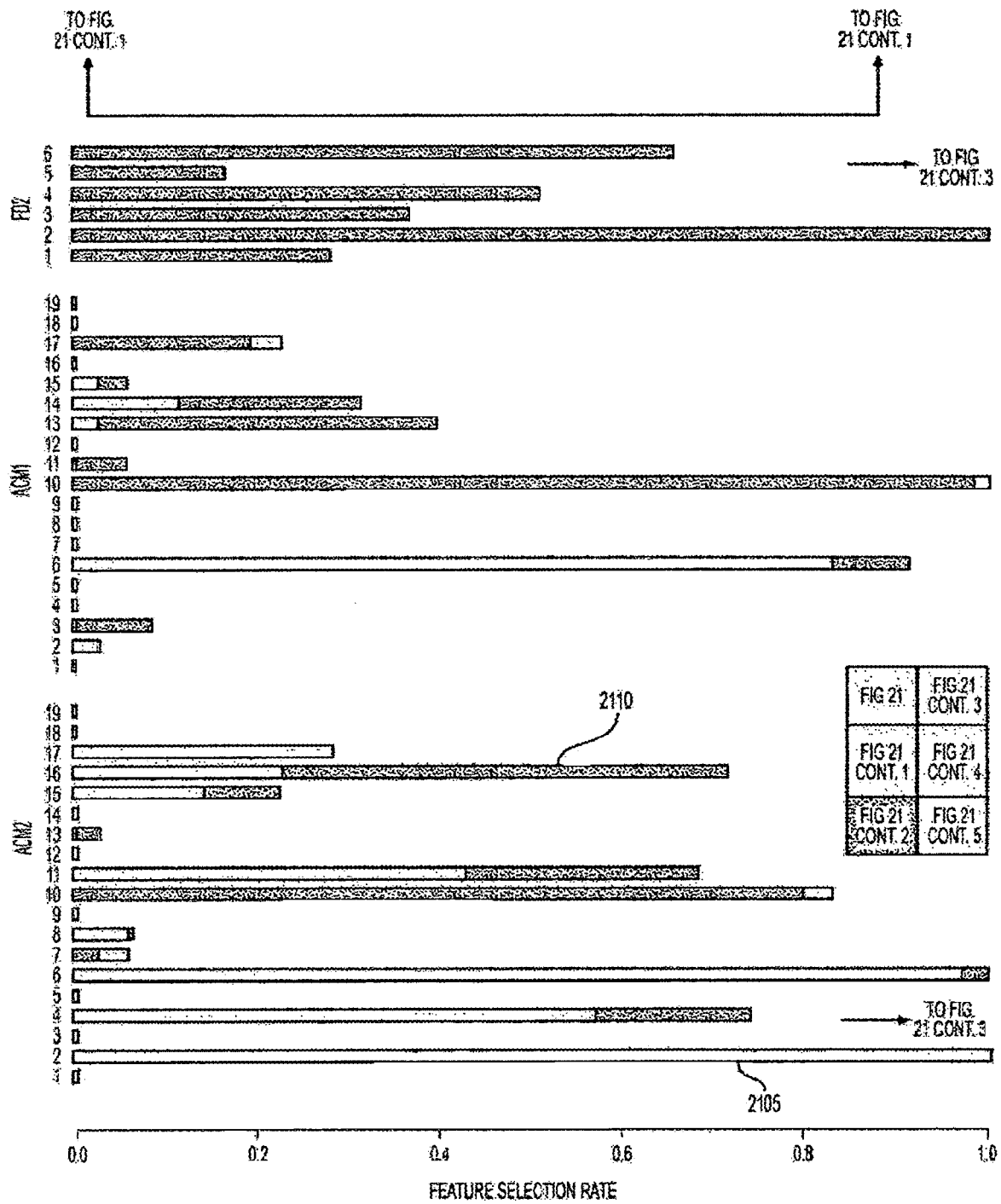
FIG. 21 (CONT. 2)

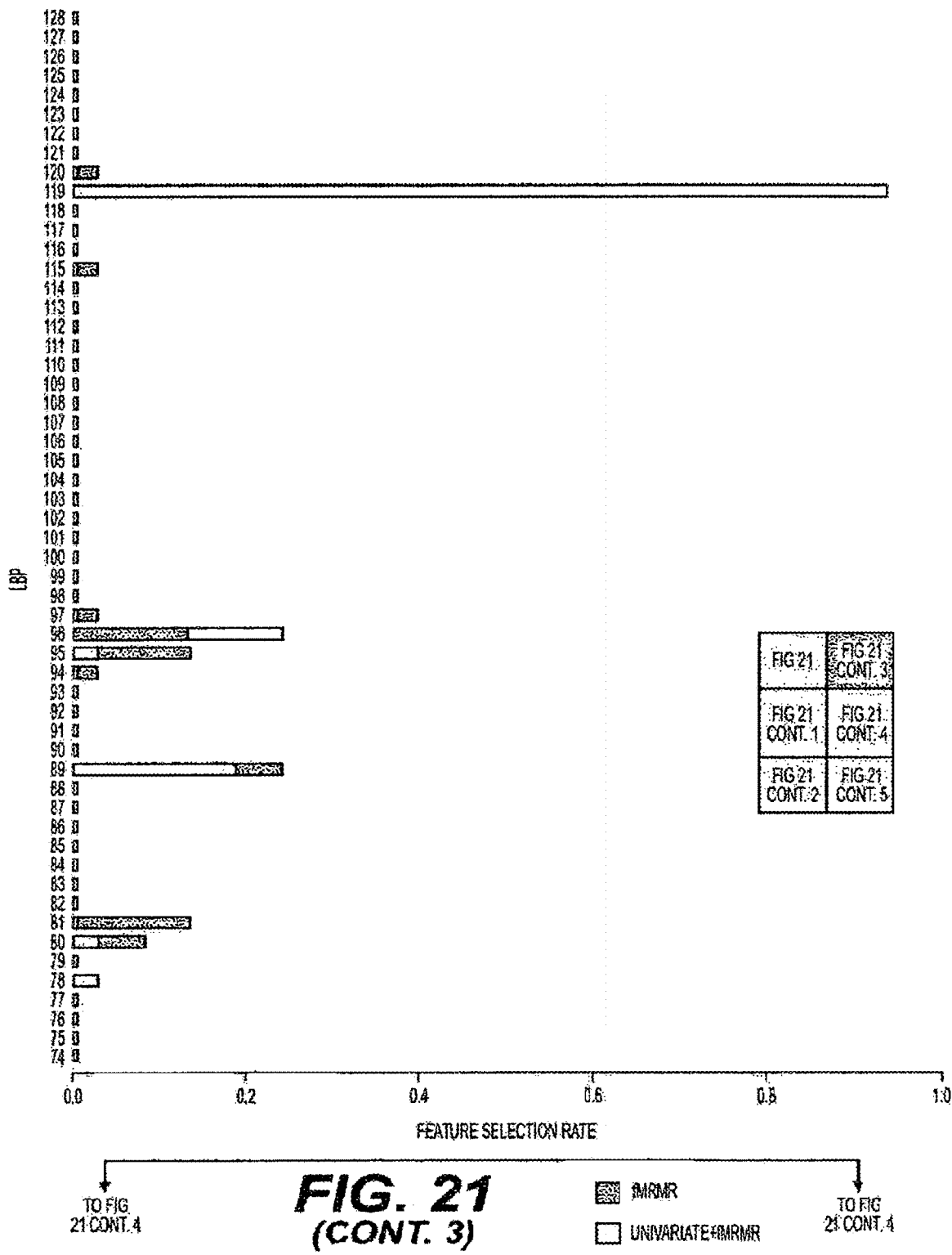
FIG. 21 (CONT. 3)

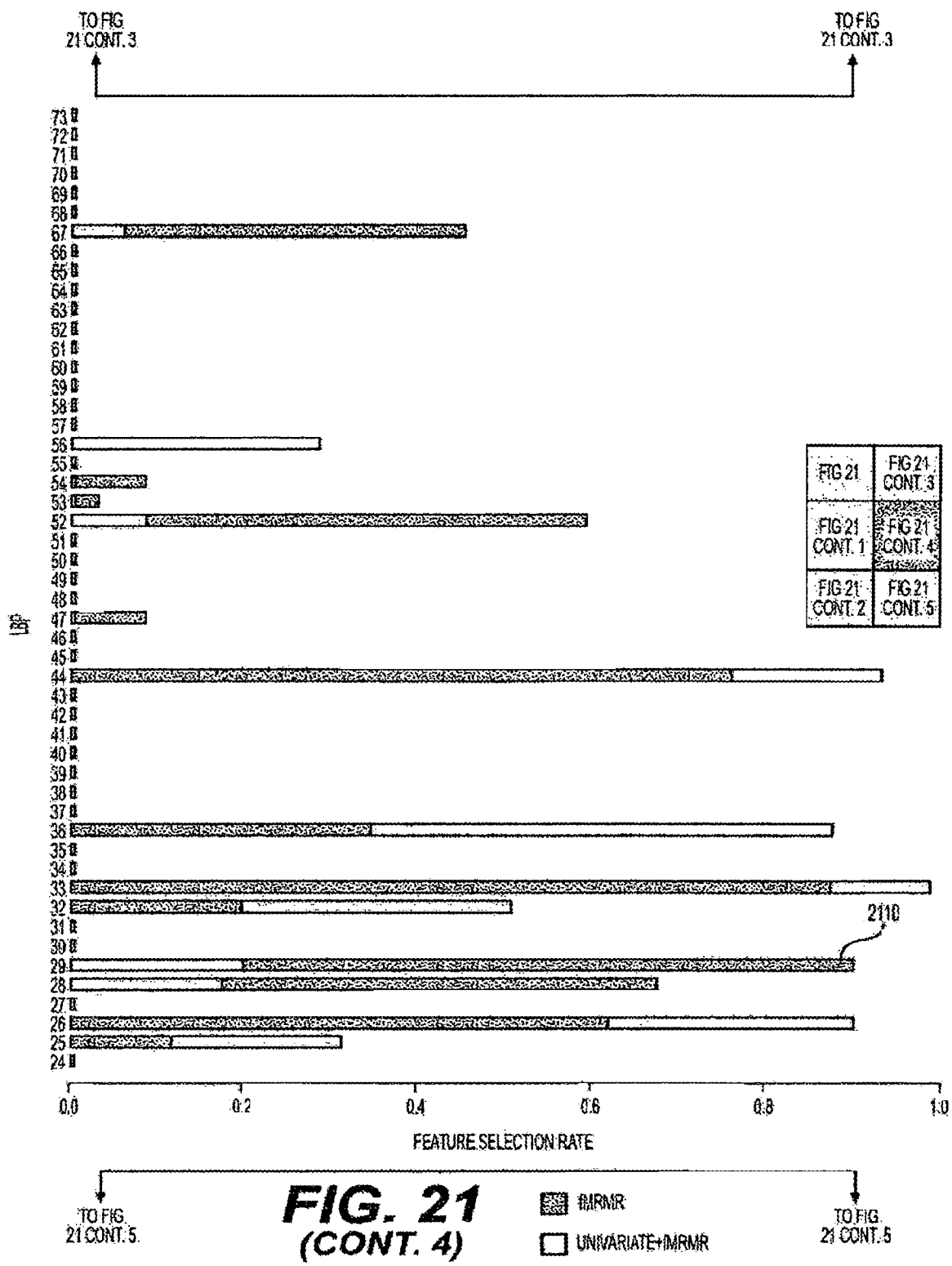
FIG. 21 (CONT. 4)

(CONT. 5)

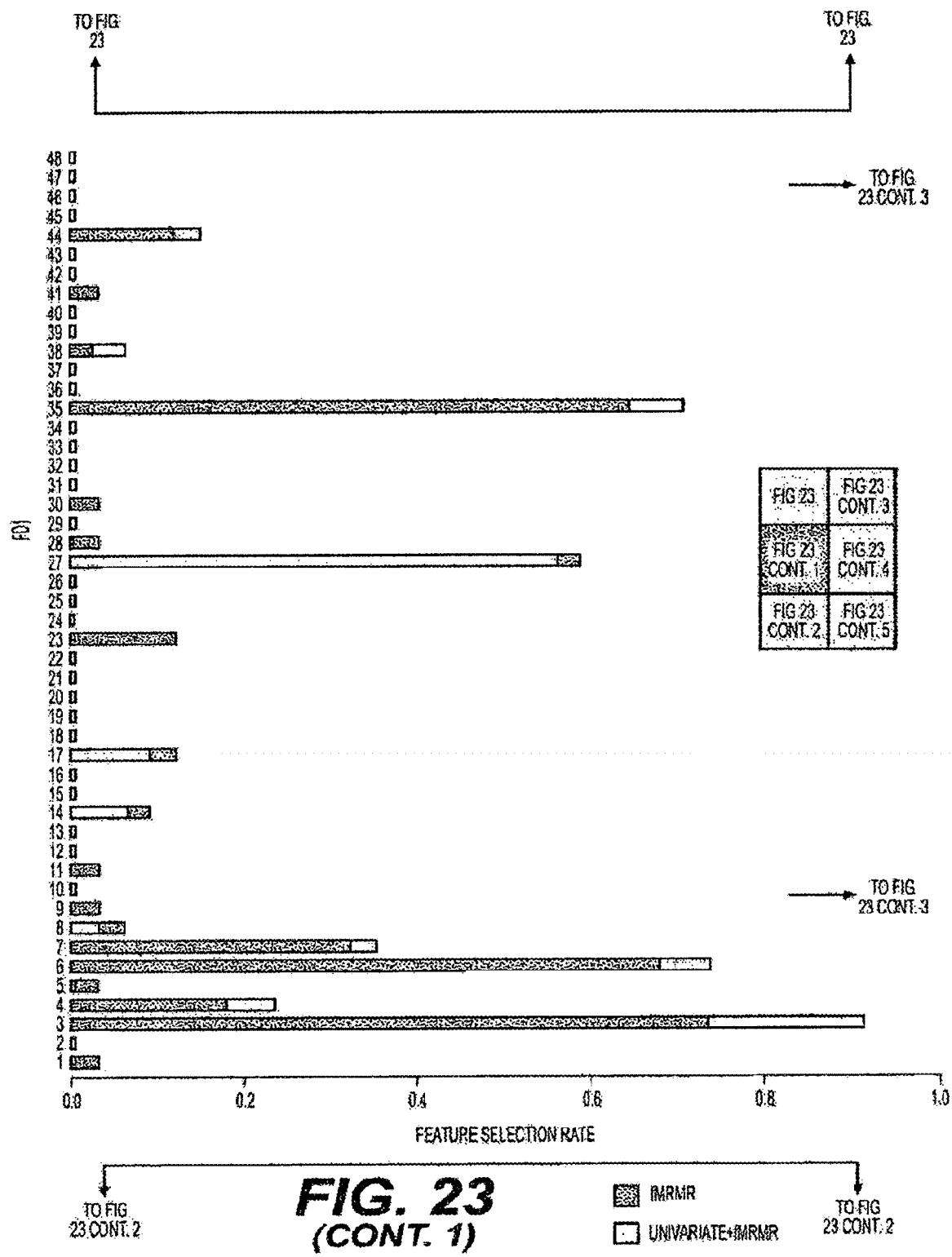
FIG. 23 (CONT. 1)

(CONT. 2)

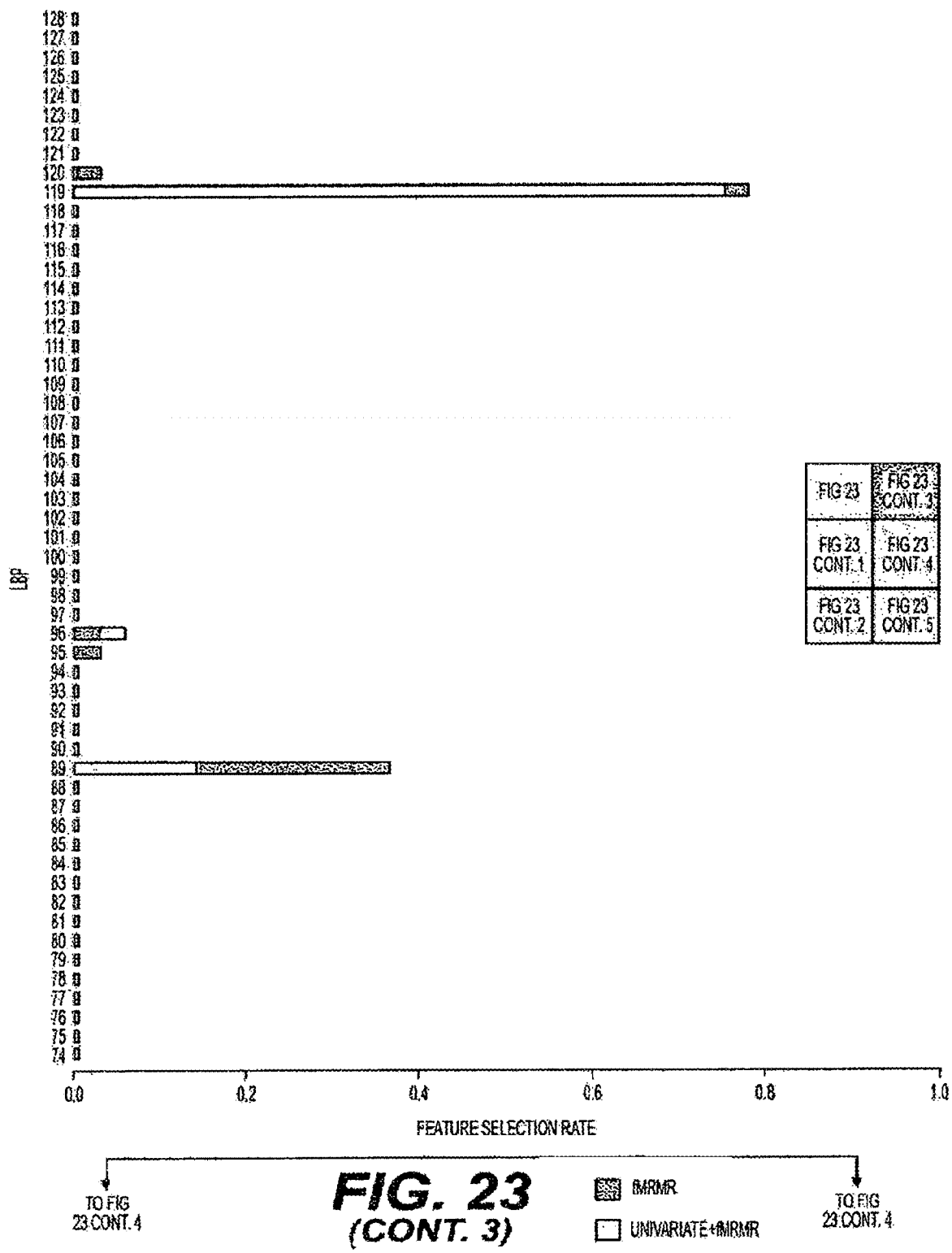
FIG. 23 (CONT. 3)

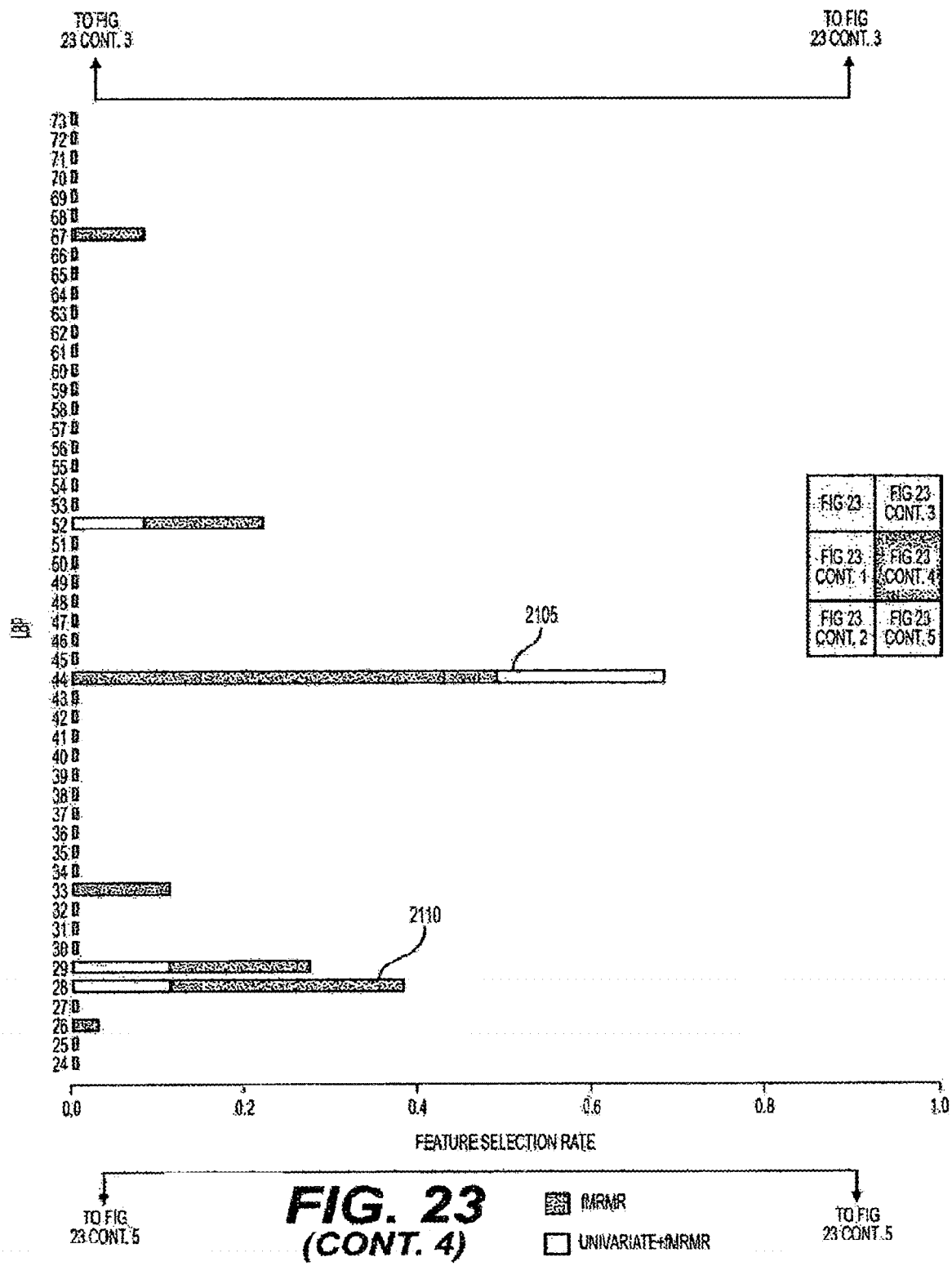
FIG. 23 (CONT. 4)

*(CONT. 5)*

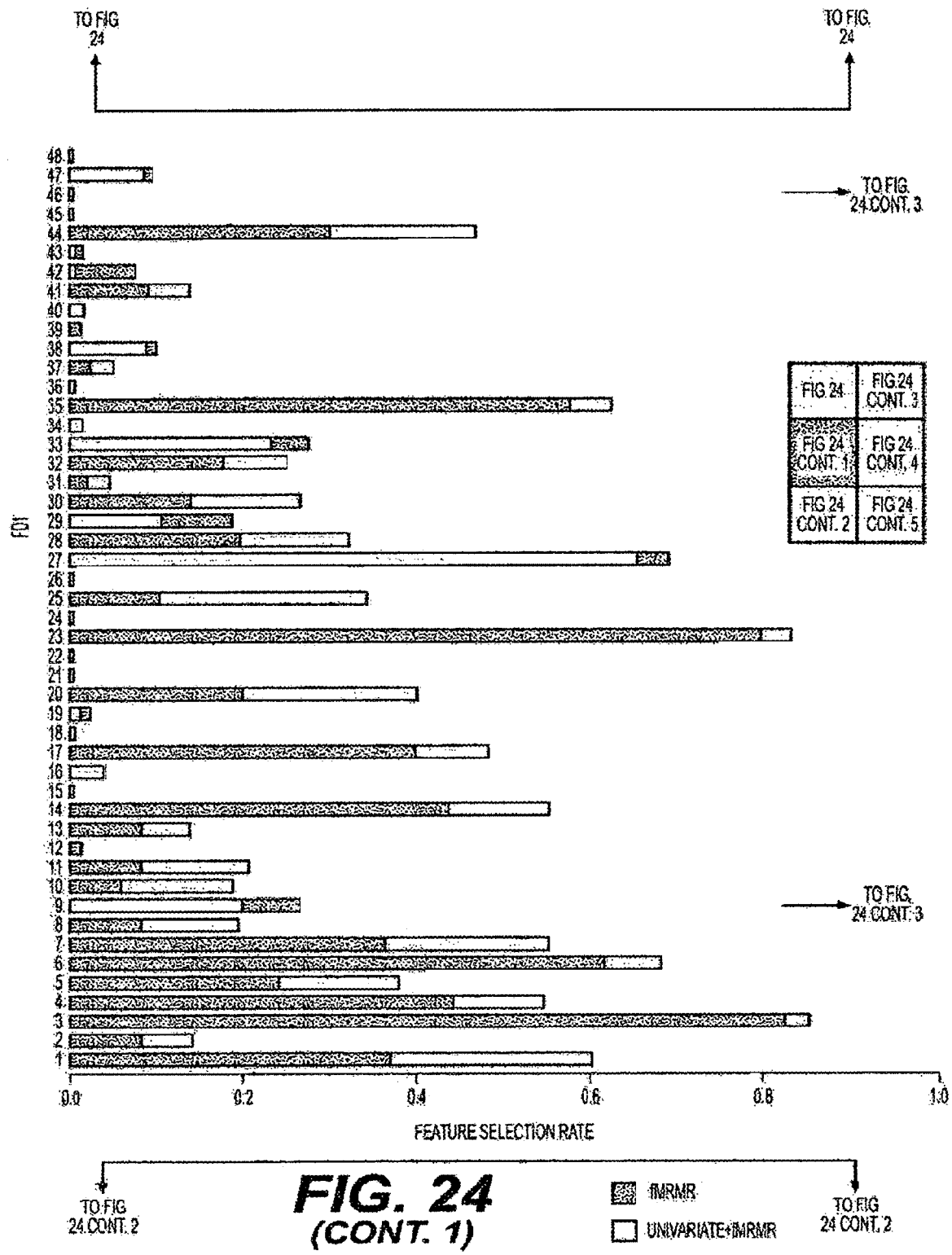
FIG. 24 (CONT. 1)

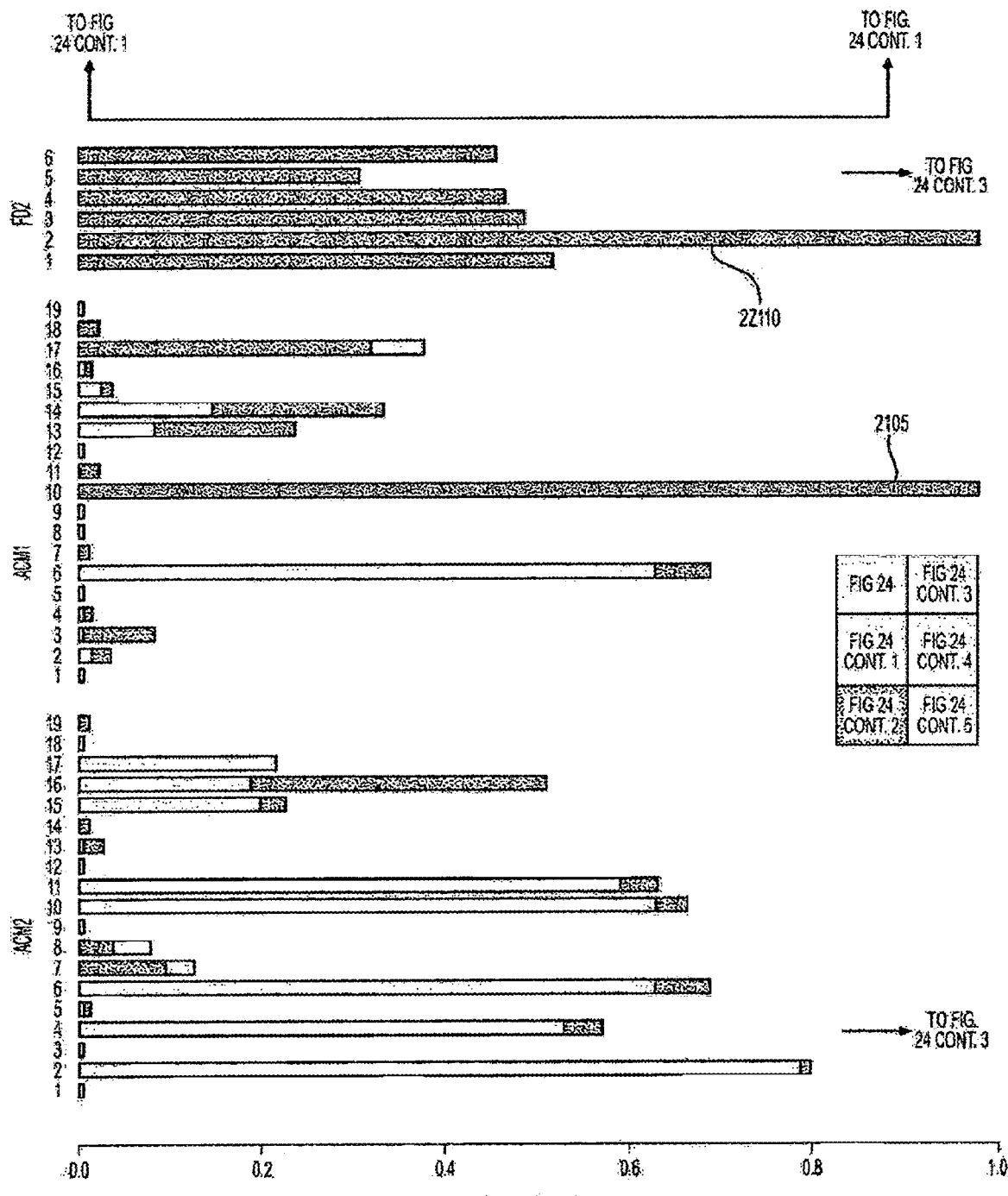
FIG. 24 (CONT. 2)

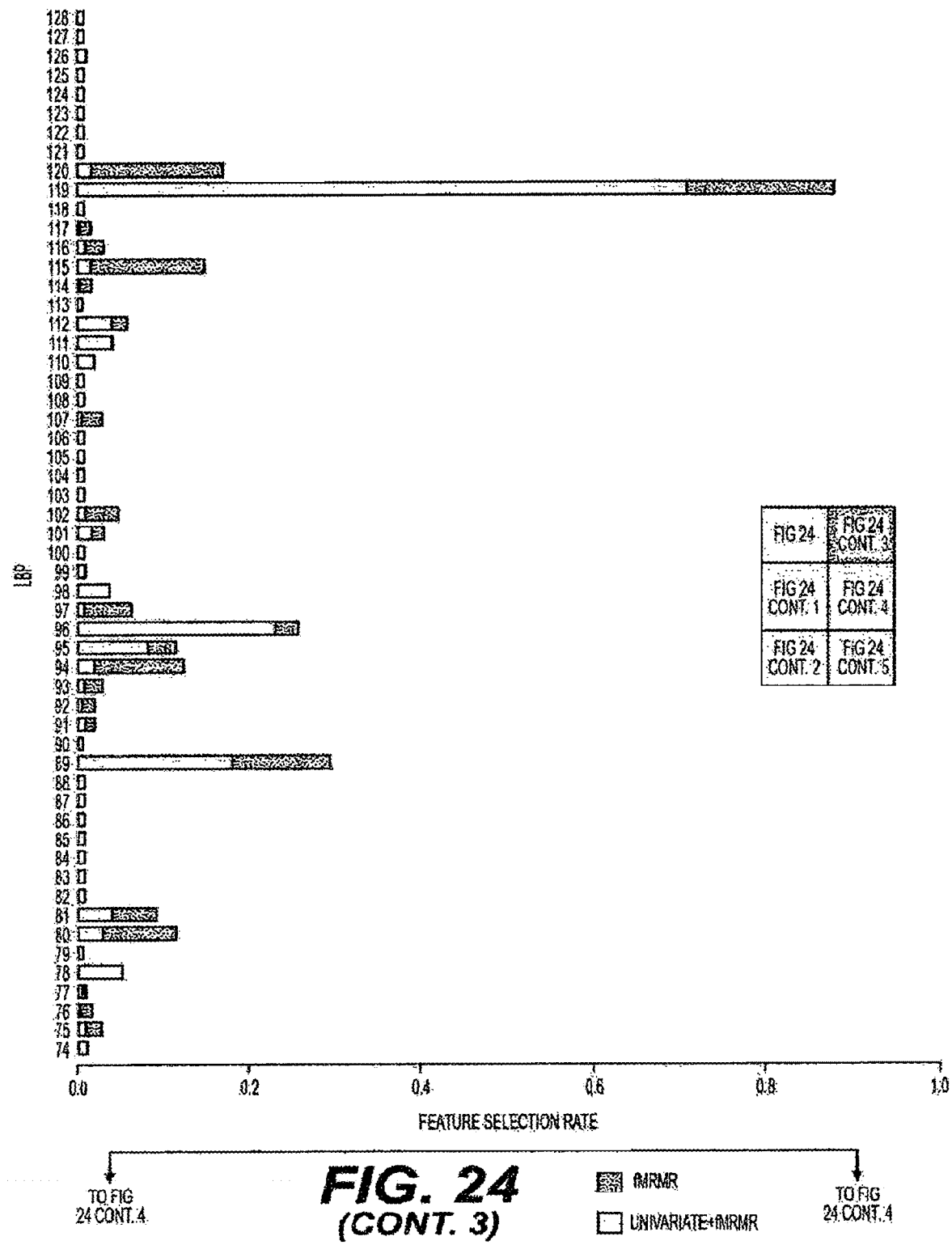
FIG. 24 (CONT. 3)

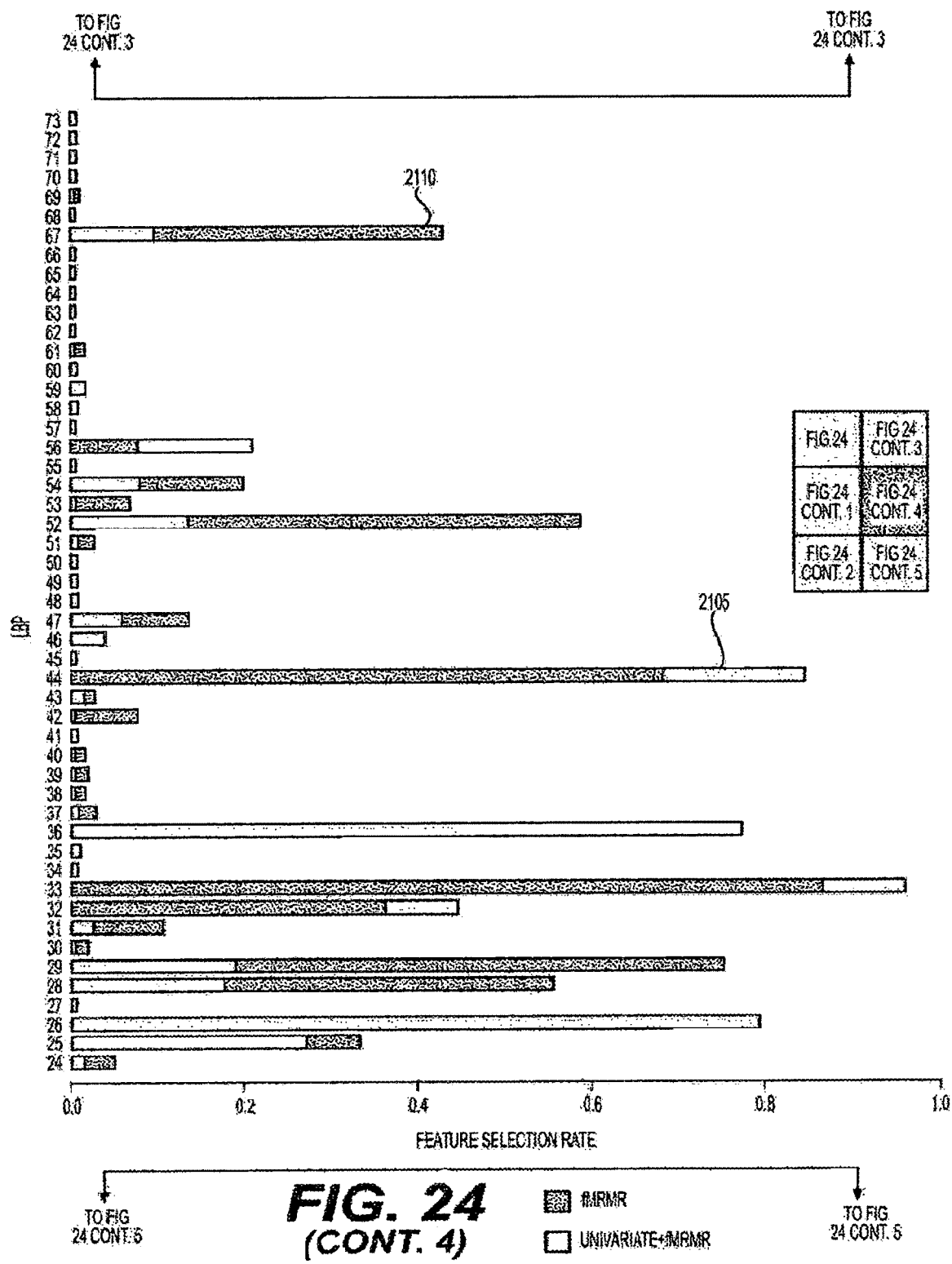
FIG. 24 (CONT. 4)

*(CONT. 5)*

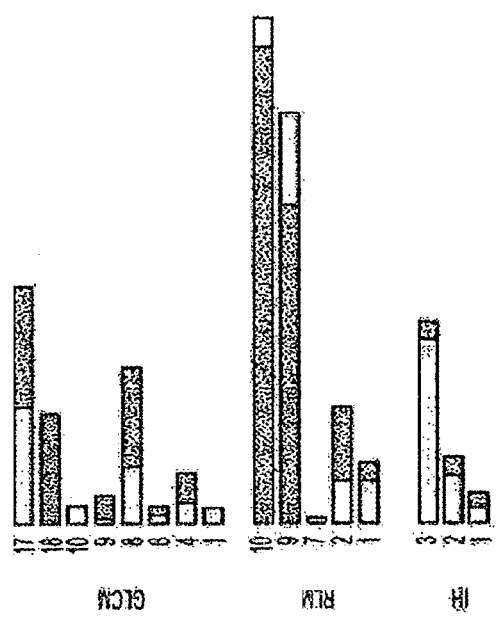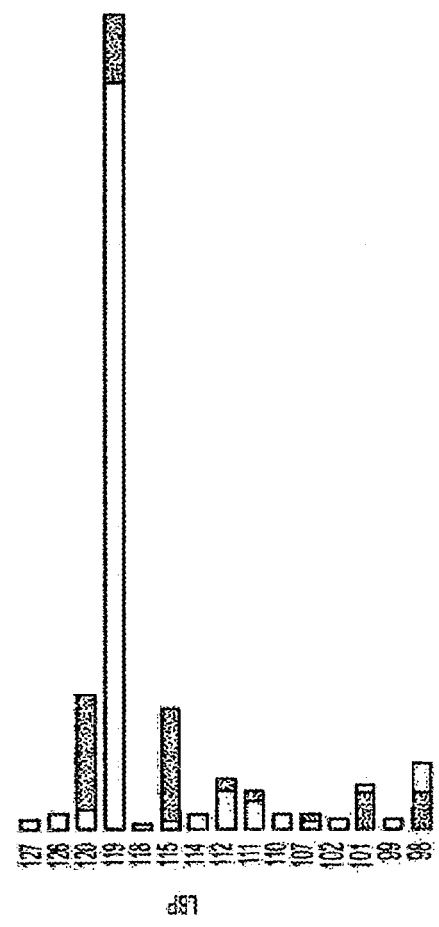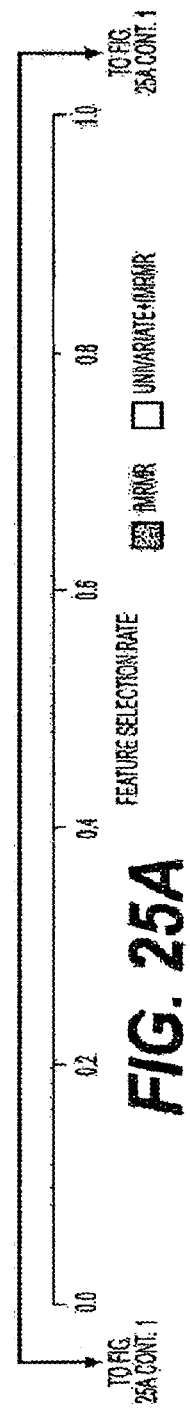
FIG. 25A

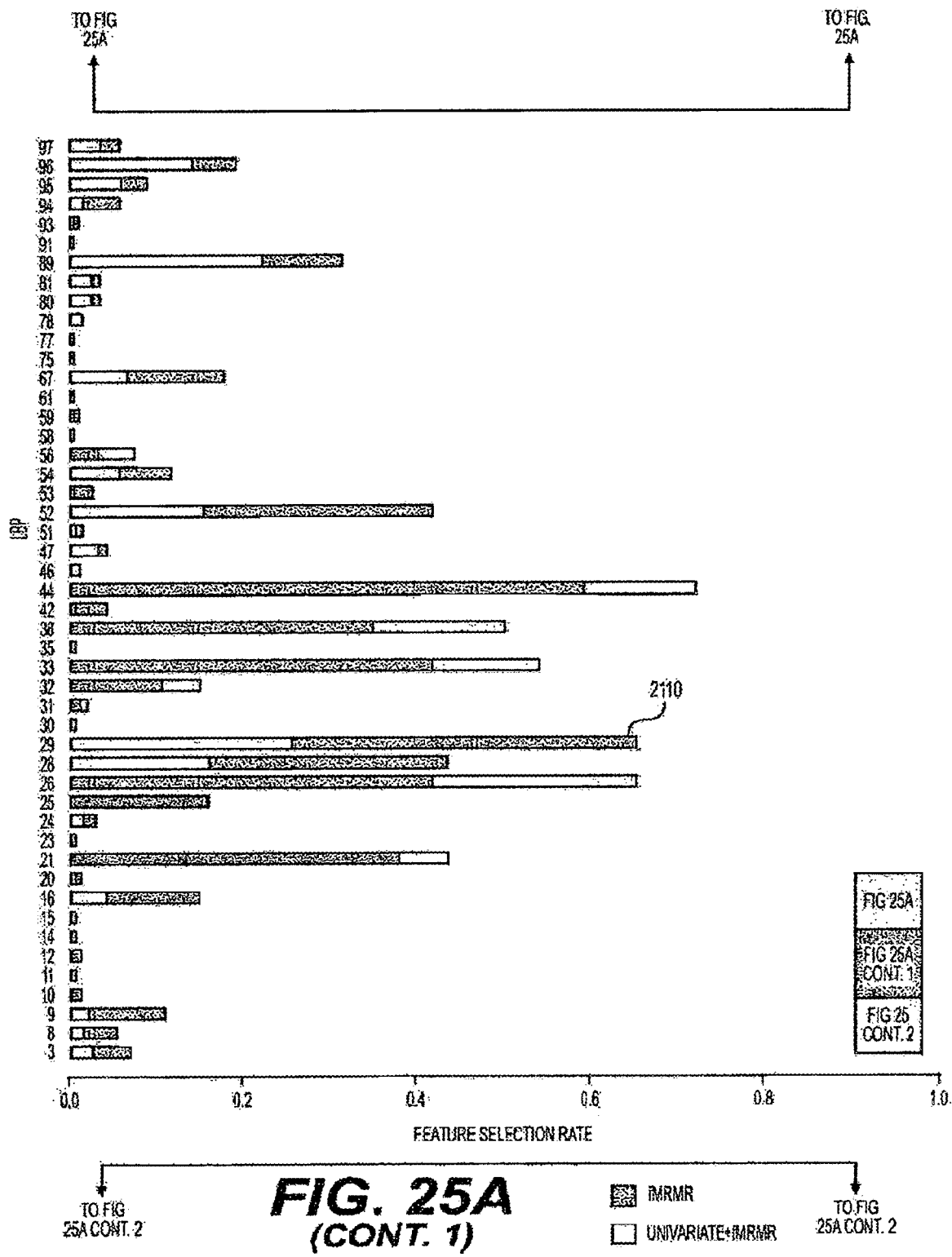
FIG. 25A (CONT. 1)

(CONT. 2)

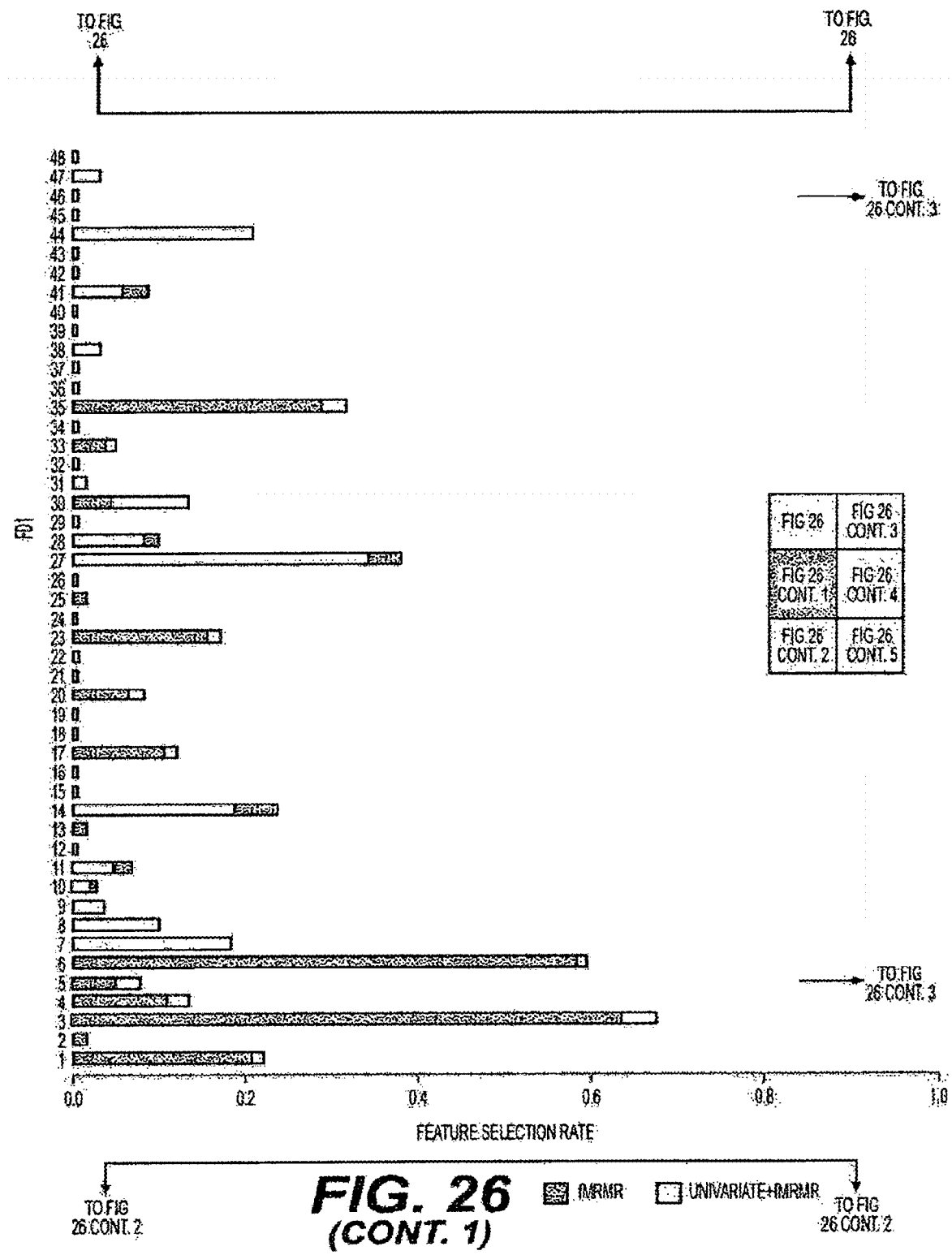
FIG. 26 (CONT. 1)

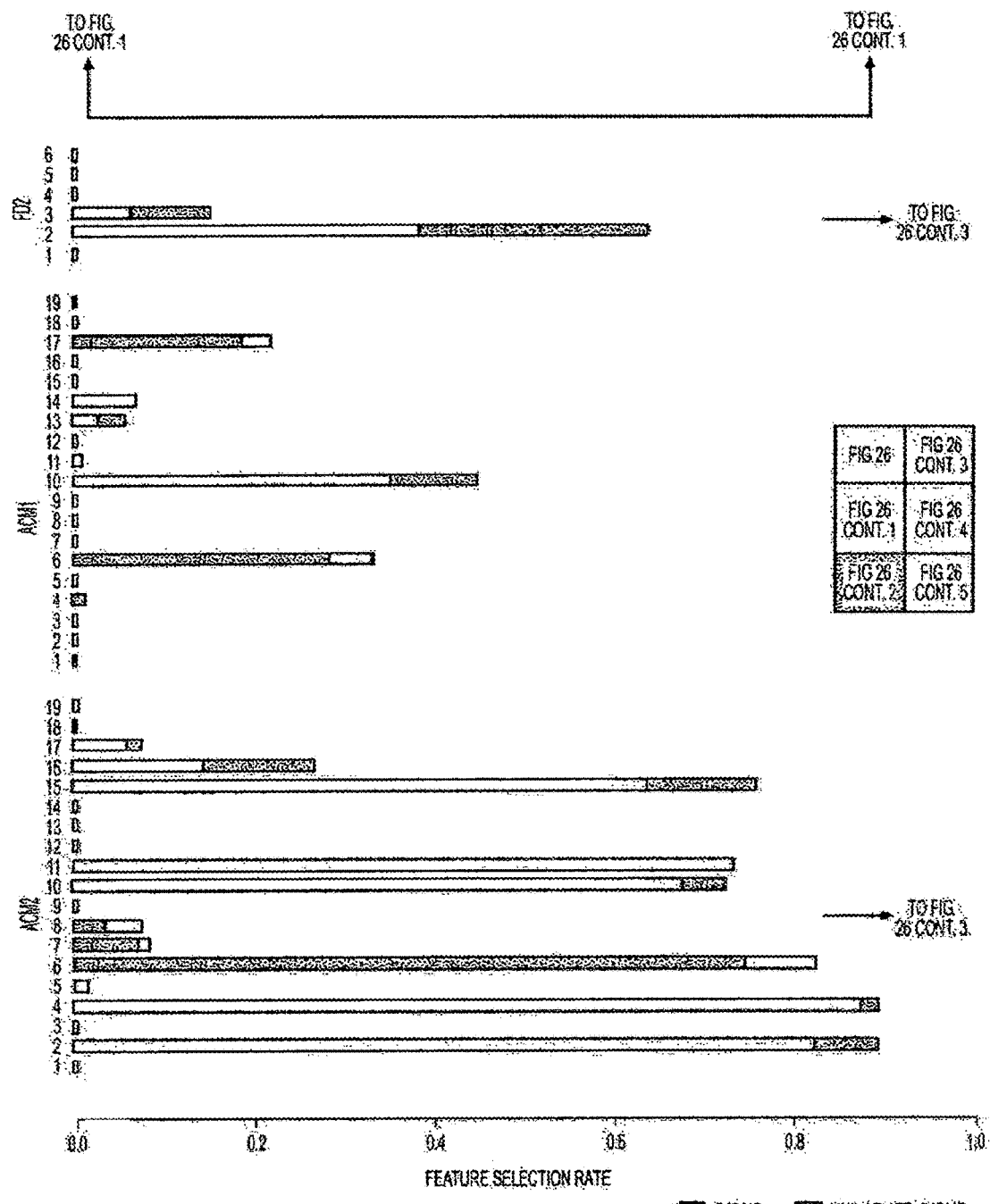
FIG. 26 (CONT. 2)

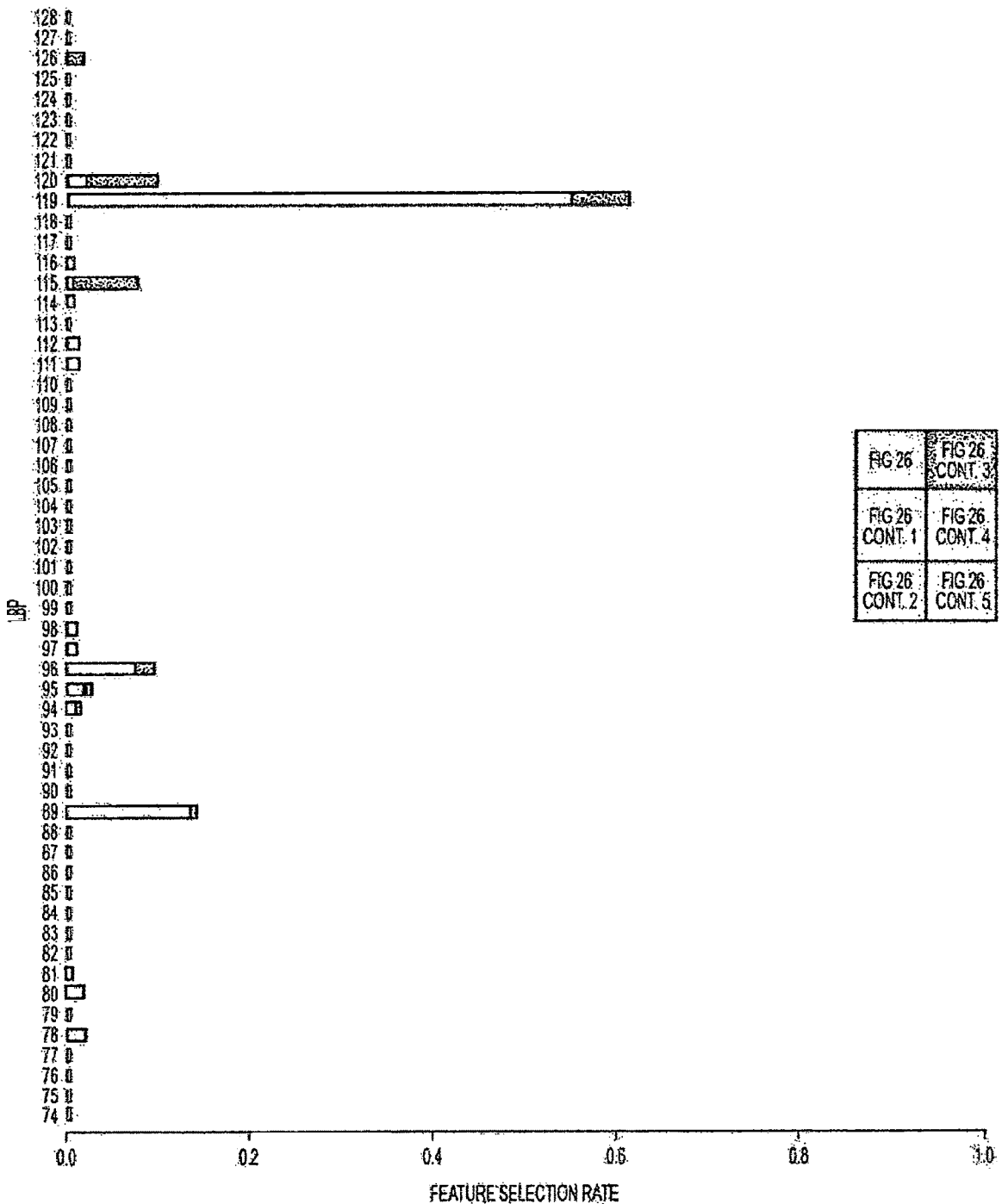
FIG. 26 (CONT. 3)

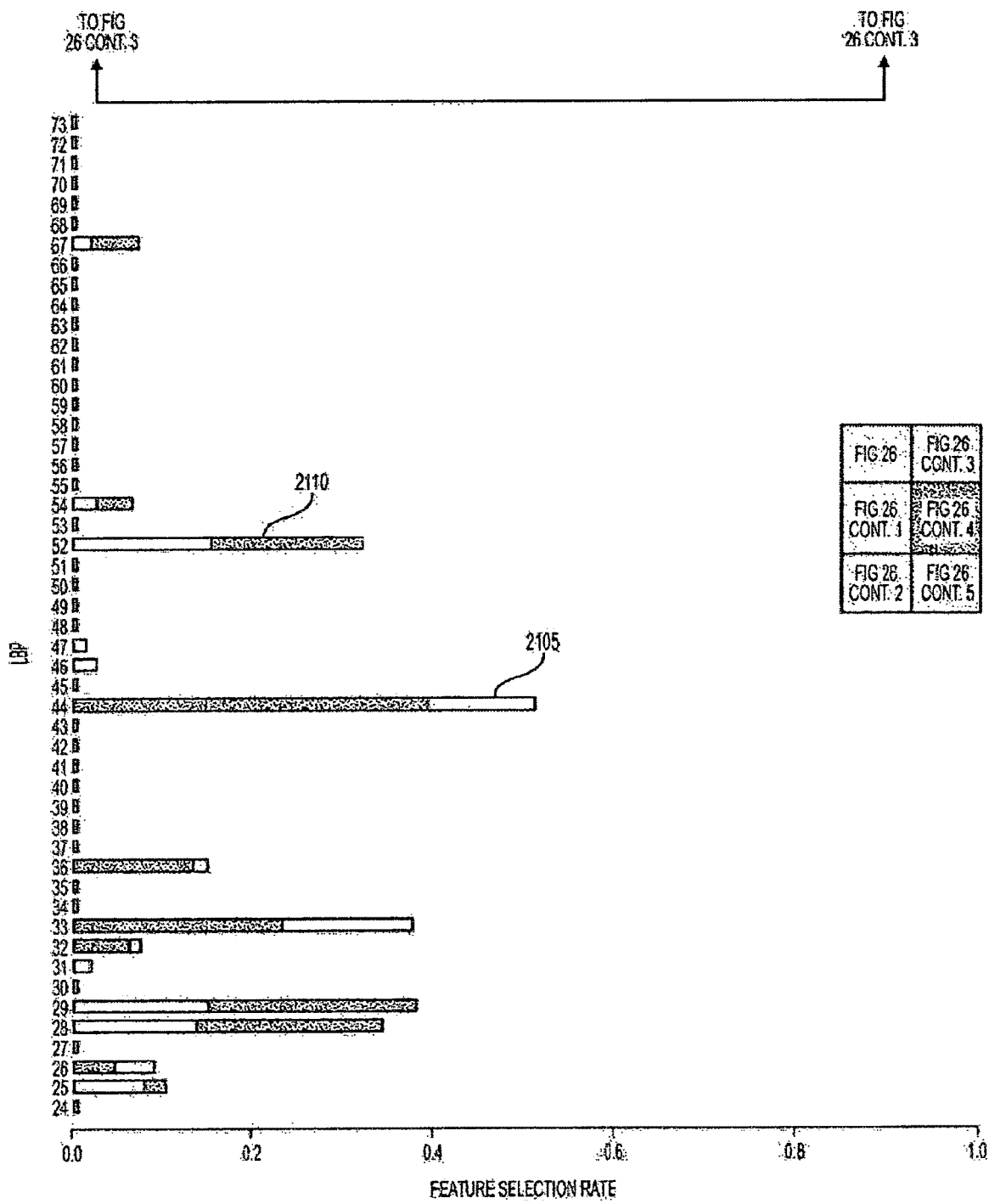
FIG. 26 (CONT. 4)

*(CONT. 5)*

SYSTEM, METHOD AND COMPUTER-ACCESSIBLE MEDIUM FOR TEXTURE ANALYSIS OF HEPATOPANCREATOBILIARY DISEASES

CROSS-REFERENCE TO RELATED APPLICATION(S)

This application relates to and claims the benefit and priority from International Patent Application PCT/US2016/034356 filed on. May 26, 2016 that published as International Patent Publication WO 2016/191567 on Dec. 1, 2016, which claims the benefit and priority from U.S. Patent Application No. 62/166,433, filed on May 26, 2015, the entire disclosures of which are incorporated herein by reference.

STATEMENT REGARDING FEDERALLY SPONSORED RESEARCH

This invention was made with government support under Grant No P30 CA008748 awarded by the National Institute of Health. The government has certain rights in the invention.

FIELD OF THE DISCLOSURE

The present disclosure relates generally to quantifying underlying pixel variation in imaging data, and more specifically, to exemplary embodiments of an exemplary system, method and computer-accessible medium for performing such analysis of computed tomography ("CT") images.

BACKGROUND INFORMATION

Hepatopanereatobiliary ("HPB") cancers are second among cancer related deaths. While overall survival rates have improved for most cancers, the five-year survival rate for patients with pancreas cancer is about 6%. Surgical candidates with HPB cancers routinely undergo preoperative imaging with CT. Imaging can be used to assess for metastatic disease, and to help determine resectability based on the burden of disease. Unfortunately, the vast majority of patients who ultimately undergo surgery with curative intent will eventually demonstrate recurrent tumor and possibly die from their disease. While CT can evaluate surgical resectability, the probability for a surgical cure or for intraoperative complications preoperatively, is not yet known.

HPB cancers display variable imaging appearances on CT. For pancreatic cancer in particular, they can range from homogeneous and isoattenuating masses to more heterogeneous hypoattenuating tumors encasing adjacent vessels, and can have features that may reflect tumor differentiation and tumor-stromal interactions. However, the dichotomy between isoattenuating or hypoattenuating tumors on CT does not capture the entire heterogeneity of tumors encountered clinically.

Imaging assessment by texture analysis is an emerging methodology to quantitatively assess differences in the border and heterogeneity of tumors and parenchyma, and has shown prognostic significance for breast, lung and colorectal cancers. However, the potential of texture analysis to be used on, for example, pancreatic cancer, has not been explored. Texture analysis ("TA") can characterize regions of interest in an image by spatial variations in pixel intensities. For example, a smooth or homogeneous image can lack pixel intensity variation and an irregular or heterogeneous image can have many pixel intensities and can be richly textured. In CT images, texture analysis has the potential to quantify regional variations in enhancement that cannot be qualified by inspection. Recent studies describe texture analysis to augment lesion diagnosis and characterization (see, e.g., Reference 1) to predict survival of colorectal cancer patients (see, e.g., References 2 and 3), and to classify hepatic tumors. (See, e.g., Reference 2). Texture analysis of liver parenchyma has been studied for fibrosis detection and correlated with postoperative pathologic findings. (See, e.g., References 4 and 5). However, texture analysis of CT images has not been used to stratify patients at risk during surgery or to predict treatment outcome.

For example in the liver, recurrences after resection of colorectal liver metastases ("CRLM") occur in up to 75% of patients. Preoperative prediction of hepatic recurrence has not been well studied but can be important as it can inform therapeutic strategies at the time of initial resection aimed at preventing recurrences. TA is an established procedure that quantifies pixel intensity variations (e.g., heterogeneity) on cross-sectional imaging. It is hypothesized that tumoral and parenchymal change predictive of hepatic recurrence in the future liver remnant ("FLR") can be detected using TA on preoperative CT images.

Approximately 140,000 new cases of colorectal cancer ("CRC") are diagnosed each year in the United States. (See, e.g., Reference 78). Nearly 25% of patients have CRLM at initial presentation and approximately 50 to 60% will ultimately develop metachronous CRLM. (See, e.g., Reference 79). In selected patients, hepatic resection can be the treatment of choice. Overall recurrence rates, however, can be as high as 75%. Most recurrences involve the liver and nearly one-third of these recurrences are confined to the liver. (See, e.g., References 80-82). Therefore, predicting, identifying and treating hepatic recurrence can be of critical importance.

To date, trials have not shown an overall survival benefit of perioperative systemic chemotherapy administered around the time of hepatic resection for CRLM. Adjuvant hepatic arterial infusion ("HAI") chemotherapy with combined floxuridine ("FUDR") and systemic 5-fluorouracil ("5-FU") has been associated with improved overall survivability ("OS") as compared to adjuvant 5-FU alone in a randomized trial. (See, e.g., References 83-85). Furthermore, adjuvant HAI with FUDR can be associated with a significant improvement in hepatic disease-free survival ("HDFS") after hepatic resection. (See, e.g., Reference 86). Thus, preoperative prediction of the risk of hepatic recurrence can identify ideal candidates for HAI. Although many prognostic models utilizing clinical and pathologic variables have been associated with survival and overall recurrence, no marker prognostic of hepatic recurrence has been established. (See, e.g., References 80 and 87-89).

It has been hypothesized that intrahepatic recurrence after liver resection can arise from occult liver metastases that can be present in the liver at the time of resection, but may not be detectable on conventional imaging. (See, e.g., References 90 and 91). Computer-based imaging analyses have the potential to detect visually occult, but clinically relevant changes in liver parenchymal enhancement. Texture features of liver parenchyma on CT imaging can potentially be altered by occult tumors, and can represent a surrogate for later recurrent disease. (See, e.g., References 92 and 93). Recently, a case-matched study showed that TA of preoperative CT was associated with the risk of post-hepatectomy liver insufficiency. (See, e.g., Reference 94). Additionally, it has been have reported that TA can classify pathologically confirmed chronic hepatitis-C activity and liver cirrhosis grades. (See, e.g., Reference 95). These findings provide preliminary evidence that TA can detect radiographically occult underlying microvascular and parenchymal variations in the liver that can, in turn, be related to the risk of hepatic recurrence after resection for CRLM.

TA can also play a role in the assessment of intratumoral heterogeneity, a feature of malignancy related to cell-density, necrosis, fibrosis and hemorrhage. Texture features from contrast-enhanced CT images were used to distinguish gastric cancer subtypes (see, e.g., Reference 96) and related to overall survival in primary colorectal cancer (see, e.g., Reference 97), hepatocellular carcinoma (see, e.g., Reference 98), and colorectal liver metastases. (See, e.g., References 99 and 100). In CRLM, whole tumor imaging morphology assessed by radiologists correlated to pathologic response and survival (see, e.g., Reference 101), suggesting a link between imaging, pathology and survival but this relationship is not well elucidated.

Thus, it may be beneficial to provide an exemplary system, method and computer-accessible medium which can overcome at least some of the deficiencies described herein above.

SUMMARY OF EXEMPLARY EMBODIMENTS

An exemplary system, method and computer-accessible medium for determining the pixel variation of a tissue(s) in an image(s) can be provided, which can include, for example, receiving first imaging information related to the image(s), segmenting a region(s) of interest from the image(s), generating second imaging information by subtracting a structure(s) from the region(s) of interest, and determining the pixel variation based on the second imaging information. The tissue(s) can include a liver and/or a pancreas. A characteristic(s) can be determined based on the pixel variation, which can include (i) a sufficiency of the tissue(s), (ii) a response to chemotherapy by the tissue(s), (iii) a recurrence of cancer in the tissue(s), or (iv) a measure of a genomic expression of the tissue(s).

In some exemplary embodiments of the present disclosure, the first imaging information can include a computed tomography image(s) of the tissue(s). The CT image(s) can be pre-processed to determine the region of interest(s). An image quality of an image of the tissue(s) associated with the first imaging information can be determined based on the pixel variation. The pixel variation using at a gray-level co-occurrence matrix(es) can be determined. A feature(s) of the tissue(s) can be extracted as further information based on the gray-level co-occurrence matrix(es). The feature(s) extracted by the computer arrangement can include (i) a contrast of an image of the tissue(s) or (ii) an entropy of the image of the tissue(s). The exemplary feature extracted(s) can include a quantitative predictor(s) of an outcome of a cancer treatment. The quantitative predictor(s) can include a survival rate(s) of a patient to whom the tissue(s) belongs and complications of the patient to whom the tissue(s) belongs. The GLCM can include at least four texture feature statistics, which can include (i) a contrast, (ii) a correlation, (iii) an energy and (iv) a homogeneity. Each texture feature statistic can be determined in at least four directions, which can include (i) 0°, (ii) 45°, (iii) 90° and (iv) 135°.

The region(s) of interest can include a tumor or a parenchyma. The structure(s) can include a bile duct(s) or a vessel(s). Third imaging information related to a volume(s) of the region(s) of interest can be generated based on the second information, where pixel values of the volume(s) can be expressed in Hounsfield units (HU). Fourth imaging information can be generated by removing pixels from the third imaging information that have a HU value in a particular range, which can be from about 0 HU to about 300 HU. The pixel variation can be determined based on the third imaging information. Additionally, the third imaging information can be scaled.

An exemplary system, method and computer-accessible medium for determining a characteristic(s) of a tissue(s) according to another exemplary embodiment of the present disclosure can be provided, which can include, for example, receiving information related to a texture analysis of the tissue(s), and determining the treatment characteristic(s) based on the information. The tissue(s) can include a liver and/or a pancreas. The characteristic(s) can include a sufficiency of the tissue(s). The information can include a computed tomography scan(s) of the tissue(s). A scan(s) of the tissues) can be controlled using a computed tomography scanning arrangement. The texture analysis can be performed using, for example, a gray-level co-occurrence matrix(s). A feature of the tissue(s) can be extracted based on a gray-level co-occurrence matrix, which can include a contrast of an image of the tissue(s) or entropy of the image of the tissue(s).

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIGS. 19A-19B are exemplary images of CT slices used by the exemplary system, method and computer-accessible medium according to an exemplary embodiment of the present disclosure;

Figure 1:
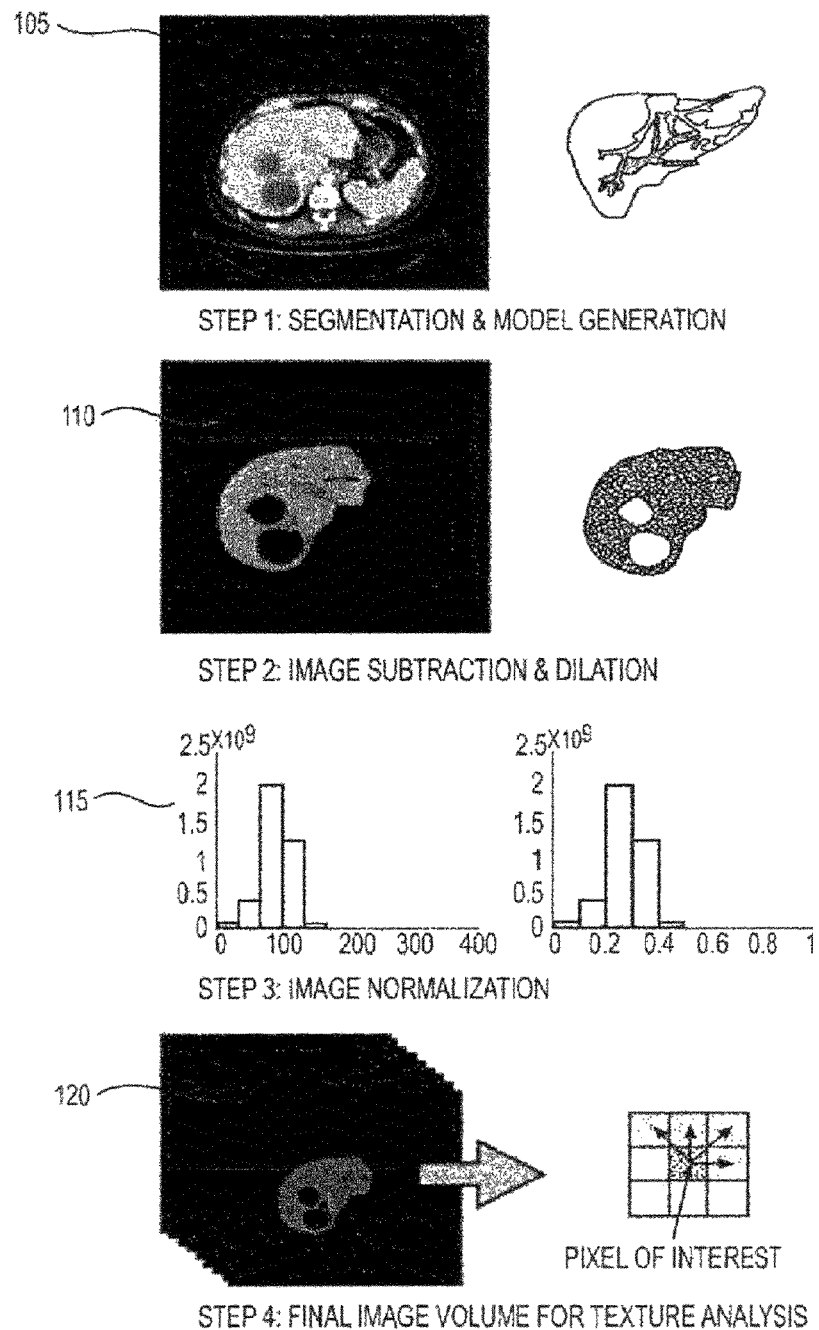
FIG. 1 is an exemplary flow diagram of steps/procedures implemented by an exemplary texture analysis method according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

Radiomics is the extraction of imaging features from medical images. These exemplary features can provide quantitative predictors of outcomes from cancer treatments, including survival and complications. Currently, radiographic interpretation for cancer care is qualitative, guided by the experience of the radiologist reading the medical images. In contrast, quantitative analysis of medical images using the exemplary system, method and computer-accessible medium can quantify regional variations in enhancement that cannot be qualified by inspection by a radiologist. Quantifying tumor imaging heterogeneity has the potential to illustrate heterogeneity at the genetic and histopathological level that can guide prognosis, potentially due to aggressive biology or treatment resistance.

Radiogenomics is an emerging field focusing on establishing relationships between imaging features and molecular markers. Advances in radiogenomics can be beneficial in clinical decision making through development of predictive and prognostic treatment procedures and noninvasive disease surveillance. This can be advantageous as compared to current biopsy procedures. For example, current biopsy procedures use invasive tissue procurement procedures that lack temporal and spatial dimensions, as they provide information in a single time point, typically from a single anatomical site. In contrast, the exemplary system, method and computer-accessible medium, according to an exemplary embodiment of the present disclosure, can utilize multiple time points and multiple tumor sites.

Figure 7:
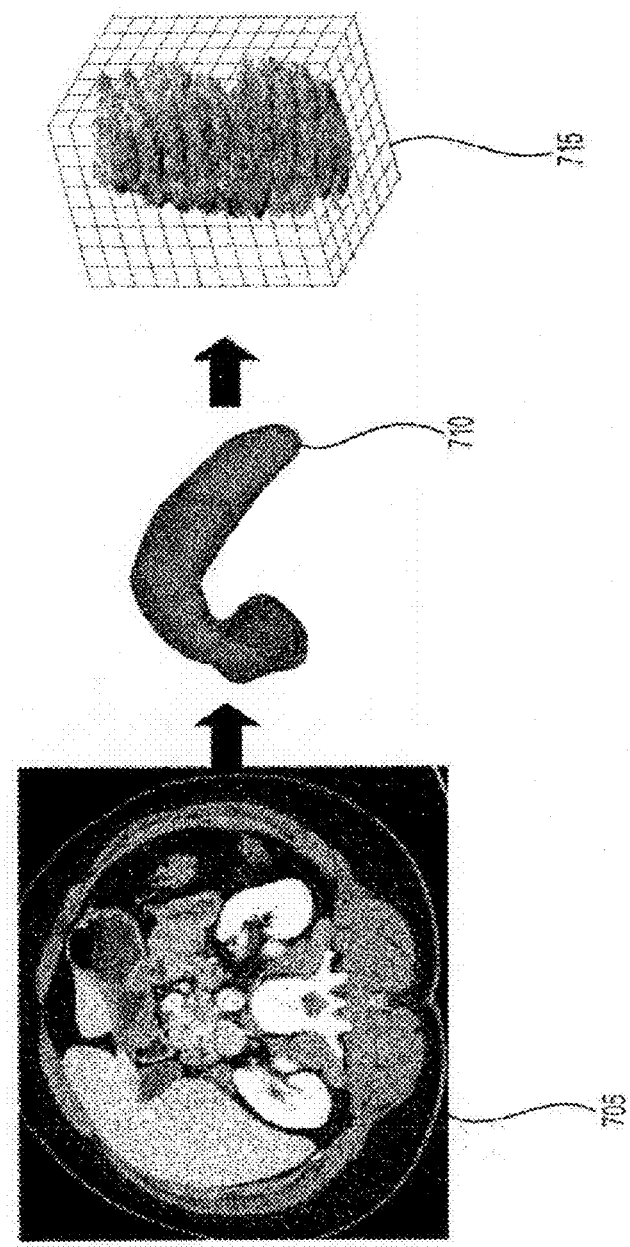
FIG. 7 is a set of images illustrating image extraction according to an exemplary embodiment of the present disclosure.

The exemplary system, method and computer-accessible medium, according to an exemplary embodiment of the present disclosure, can utilize the identification of a region of interest from the medical image. Pre-processing of a CT images can be performed to define the tumor or parenchymal region for further analysis. The region can be automatically or semi-automatically segmented from neighboring structures using, for example, Scout Liver (e.g., Pathfinder Technologies Inc., Nashville, Tenn.). (See, e.g., FIG. 7). 3D models of the tumors, bile ducts and vessels generated can be subtracted from the segmented tumor, or parenchyma, to generate a volume of the region of interest with pixel values which can be expressed in Hounsfield units ("HU"). Attenuation values outside of, for example, about 0 HU and about 300 HU (e.g., corresponding to regions, such as bulk fat and metal) can be removed from the exemplary scans and can be excluded from analysis. The remaining region of interest can be scaled using, for example, image normalization, which can compensate for potential irregularities in the scale of pixel values across image volumes, while also maintaining the overall shape of the image histogram and visual appearance of individual volumes. FIG. 7 shows a diagram of an exemplary image processing pipeline. For example, as shown therein, the pancreas and tumor can be segmented from the scan (e.g., element 705), the tumor and pancreas regions can be extracted (e.g., element 710), and texture features can be generated based on the extraction region (e.g., element 715).

Second order texture statistics can be implemented to examine the spatial relationship of neighboring pixels. Unlike first-order statistics that calculate cumulative statistics on individual pixel values, second-order statistics can evaluate the likelihood of observing spatially correlated pixels. A pixel neighborhood can be chosen to assess this spatial relationship because this size can demonstrate excellent discriminatory power in preliminary analyses. A gray-level co-occurrence matrices ("GLCM") can be constructed to represent spatial relationships in the pixel neighborhoods using a standard implementation in the Image Processing Toolbox in MATLAB (e.g., MathWorks, Natick, Mass.). Four GLCM-based texture feature statistics can be used, which can include, for example: (i) contrast (e.g., local variation in the image), (ii) correlation (e.g., gray-level interdependence of brightness), (iii) energy (e.g., local homogeneity), and (iv) homogeneity (e.g., high values indicate constant image). Each can be computed in four directions from 0°, 45°, 90° and 135°. Values can be averaged over the four directions since the statistics can be directionally invariant. Values can be computed for each CT slice, and can be averaged over the whole tumor volume. A fifth texture statistic, image entropy (e.g., measure of randomness in brightness variation) can be computed for the entire region of interest. The exemplary system, method and computer-accessible medium, according to an exemplary embodiment of the present disclosure, can define a quantitative imaging phenotype as either a single or combination of texture features, which can measure heterogeneity by pixel variation.

The exemplary system, method and computer-accessible medium, according to an exemplary embodiment of the present disclosure can be used, for example, to predict a response to chemotherapy. Thus, the exemplary system, method and computer-accessible medium, according to an exemplary embodiment of the present disclosure, can be used to guide treatment strategy. Additionally, pre and post medical images can provide measurement of response to chemotherapy.

The exemplary system, method and computer-accessible medium, according to an exemplary embodiment of the present disclosure, can also be used to predict cancer recurrence in the liver. Preoperative images of the liver parenchyma, with vessels and tumors removed, can be used to determine which patients are at high risk for recurrence of their disease.

Partial hepatectomy is one of the most effective and only potentially curative treatment for selected primary and secondary hepatic tumors. Despite significant improvements in perioperative outcomes, postoperative liver insufficiency remains a source of morbidity and mortality, particularly for major resections. (See, e.g., References 6 and 7). Complication rates can increase directly with the extent of the resection, with reports of a 30% rate of severe hepatic insufficiency when 5 or more segments can be resected. (See, e.g., Reference 8). Because a postoperative hepatic insufficiency can delay chemotherapy, prolonged hospital stays can increase an overall risk of cancer recurrence. Thus, it can be important to identify patients at risk before surgery.

Several studies have shown that the percentage of functional liver parenchyma remaining after surgery can predict postoperative hepatic insufficiency (see, e.g., References 8-10), and the functional capacity of the parenchyma. Passive function tests such as biochemical parameters (e.g., bilirubin, albumin and coagulation factor synthesis), and clinical grading systems (e.g., Child-Pugh and Model for End-Stage Liver Disease ("MELD")), while capable of identifying severe hepatic parenchymal disease, may not be useful predictors of perioperative outcomes in candidates for resection. (See, e.g., Reference 11). Dynamic quantitative liver function tests, such as, for example, indocyanine green clearance and galactose elimination capacity, can be more reliable because the elimination/metabolization of these substances can occur almost exclusively in the liver; however, several studies of these tests have shown no significant correlation with clinical outcomes and histologic results. (See, e.g., References 12 and 13). Cross-sectional imaging studies can typically be used to assess liver volumetry, and to detect steatosis or cirrhosis, but few metrics exist for quantifying liver functional capacity from images. (See, e.g., Reference 14). Recently, gadoxetic acid uptake in magnetic-resonance ("MR") imaging has shown promise for assessment of liver insufficiency by identifying 3 patients with liver insufficiency out of 73 who underwent liver resection. (See, e.g., Reference 15). Reliable prediction of postoperative liver insufficiency therefore remains a difficult, inexact practice.

Exemplary Patient Selection

A case-matched study design was used to eliminate possible confounding effects of clinically established factors associated with postoperative hepatic insufficiency. Comparisons were performed between the patients who underwent major hepatic resection with postoperative liver insufficiency complications and a matched group of patients with no postoperative liver insufficiency. Patients were matched 2:1 by procedure (e.g., right lobectomy or right trisegmentectomy), remnant liver volume ("RLV"), which can be the ratio of the remaining functional liver volume to the preoperative functional liver volume, expressed as a percentage and year of procedure.

Exemplary Postoperative Liver Dysfunction and Failure Classification

Patients with postoperative liver insufficiency were identified. Postoperative liver insufficiency was defined as the presence of the following: (i) total bilirubin greater than 4.1 mg/dL without obstruction or bile leak, (ii) international normalized ratio ("INR")>2.5, (iii) ascites (e.g., drainage >500 mL/day), and/or (iv) encephalopathy with hyperbilirubinemia. The severity of liver insufficiency was assessed using the surgical events database scale. (See, e.g., Reference 16).

Exemplary Postoperative Staging and Follow-Up

Steatosis was graded in the course of routine histopathologic assessment based on the Kleiner-Brunt histologic scoring system: mild (e.g., <33% of hepatocytes affected), moderate (e.g., 33% to 66% of hepatocytes affected), or severe (e.g., >66% of hepatocytes affected). (See, e.g., Reference 17). Fibrosis was graded based on the Rubbia-Brandt classification. (See, e.g., Reference 18).

Exemplary CT Images

Patients with conventional portal venous phase contrast-enhanced CT imaging before surgery were included. Postcontrast CT images were obtained after the administration of about 150 mL of iodinated contrast (e.g., Omnipaque 300, GE Healthcare) at about 2.5 mL/s on multidetector CT (e.g., Lightspeed 16 and VCT, GE Healthcare), as a standard imaging protocol. The following scan parameters were used: pitch/table speed 0.984-1.375/39.37-27.5 mm; autoMA 220-380; noise index about 12-14; rotation time about 0.7-0.8 ms; scan delay about 80 s. Axial slices reconstructed at each 5-mm interval were used for the analysis. The entire liver was scanned on each CT.

Exemplary Image Processing

Standard image processing procedures were used to extract the liver parenchyma from surrounding structures. (See, e.g., FIG. 1). Liver, tumors, vessels and bile ducts were semi-automatically segmented from CT scans using Scout Liver (e.g., Pathfinder Technologies Inc.). (See, e.g., procedure 105). The remainder of the image processing was fully automated with custom software. Parenchyma was separated from other structures using image subtraction, (e.g., procedure 110), attenuation values outside of 0 and 300 threshold HU (e.g., corresponding to non-parenchymal regions, such as bulk fat and metal) were removed using image thresholding and image dilation and erosion operators slightly expanded the tumor and vessel boundaries to compensate for potential small inaccuracies in the segmentation. The final volume was scaled using conventional image normalization (e.g., procedure 115), which can compensate for potential irregularities in the scale of pixel values across image volumes while conserving the appearance of the image. (See, e.g., Reference 19). The final image volume for texture analysis was produced at procedure 120.

Exemplary Texture Analysis

An exemplary texture analysis procedure was performed to characterize the statistical variation in the spatial relationships of pixels in parenchymal regions using standard GLCMs. (See, e.g., References 20-22). The GLCM can represent the number of neighboring pixel brightness values (e.g., gray levels) at specified distances in the image. Once the GLCM can be constructed, standard features can be extracted using well-defined statistics. Five statistics were used: (i) contrast (e.g., local variation), (ii) correlation (e.g., brightness interdependence on neighboring pixels), (iii) energy (e.g., local homogeneity), (iv) entropy (e.g., randomness in brightness variation), and (v) homogeneity.

Exemplary Statistical Analysis

Clinical variables were expressed as a mean (e.g., with standard deviation) or a median (e.g., with range). Texture features were expressed as a mean (e.g., with 95% confidence interval). Differences between the matched groups with respect to the clinical variables and texture features were determined using Wilcoxon's signed rank test for continuous variables and Pearson's chi-square test for categorical variables, where $p<0.05$ defined the statistical significance. All statistical analyses were performed with SPSS version 21 (e.g., IBM Corporation). The percentage difference between the texture features in the liver insufficiency ("LI") and no liver insufficiency ("NLI") study groups was expressed as % difference ¼ (e.g., mean Liemean NLI)× (100/mean NLI) to show the relative differences between the 2 groups.

Exemplary Results

Exemplary Demographics

Figure 2:
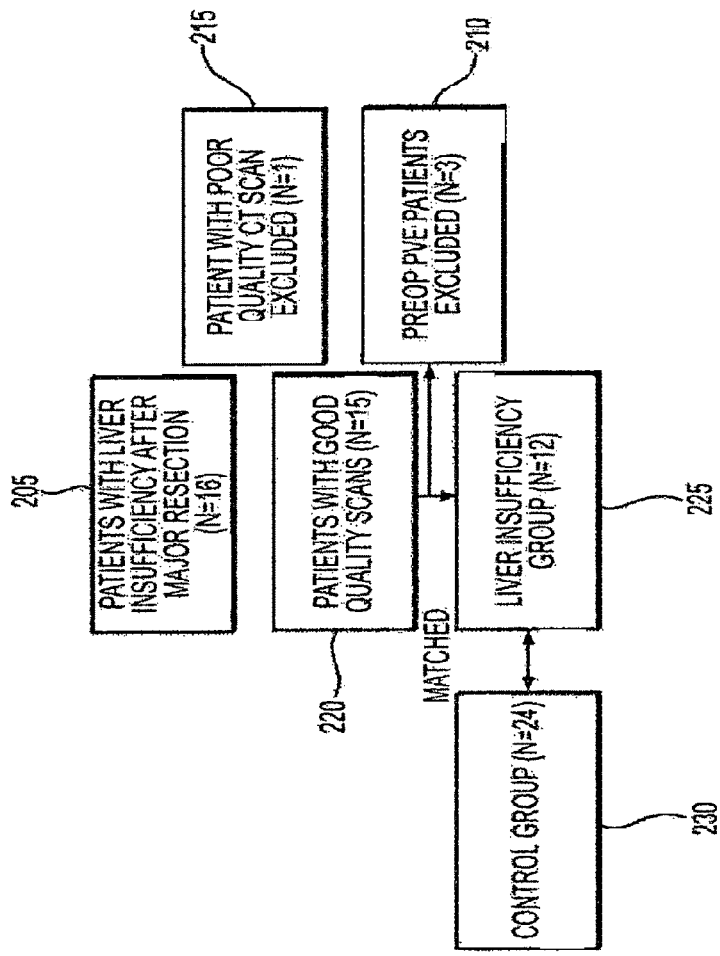
FIG. 2 is an exemplary flow diagram of a procedure for generating a study profile for a patient selection according to an exemplary embodiment of the present disclosure.

An inclusion/exclusion diagram is shown in FIG. 2. For example, as shown therein sixteen patients with liver insufficiency (e.g., element 205) after major hepatic resection from January 2006 to January 2012 were identified from the liver resection patient database of 1,721 resections (e.g., 0.9%) and 467 major resections (e.g., 3.4%). Three patients underwent preoperative portal vein embolization (e.g., element 210) and were excluded due to the potential confounding influence of embolization-induced parenchymal changes on texture analysis. One additional patient was excluded based on a poor quality scan (see, e.g., element 215); leaving 15 patients with good quality scans. (See, e.g., element 220). All patients had undergone routine portal venous phase contrast-enhanced CT before surgery. The remaining 12 patients (e.g., element 225) were matched to a control group of 24 patients (e.g., element 230), for a total cohort of 36 patients.

Patient demographics and clinicopathologic factors are presented in Table 1 below. Comparisons were made between the LI and the NLI groups to reveal potential biases in the study group selection. The median age, weight, height, and body mass index did not significantly differ between the two groups; however, patients in the LI group were more likely to be male (e.g., 92%, $p<0.05$) with slightly larger body surface area (e.g., LI: 2.0 m2 vs NLI: 1.8 m2, $p<0.05$). Preoperative bilirubin level, history of preoperative chemotherapy, and type of chemotherapy did not significantly differ between groups. The extent of resection did not significantly differ between the two groups. Half of patients in each group underwent right hepatectomy and the other half underwent extended right hepatectomy, with mean RLV of 37.1% in the LI group vs 41.5% in the NLI group (e.g., p ¼ 0.517).

TABLE 1

Demographic and Clinicopathologic Factors

| Variable | All patients (n = 36) | NLI (n = 24) | LI (n = 12) | p Value |
|---|---|---|---|---|
| Age, y (range) | 63 (54-73) | 62 (53-73) | 66 (56-75) | — |
| Sex, n (%) | | | | <0.05 |
| Male | 21 (58) | 10 (42) | 11 (92) | — |
| Female | 15 (42) | 14 (58) | 1 (8) | — |
| Weight, kg (range) | 80 (63-98) | 70 (61-92) | 92 (77-99) | — |
| Body mass index, kg/m$^2$ (range) | 27.9 (23.1-31.2) | 26.7 (22.2-30.1) | 29.6 (26.3-32.4) | — |
| Preoperative bilirubin, mg/dL (mean ± SD) | 0.8 ± 0.6 | 0.7 ± 0.5 | 1.0 ± 0.6 | — |
| Preoperative chemotherapy, n (%) | 17 (47) | 13 (54) | 4 (33) | — |
| Type of preoperative chemotherapy, n (%) | | | | |
| FOLFOX | 7 (19) | 6 (25) | 1 (8) | — |
| FUDR/irinotecan | 2 (6) | 1 (4) | 1 (8) | — |
| Irinotecan | 1 (3) | — | 1 (8) | — |
| Bleomycin/etoposide/cisplatin | 1 (3) | 1 (4) | — | — |
| Cisplatin/gemcitabine | 1 (3) | — | 1 (8) | — |
| Taxotere/Herceptin (Genentech) | 1 (3) | 1 (4) | — | — |
| Irinotecan/cetuximab | 1 (3) | 1 (4) | — | — |
| Gemcitabine/Taxotere (Sanofi); doxorubicin/dacarbazine | 1 (3) | 1 (4) | — | — |
| Procedure, n (%) | | | | |
| Right lobectomy | 18 (50) | 12 (50) | 6 (50) | — |
| Right trisegmentectomy | 18 (50) | 12 (50) | 6 (50) | — |
| RLV (%), mean ± SD | 40.1 ± 13.7 | 41.5 ± 14.1 | 37.1 ± 13.1 | — |
| Mortality, n (%) | 6 (17) | — | 6 (50) | <0.01 |
| Major complications, n (%) | 14 (39) | 6 (25) | 8 (67) | — |
| Margin status, n (%) | | | | |
| Negative | 35 (97) | 24 (100) | 11 (92) | — |
| Positive | 1 (3) | — | 1 (8) | — |
| Diagnosis, n (%) | | | | |
| Colorectal cancer | 20 (56) | 11 (46) | 9 (75) | — |
| Cholangiocarcinoma | 10 (28) | 7 (29) | 3 (25) | — |
| Hepatocellular carcinoma | 3 (8) | 3 (13) | — | — |
| Other disease* | 3 (8) | 3 (13) | — | — |
| Steatosis, n (%) | 18 (50) | 12 (50) | 6 (50) | — |
| Fibrosis, n (%) | 4 (11) | 2 (8) | 2 (17) | — |

*Testicular, breast, and duodenal.
FOLFOX, oxaliplatin, fluorouracil (5FU), and folinic acid; FUDR, florodeoxyuridine LI, liver insufficiency; NLI, no liver insufficiency; RLV, remnant liver volume.

Major complications (e.g., less than or equal to grade 3) were observed in 14 patients, for an overall complication rate of 39%, with no differences between the two groups. However, the 90-day mortality rate was significantly higher in the LI group (e.g., 50%, n ¼ 6) (e.g., p<0.01).

Pathologic characteristics were not statistically different between the two groups. Overall, the majority of patients were diagnosed with metastatic colorectal cancer (e.g., 56%, n ¼ 20), followed by cholangiocarcinoma (e.g., 28%, n ¼ 10), hepatocellular carcinoma (e.g., 8%, n ¼ 3), and other metastatic disease (e.g., testicular [3%, n ¼ 1], breast [3%, n ¼ 1], duodenal [3%, n ¼ 1]). Postoperative margin status was negative in all but 1 patient.

Exemplary Texture

Two texture features in the control group (e.g., n ¼ 24) were significantly different (e.g., p<0.05) from those in the LI group (e.g., n ¼ 12). As compared with features in the control group, the contrast and entropy features increased in the patients with liver insufficiency; the correlation, energy and homogeneity features decreased in value (see, e.g., Table 2 below). Contrast, a measure of local variation in the image, showed greater range in values in the LI group than in the control group. A correlation can be a measure of the linear dependency of gray levels on neighboring pixels, with higher values indicating greater similarity in gray-level regions. The control group had much less variation than the LI group (e.g., p<0.05). Entropy, a measure of randomness in brightness variation, was greater in the LI group (e.g., p<0.05). Homogeneity was somewhat lower in the LI group, but this difference was not statistically significant.

TABLE 2

Comparison of CT Texture Features for Patients with No Postoperative Liver Insufficiency and Patients with Liver Insufficiency

| Texture feature | NLI (n = 24), mean (95% CI) | LI (n = 12), mean (95% CI) | % Difference | p Value |
|---|---|---|---|---|
| Contrast | 0.65 (0.47, 0.82) | 0.97 (0.54, 1.40) | 49 | 0.098 |
| Correlation | 0.04 (0.03, 0.05) | 0.02 (0.00, 0.03) | -50 | <0.05* |
| Energy | 0.40 (0.27, 0.53) | 0.37 (0.12, 0.62) | -8 | 0.106 |
| Entropy | 0.50 (0.45, 0.55) | 0.58 (0.51, 0.65) | 16 | <0.05* |
| Homogeneity | 0.79 (0.74, 0.83) | 0.75 (0.64, 0.85) | -5 | 0.091 |

% Difference = (mean LI − mean NLI) × (100/mean NLI).
*Significant.
LI, liver insuffucuency; NLI, no liver insufficiency.

Figure 3A:
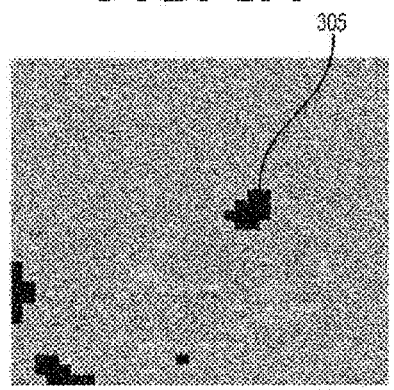
FIGS. 3A and 3B are exemplary images taken using the exemplary system, method and computer accessible medium according to an exemplary embodiment of the present disclosure.
Figure 3B:
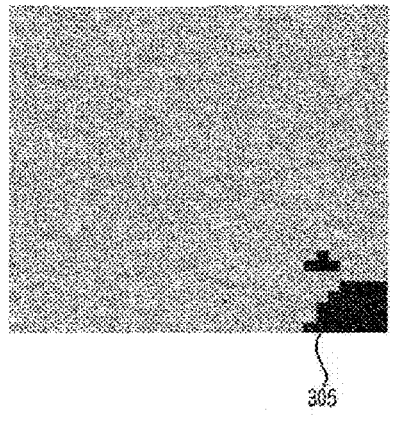

The texture of the liver parenchyma from preoperative CT images of patients with postoperative liver insufficiency was significantly more varied and less homogeneous than that of the control group. (See, e.g., FIGS. 3A and 3B). For example, FIG. 3A illustrates a comparison of 32 by 32 preoperative CT textures with a pixel distance of 24 for patients with no postoperative live insufficiency. FIG. 3B illustrates a comparison of 32 by 32 preoperative CT textures with a pixel distance of 24 for patients with postoperative liver insufficiency. Areas 305 indicate non-parenchymal regions (e.g., vessels, tumors and/or cysts) that can be excluded from analysis.

Exemplary Discussion

Partial hepatic resection can be considered an effective and relatively safe procedure for carefully selected patients. Over the last two decades, increased use of parenchymal-sparing procedures in resection has reduced perioperative morbidity and mortality. (See, e.g., Reference 7). However, a postoperative liver insufficiency remains a grave concern because up to 75% of postoperative mortalities can be related to postoperative liver insufficiency. (See, e.g., Reference 23). In addition to human factors, one study reported a three-fold increase in the total costs associated with the clinical management of postoperative liver failure patients. (See, e.g., Reference 24). Preventing liver insufficiency can be an important in liver surgery because treatment options for this condition can be limited, and associated mortality rates can be high; however, one objective measure of parenchymal quality can be difficult to obtain.

Preoperative CT texture of liver parenchyma of patients who experience liver insufficiency postoperatively can differ significantly from the preoperative CT texture of patients who do not. Preoperative patient characteristics can be similar; highlighting the potential role of texture analysis to stratify risk groups before surgery. Although the basic definition of postoperative liver insufficiency can be contested (see, e.g., Reference 23), six of twelve patients (e.g., 50%) in the LI group died within ninety days of surgery. These six patients developed liver insufficiency as the initial event in the cascade of events that ultimately led to their deaths. Therefore, the exemplary system, method and computer-accessible medium clearly identified the population at high risk for poor perioperative outcomes.

Textural differences between livers of patients with and without insufficiency can arise from a combination of factors beyond intrinsic liver parenchymal properties. An exemplary limitation of using routine portal venous phase CT for liver texture analysis can be the arbitrary and fixed time point at which these abdominal CTs can be performed. A fixed delay of eighty seconds can be used for the portal venous phase, but certain patient variables can affect the degree of liver parenchymal enhancement, such as cardiac output or hepatic venous congestion. Normalizing the histogram of pixel intensities before performing texture analysis can reduce the effect of differences in the magnitude of liver enhancement given a fixed dose of contrast, but may not eliminate the textural differences due to extrahepatic patient factors. Thus, the exemplary system, method and computer-accessible medium, according to an exemplary embodiment of the present disclosure, can facilitate analyses at multiple time points after contrast injection can help define an optimal time point to distinguish between patients with high or low risk for postoperative liver insufficiency by parenchymal texture analysis.

CT images were quantified using texture analysis with exemplary GLCM methods. An exemplary texture analysis with GLCM can be well defined, and has been studied for many years, with numerous applications supporting its use. (See, e.g., References 19 and 23). Various studies have shown this method to correspond to some level of human perception. (See, e.g., Reference 25). Additionally, GLCM continues to outperform other methods of texture classification. (See, e.g., Reference 26). These quantitative imaging features have been shown to improve tumor diagnosis (see, e.g., References 1 and 27), and to provide measures of response assessment (see, e.g., References 28 and 29) and radiation-induced gland injury (see, e.g., Reference 30), and can be reproducible across multiple imaging units. (See, e.g., Reference 31). Additionally, recent investigations have shown that CT texture can relate to fibrosis staging (see, e.g., References 4 and 5), so the extension to liver insufficiency may not be unexpected.

The exemplary system, method and computer-accessible medium, according to an exemplary embodiment of the present disclosure, can differ from prior hepatic texture analysis procedures. For example, instead of the exemplary GLCM methods used according to exemplary embodiments of the present disclosure, many studies used edge detection procedures (see, e.g., References 2 and 3), which rely on the analysis of abrupt brightness changes rather than on statistical variation of brightness in a neighborhood. Brightness variation in liver parenchymal regions on CT can represent subtle changes in uptake of intravenous contrast. Analysis of brightness variation can provide a better assessment of underlying parenchymal health. In contrast, edge detection procedures can be more suitable for tumor detection. Non-parenchymal regions (e.g., vessels, cysts, etc.) were excluded from analysis: including these high-contrast regions could potentially bias measurement of brightness variation. For example, contrast-to-noise ratios calculated between the most hyper- and hypo-intense regions of the liver have been correlated with fibrosis. (See, e.g., Reference 32).

Analysis of patient and treatment factors determined that only exemplary texture features appear to predict liver insufficiency in this cohort. Other studies of hepatic texture do not report analysis of these patient and treatment factors (see, e.g., References 2 and 3) that can represent surrogates of hepatic texture values. The ability to predict hepatic behavior before treatment has the potential to inform risk stratification for patients under consideration for resection, and to assess the risk of liver injury in patients undergoing initial treatment with chemotherapy. Although new imaging protocols and contrast agents are in development, CT remains the primary imaging modality for oncology patients, and CT images can be potentially rich with additional useful information beyond anatomic data.

The exemplary system, method and computer-accessible medium, according to an exemplary embodiment of the present disclosure, can facilitate a quantitative approach to measuring the heterogeneity of liver parenchymal enhancement. Differences in parenchymal heterogeneity can be a reflection of the variability in the distribution of intravenously administered contrast. This variability can reflect a combination of factors; including changes to the microvasculature that can often occur from the presence of metastatic disease as well as the chemotherapy used to treat it. Because the exemplary two patient groups did not substantially differ in type of malignancies or chemotherapies used, the exemplary texture analysis can reflect the accumulated microvascular injury, not appreciated on routine histology, but possibly associated with high risk of liver insufficiency after resection.

The increasing use of preoperative chemotherapy suggests that posthepatectomy liver insufficiency will likely remain a major problem. In tumor types with higher risk of liver insufficiency, such as hilar cholangiocarcinoma (see, e.g., Reference 33), the exemplary system, method, and computer-accessible medium can show much broader applicability in a larger prospective study.

Exemplary Radiogenomics in Cholangiocarcinoma: Molecular Profiling by Imaging Phenotypes Exemplary Hypoxia Markers and Immunohistochemistry Molecular profiling of tumors was based on immunohistochemistry studies targeting the following established hypoxia markers (see, e.g., Table 3): VEGF (see, e.g., Reference 34), EGFR (see, e.g., Reference 34), MRP-1 (see, e.g., Reference 35), HIF-1α (see, e.g., Reference 34), CA-IX (see; e.g., Reference 36), CD24 (see, e.g., Reference 37), GLUT1 (see, e.g., Reference 38), P53 (see, e.g., Reference 39), and MDM2 (see, e.g., Reference 40). The details of the primary antibodies have been previously reported. (See, e.g., References 41-43). All immunostains were evaluated without any knowledge of the clinical findings by a dedicated liver pathologist. Stains were graded according to the percentage of positive tumor cells. For HIF-1α and CA IX, positive staining benefits from positive nuclear labeling in >about 5% of tumor cells, and for VEGF, EGFR, P53, MDM2, CD24, MRP-1, and GLUT1, positive staining refers to cytoplasmic and/or membranous labeling in >10% cells.

neighboring structures using Scout Liver (e.g., Pathfinder Technologies Inc., Nashville, Tenn.). (See, e.g., Reference 44). Underlying pixel variations in the tumor volume were quantified using an exemplary image processing and texture analysis procedure. Three-dimensional models of the tumors, bile ducts and vessels generated by the Scout software were subtracted from the segmented tumor to generate a CT volume of the tumor region with pixel values expressed in HU. Attenuation values outside of 0 and 300 HU (e.g., corresponding to non-tumoral regions, such as bulk fat and metal) were removed from the scans and excluded from analysis. The segmented tumor was scaled using an image normalization procedure, which can compensate for potential irregularities in the scale of pixel values across image volumes while maintaining the overall shape of the image histogram and visual appearance of individual

TABLE 3

Hypoxia related markers and immunohistochemical staining data.

| Protein | Number of tumors with adequate staining | Positive staining | Description |
| --- | --- | --- | --- |
| VEGF (see, e.g., Reference 34) | 24 (96%) | 16 (67%) | In tumor biology both the EGF(R) and the VEGF(R) pathway are constitutively activated due to genetic abnormalities and ongoing tumor-associated hypoxia. |
| EGFR (see, e.g., Reference 34) | 24 (96%) | 18 (75%) | |
| CA-IX (see, e.g., Reference 36) | 25 (100%) | 23 (92%) | Carbonic anhydrase IX (CA-IX) is a transmembrane protein and is a tumor-associated carbonic anhydrase isoenzyme, which is overexpressed in solid tumors. |
| HIF-1α (see, e.g., Reference 34) | 9 (36%) | 7 (78%) | Hypoxia-inducible factor 1-alpha (HIF-1α): a pivotal mediator of cellular and systemic responses to hypoxia. |
| P53 (see, e.g., Reference 39) | 25 (100%) | 7 (28%) | P53 is a tumor suppressor protein, which is hypoxia induced. |
| MDM2 (see, e.g., Reference 40) | 25 (100%) | 5 (20%) | Mouse double minute 2 homolog (MDM2): a multifunctional oncoprotein that acts as a negative regulator of p53 tumor suppressor and plays a role in hypoxia-mediated VEGF upregulation. |
| CD24 (e.g., Reference 37) | 9 (36%) | 5 (55%) | CD24 is a cell adhesion molecule and effector of HIF-1α. |
| MRP-1 (see, e.g., Reference 35) | 9 (36%) | 2 (22%) | Multidrug resistance-associated protein 1 (MRP-1): involved with HIF-1α in multidrug resistance. |
| GLUT1 (see, e.g., Reference 36) | 25 (100%) | 13 (52%) | Glucose transporter 1 (GLUT1): effector of HIF-1α. |

Exemplary Computed Tomography Images

Patients underwent dual phase contrast-enhanced CT imaging prior to treatment. Post-contrast portal venous CT images were obtained following the administration of 150 mL iodinated contrast (e.g., Omnipaque 300, GE Healthcare, New Jersey) at 4.0 mL/sec, on multidetector CT (e.g., Lightspeed 16 and VCT, GE Healthcare, Wisconsin). The following scan parameters were used: pitch/table speed=0.938–0.984/9.37–39.37 mm; autoMA 220-380; noise index 12.5-14; rotation time 0.7-0.8 ms; scan delay 40 s after hepatic arterial phase, which can be determined by Smart Prep with a region of interest placement in the abdominal aorta at the level of the celiac artery. Axial slices reconstructed at each 2.5 mm interval were used for the analysis. The entire liver was scanned on each CT.

Exemplary Image Processing & Quantitative Imaging Phenotype Extraction

Pre-processing of the exemplary CT images was undertaken to determine the tumor region for further analysis. The tumor region was semi-automatically segmented from volumes. (See, e.g., Reference 45). The segmented/normalized image was verified by visual inspection prior to further analyses.

Figure 5A:
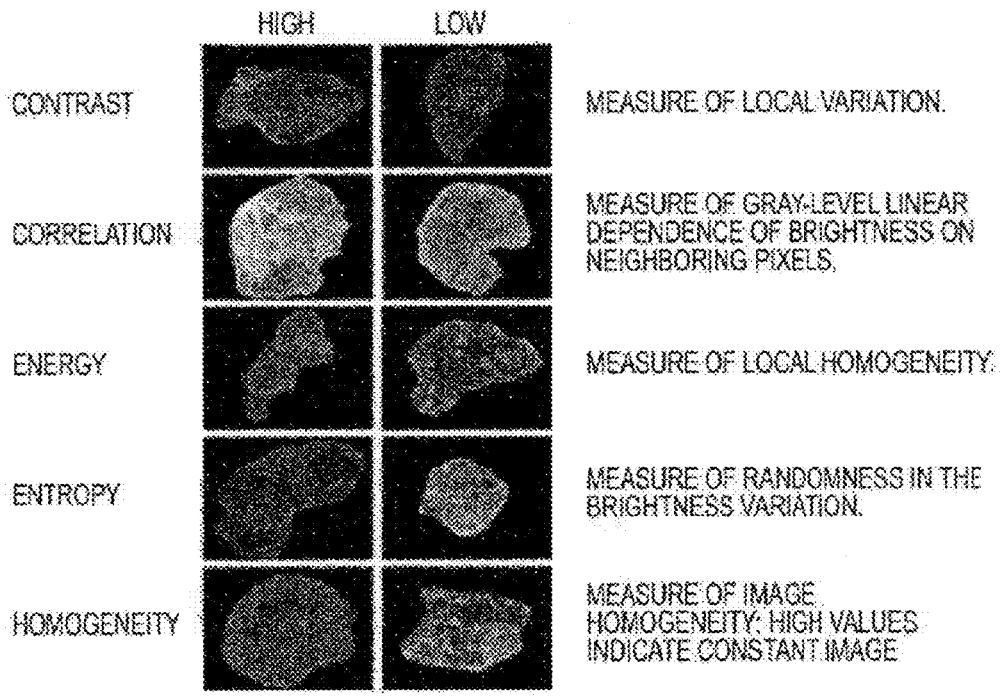
FIG. 5A is a set of images of representative tumors according to an exemplary embodiment of the present disclosure.

Second order texture statistics were utilized to examine the spatial relationship of neighboring pixels. Unlike first-order statistics that calculate cumulative statistics on individual pixel values, second-order statistics can evaluate the likelihood of observing spatially correlated pixels. (See, e.g., Reference 20). A 36×36 pixel neighborhood was chosen to assess this spatial relationship as this size demonstrated excellent discriminatory power in preliminary analyses. GLCMs were constructed to represent spatial relationships in the pixel neighborhoods using the standard implementation in the Image Processing Toolbox in MATLAB (e.g., MathWorks, Natick, Mass.). Four GLCM-based texture feature statistics were used: (i) contrast (e.g., local variation in the image), (ii) correlation (e.g., gray-level interdependence of brightness), (iii) energy (e.g., local homogeneity), and (iv) homogeneity (e.g., high values indicate constant image). Each was computed in four directions from 0°, 45°, 90° and 135°. Values were averaged over the four directions since the statistics were found to be directionally invariant. Values were computed for each CT slice and averaged over the whole tumor volume. A fifth texture statistic, image entropy (e.g., measure of randomness in brightness variation), was computed for the entire tumor. Tumors with high and low values for each texture feature are illustrated in FIG. 5A. Quantitative imaging phenotype was defined as either a single or combination of texture features, which measure tumor heterogeneity.

Exemplary Qualitative Imaging Features

Qualitative imaging features (see, e.g., Table 4 below) and hepatobiliary tumors in particular, were evaluated by an attending diagnostic radiologist, in order to assess whether radiographic inspection alone could predict the relationship between imaging features and protein expression levels.

Figure 4A:
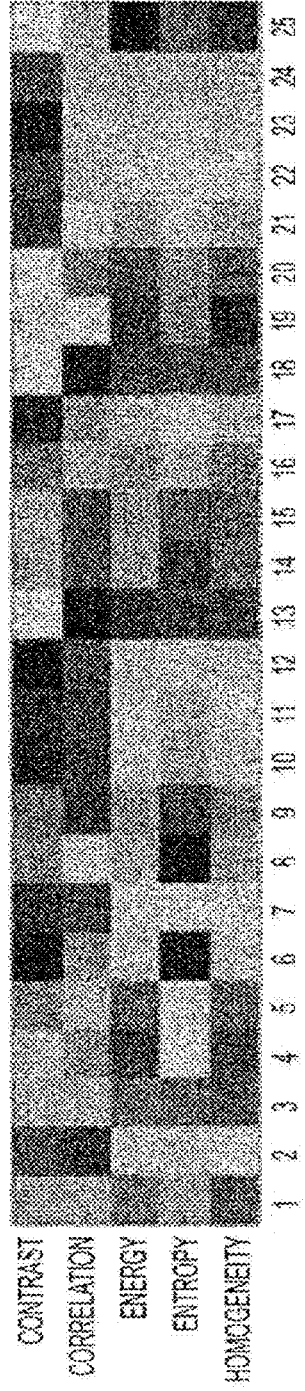
FIG. 4A is a diagram of normalized texture features extracted from CT images of 25 cholangiocarcinoma patients according to an exemplary embodiment of the present disclosure.
Figure 4B:
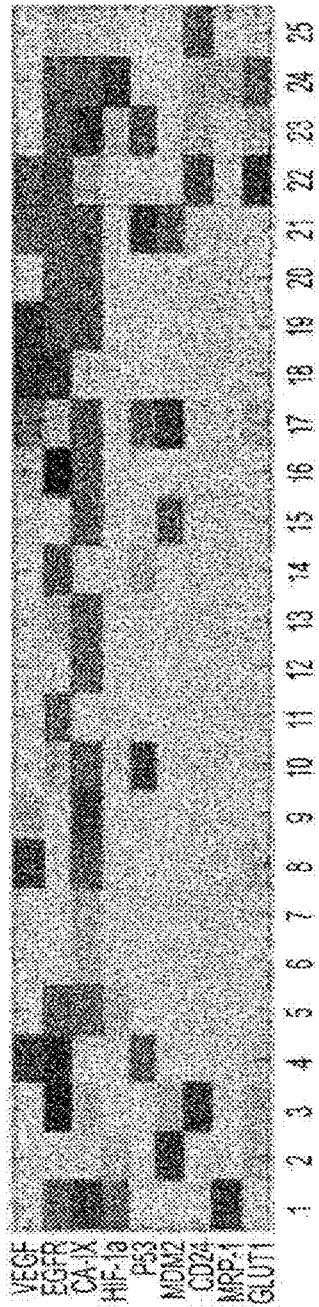
FIG. 4B is a diagram illustrating protein expressions of tumors.

Student t-test or Mann-Whitney test, as appropriate by the type of distribution. Categorical variables were compared using $\chi 2$ or the Fisher exact test depending on the number of observations. A p-value <0.05 was considered significant. Survival distributions were estimated using the Kaplan-Meier method and compared using the Cox-regression model. Time to event was calculated from initiation of hepatic artery infusion pump (See, e.g., References 46 and 47). As shown in the diagrams of FIGS. 4A and 4B, patients without the event of interest at last follow-up were censored. Linear regression analysis was undertaken to assess the relationship between texture features (see, e.g., FIG. 4A) and protein expression (see, e.g., FIG. 4B).

A regression line with protein expression levels as the dependent variable and texture feature as independent variable was derived, and Pearson's correlation coefficient was

TABLE 4

Qualitative imaging features definitions.

| Imaging feature name | Imaging feature definition |
| --- | --- |
| Tumor - Liver Difference, Maximum | The maximum of the arterial and portal venous phase tumor - liver difference scores |
| Attenuation Heterogeneity, Maximum | The maximum of the arterial and portal venous phase attenuation heterogeneity scores |
| Internal Arteries | The presence or absence of discrete arteries within the tumor |
| Capsule | A discrete rim of enhancement circumscribing the tumor on the portal venous phase imaging (may completely or partially circumscribe the tumor) |
| Hypodense Halo | A discrete rim of hypoattenuation circumscribing the tumor on both arterial and portal-venous phase imaging. A hypodense halo on arterial phase that became hyperdense on portal-venous phase was considered a capsule. |
| Internal Septa | The presence or absence of discrete septa with-in the tumor on the portal-venous phase of imaging |
| Tumor Margin Score, Maximum | The maximum of the arterial and portal-venous phase tumor margin score |
| Liver Capsule, Abutment[a] | Does the tumor contact the liver capsule? |
| Liver Capsule, Bulge[a] | Does the tumor bulge the liver capsule? |
| Capsule retraction[a] | Does the tumor retract the liver capsule? |
| Biliary dilatation[a] | Any biliary dilation? |
| Primary features | |
| Tumor Margin Score | The Tumor Margin score was a qualitative assessment of the transition zone from tumor tissue to liver tissue, scored from 0 to 4, where '0' is a perfectly demarcated tumor with a sharply defined transition between tumor and liver, and a score of '4' had an infiltrating morphology with a broad ill-defined transition along the entire periphery of the tumor. |
| Wash-Out | The relative decrease in attenuation of the tumor from arterial phase to portal-venous phase imaging, graded from 0 to 4, where '0' indicates that the tumor is isodense to adjacent liver, and a score of '4' indicates the attenuation of the tumor is much less than the adjacent background liver. |
| Tumor - Liver Difference | The degree to which the tumor attenuation differed from that of adjacent liver, graded from 0 to 4, where '0' indicates that the tumor is isodense to adjacent liver and is perfectly homogeneous, and a score of '4' indicates the attenuation of the tumor differed greatly from the adjacent background liver |
| Attenuation Heterogeneity | A qualitative measure of the dispersion of attenuation values within the tumor. For example, a score of '0' meant the tumor was of uniform attenuation, whereas a score of '4' meant the tumor had areas of both very high and low attenuation. |

[a]These imaging features are yes/no questions.

Exemplary Statistical Analysis

Figure 5B:
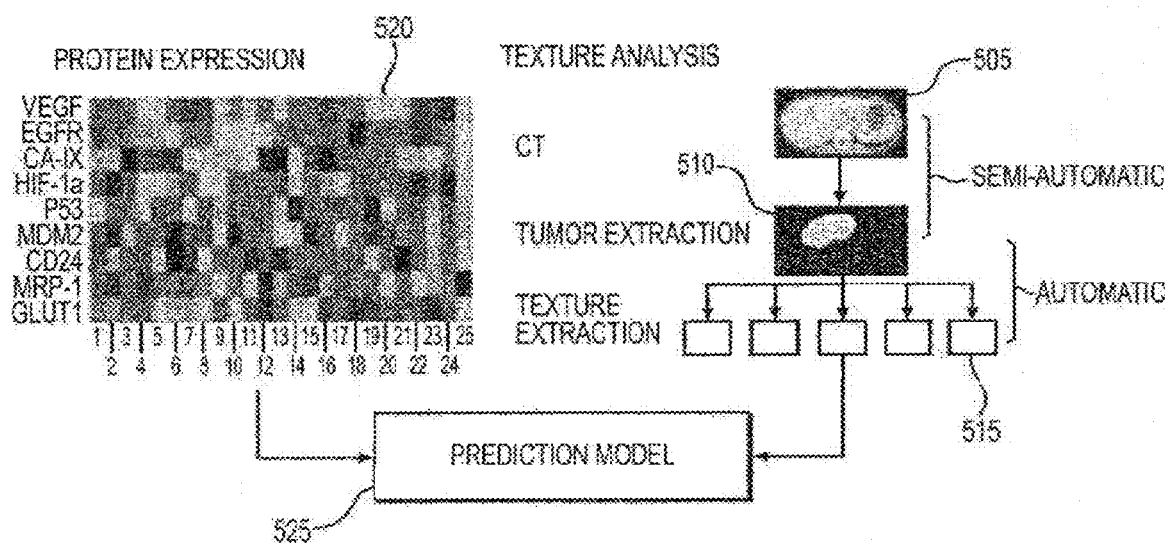
FIG. 5B is a set of diagrams of protein expressions and the texture analysis of tumors according to an exemplary embodiment of the present disclosure.

Descriptive and comparative statistics were performed using SPSS version 22 (e.g., IBM Corporation, Armonk, N.Y., USA). Continuous variables were compared using the calculated for all combinations of texture features and protein expression variables. Confidence intervals with $\alpha=0.05$ were computed for each regression. A multiple linear regression was used to model the relationship between combinations of texture features to illustrate the predictive power of texture feature sets (e.g., quantitative imaging phenotypes). Exemplary tumor for high and low values of five texture variables are shown in the images on FIG. 5A. FIG. 5B shows a schematic diagram of the exemplary prediction model relating protein express to texture features according to an exemplary embodiment of the present disclosure. For example as shown therein, a CT image 505 can be used in a tumor extraction procedure 510. After the tumor has been extracted, a texture extraction procedure 515 can be performed, the results of which can be input onto a prediction model 525. Additionally, a protein expression 520 can also be input into prediction model 525.

Exemplary Clinicopathologic and Molecular Characteristics

Forty-four patients with initially unresectable ICC were included in the exemplary study. Twenty patients were excluded due to inadequate tissue for immunohistochemical staining and 3 patients with preoperative CT scan inadequate for texture analysis. 4 patients who were taken off the previous two trials after the pre-treatment biopsy and hepatic artery infusion pump placement were included for the outcome analyses (e.g. response and survival). A total of 25 patients with histologically proven ICC were included. The median age was 62 years (e.g., range: 54-84) and 20 patients (e.g., 80%) were female. The median tumor size was 10.2 cm (e.g., range: 4-14), 10 (e.g., 40%) were single tumors, and 17 (e.g., 68%) were moderately differentiated. Table 4 details the results of the immunohistochemical staining. Positive immunohistochemistry staining was recorded for VEGF in 67% of the cases, EGFR in 75%, CD24 in 55%, CA-IX in 92%, HIF-1α in 78%, P53 in 28%, MDM2 in 20%, MRP-1 in 22%, and
GLUT1 in 52%.

Figure 6A:
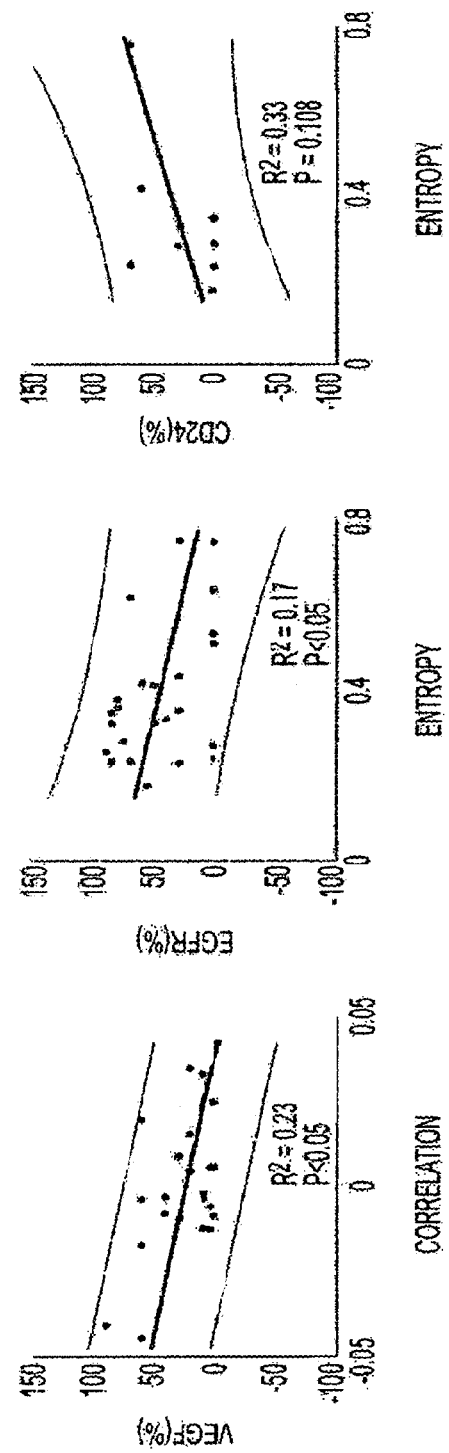
FIG. 6A are graphs illustrating selected linear regression plots of texture features according to an exemplary embodiment of the present disclosure.
Figure 6B:
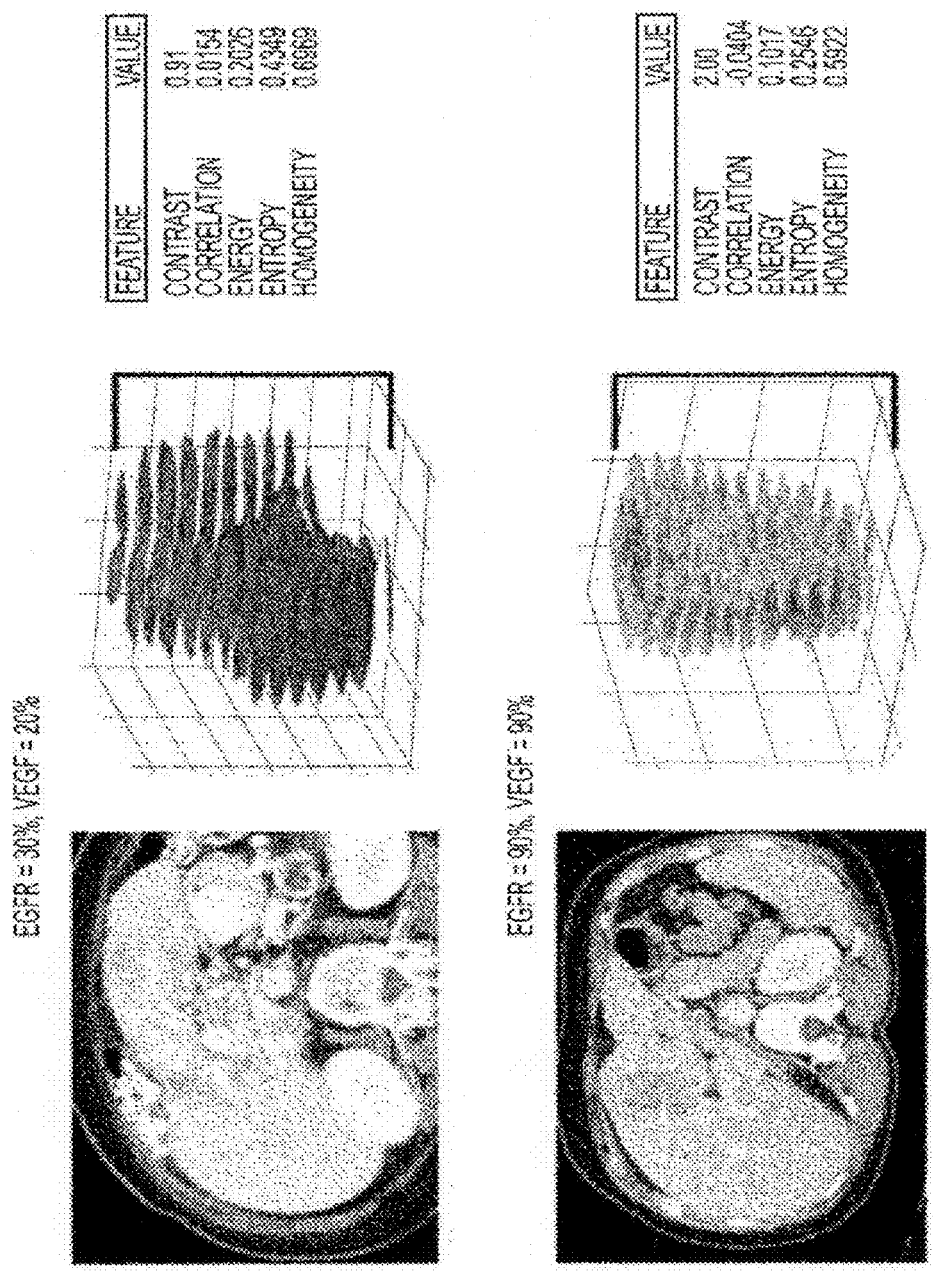
FIG. 6B is a set of images of segmented tumors according to an exemplary embodiment of the present disclosure.

Exemplary Quantitative Imaging Phenotypes, Qualitative Imaging Features and Protein Expression Levels Selected linear regression plots of tumor texture features with respect to protein expression levels are shown in FIGS. 6A and 6B. Correlation texture feature (e.g., $R^2=0.23$, $p<0.05$) was significantly associated with VEGF expression. Correlation (e.g., $R^2=0.21$, $p<0.05$) and entropy (e.g., $R^2=0.17$, $p<0.05$) texture features were significantly related to EGFR expression. A trend was demonstrated between entropy and CD24 expression (e.g., $R^2=0.33$, $p=0.108$). By contrast, there were no significant associations between any of the texture features and either CA-IX, HIF-1α, P53, MDM2, MRP-1, or GLUT1.

Multiple linear regressions of the significant texture features from the univariate analysis test the predictive power of quantitative imaging phenotypes (e.g., texture features sets). Table 5 below summarizes these results. Correlation and contrast explain 26% of VEGF expression (e.g., $R^2=0.26$, $p<0.05$) in this model. In the case of EGFR expression, discriminatory power of the model was substantially improved when all five texture features were combined (e.g., $R^2=0.47$, $p<0.05$) with the combination of correlation, entropy, and homogeneity representing a substantial portion (e.g., $R^2=0.41$, $p<0.05$). A trend was observed between CD24 expression levels and the combination of entropy, correlation, and homogeneity (e.g., $R^2=0.68$, $p=0.1$). (See, e.g., FIG. 6A). FIG. 6B compares representative texture feature values for tumors with low and high VEGF and EGFR expression. A heat map of cholangiocarcinoma patients with extracted texture features and protein expression data is shown in FIG. 4.

TABLE 5

Multiple linear regression analysis of hypoxia markers and quantitative imaging phenotypes.

| Hypoxia markers (%) | Imaging phenotype | $R^2$ | p-value |
|---|---|---|---|
| VEGF | Entropy, energy, correlation, contrast, homogeneity | 0.3 | 0.2 |
|  | Entropy, energy, correlation, contrast | 0.3 | 0.12 |
|  | Entropy, correlation, contrast | 0.28 | 0.08 |
|  | Correlation, contrast | 0.26 | 0.04 |
|  | Correlation | 0.23 | 0.016 |
| EGFR | Entropy, energy, correlation, contrast, homogeneity | 0.47 | 0.029 |
|  | Entropy, energy, correlation, homogeneity | 0.43 | 0.025 |
|  | Entropy, correlation, homogeneity | 0.41 | 0.013 |
| CD24 | Entropy, correlation, energy, contrast, homogeneity | 0.73 | 0.36 |
|  | Entropy, correlation, energy, homogeneity | 0.73 | 0.18 |
|  | Entropy, correlation, homogeneity | 0.68 | 0.104 |

At a median follow-up time of 39 months (e.g., range: 11-90 months) the median OS was 37 months (e.g., 95% CI: 15-59). The median progression-free survival ("PFS") was 9 months (e.g., 95% CI: 6-12) and the response rates were 62%, 33%, and 5% for partial response, stable disease, and progressive disease, respectively. Ultimately, two patients responded sufficiently to undergo resection.

Table 6 details thirteen qualitative imaging features and demonstrates that VEGF expression was associated with two qualitative imaging features (e.g., 'tumor-liver difference' and 'attenuation heterogeneity', $p<0.05$ for both). CD24 expression was correlated with 'biliary dilatation' (e.g., $p<0.05$), whereas EGFR was not associated with any of the quantitative imaging features. None of these three exemplary qualitative imaging features correlated with any of the texture features.

TABLE 6

Relationship between qualitative imaging features and protein expression levels by linear regression.

| Imaging features[a] | EGFR (%) | | | VEGF (%) | | | CD24 (%) | | |
|---|---|---|---|---|---|---|---|---|---|
| | β | P-value | $R^2$ | β | P-value | $R^2$ | β | P-value | $R^2$ |
| Tumor volume, cc | −0.17 | 0.4 | 0.3 | −0.2 | 0.3 | 0.2 | 0.6 | 0.07 | 0.4 |
| Tumor - Liver | −0.09 | 0.7 | 0.007 | −0.4 | 0.04 | 0.2 | 0.4 | 0.3 | 0.2 |
| Difference, Maximum Attenuation | −0.09 | 0.7 | 0.008 | −0.5 | 0.02 | 0.2 | 0.3 | 0.4 | 0.1 |
| Heterogeneity, Maximum Internal arteries | −0.06 | 0.8 | 0.004 | 0.3 | 0.2 | 0.07 | −0.01 | 0.9 | <0.001 |
| Capsule | −0.3 | 0.1 | 0.1 | −0.05 | 0.8 | 0.003 | 0.3 | 0.3 | 0.1 |
| Hypodense halo | 0.2 | 0.4 | 0.03 | 0.01 | 0.9 | <0.001 | NA | NA | NA |
| Wash out | 0.3 | 0.1 | 0.1 | −0.05 | 0.8 | 0.003 | −0.5 | 0.1 | 0.3 |
| Internal septa | −0.3 | 0.1 | 0.1 | 0.01 | 0.9 | <0.001 | 0.3 | 0.4 | 0.1 |
| Tumor margin score max | 0.3 | 0.2 | 0.07 | −0.1 | 0.6 | 0.01 | −0.1 | 0.7 | 0.02 |
| Liver capsule abutment | 0.3 | 0.2 | 0.09 | 0.1 | 0.6 | 0.01 | NA | NA | NA |
| Liver capsule bulge | 0.1 | 0.5 | 0.02 | 0.1 | 0.6 | 0.01 | NA | NA | NA |
| Capsule retraction | 0.1 | 0.7 | 0.009 | −0.1 | 0.5 | 0.02 | −0.5 | 0.2 | 0.2 |
| Biliary dilatation | −0.1 | 0.5 | 0.02 | −0.3 | 0.1 | 0.1 | 0.7 | 0.048 | 0.5 |

NA—not analyzed.
[a]Imaging features are defined in Table 6.

Exemplary Quantitative Imaging Phenotypes and Outcome

No association was noted between OS and either VEGF, EGFR, or CD24 expression levels. However, a trend was observed between the texture feature entropy and time to progression (p=0.1) and PFS (p=0.08). In addition, a trend was observed between the best radiological response and the correlation texture feature (e.g., p=0.08).

Exemplary Radiogenomics in Cholangiocarcinoma Discussion

The above description illustrates a link between imaging phenotypes and molecular profiling of tumors using a cholangiocarcinoma model. ICC exhibits a high degree of abnormal tissue vasculature (see, e.g., Reference 48) and expression of hypoxia markers. (See, e.g., Reference 49). These features, combined with their large size, make ICC a good model to test the hypothesis that overexpression of hypoxia markers, reflecting a hypoxic microenvironment and relative hypoperfusion, can be detected by the exemplary system, method, and computer-accessible medium.

Molecular profiling of cancer has become an integral part of treatment selection, and can provide predictive and prognostic information, as shown in breast cancer by the immunohistochemical assessment of molecular markers such as estrogen receptor, progesterone receptor, and HER2 (e.g., human epidermal growth factor receptor 2). (See, e.g., Reference 50). Similar progress has been seen in leukemia, lymphoma and other malignancies. (See, e.g., Reference 32). Molecular profiling methods can utilize invasive tissue procurement procedures with inherent risks (e.g., pain, infection, bleeding or cancer seeding). In addition, these methods can be limited in their utility, since the tissue obtained can be sacrificed to extract nucleic acids or proteins for analysis, and can only provide information at a single time point.

Radiogenomics can utilize novel non-invasive methods to characterize imaging phenotypes and correlate them with the molecular features of tumors. (See, e.g., Reference 51). Previous work (see, e.g., Reference 52) demonstrated the potential of non-invasive imaging to decode the molecular makeup of human liver cancer. Qualitative imaging features, visually assessed by a radiologist, were correlated with gene modules (e.g., groups of genes with coherent variation in expression across multiple samples). For instance, a combination of 3 exemplary imaging features correlated with the expression level of a gene module, which was highly enriched for genes involved in cell proliferation, including VEGF. However, it may not clear how the association with gene modules will have direct implementation in daily practice.

The exemplary system, method and computer-accessible medium, according to an exemplary embodiment of the present disclosure, can be used to identify a relationship between clinically-oriented molecular markers and objective imaging phenotypes. A substantial portion of tumors in the exemplary analysis demonstrated positive staining for VEGF (67%), EGFR (75%) and CD24 (55%), as previously noted. (See, e.g., References 49 and 53). These proteins, and other hypoxia markers, can be associated with tumor angiogenesis, which can result in abnormal vascular beds, characterized by high permeability, high interstitial pressure and hypoperfusion. (See, e.g., Reference 34). The exemplary system, method and computer-accessible medium, according to an exemplary embodiment of the present disclosure, was used to determine phenotypes by texture analysis, which can quantify visible variations in enhancement. The results show that quantitative texture features were associated with overexpression of certain hypoxia markers. VEGF and EGFR expression levels were associated with specific quantitative imaging phenotypes, whereas CD24 revealed a promising trend, considering the small sample size. It can likely be that these quantitative imaging phenotypes can reflect perfusion variations in tumors that overexpress these hypoxia markers (e.g., VEGF and EGFR), which mirror the hypoxic microenvironment and abnormal tumor vasculature. (See, e.g., Reference 54). Three conventional (e.g., qualitative) imaging features correlated with protein expression, including 'tumor-liver difference' and 'attenuation heterogeneity,' which can be subjective assessments of overall tumor enhancement and heterogeneity on a five point scale by a radiologist. However, neither of these conventional imaging features correlated with the quantitative texture features, thereby emphasizing the lack of redundancy between quantitative and qualitative imaging features. Furthermore, the use of qualitative imaging features can also be hampered by potential large interobserver variability, as demonstrated in a recent study on the application of imaging criteria in the diagnosis of hepatocellular carcinoma by a group of radiologists. (See, e.g., Reference 55). The use of quantitative and automated imaging phenotypes can be an attractive approach to radiogenomics.

CD24 is a cell adhesion molecule that was shown to be associated with increased cell motility, adhesion, migration, invasion and chemo-resistance capabilities in cholangiocarcinoma. (See, e.g., Reference 56). It was suggested that overexpression of CD24 in cholangiocarcinoma can be associated with poor survival and lack of response to chemotherapy. (See, e.g., Reference 57). Moreover, it was proposed that CD24 can have a role as a new target for directed molecular therapy in cholangiocarcinoma, as decreased tumor cell invasiveness was observed with inhibition of CD24. (See, e.g., Reference 56). In view of the small cohort, a trend between specific quantitative imaging phenotypes and CD24 expression levels can be observed.

A wide spectrum of clinical applications exists for radiogenomic methods that can predict overexpression of VEGF, EGFR or other hypoxia markers. Tumor-related angiogenesis can be known to affect local tumor growth and metastasis in a variety of human cancers. (See, e.g., Reference 58). On the basis of these findings, antiangiogenic agents were recently developed and incorporated into treatment procedures of multiple cancers. (See, e.g., Reference 34). Bevacizumab (e.g., anti-VEGF antibody) and cetuximab (e.g., anti-EGFR antibody) can be integral portion of the treatment guidelines for colorectal cancer (see, e.g., Reference 59) and prediction of treatment response to these agents is currently based on the tumor's molecular profile. (See, e.g., References 59-61). Recently, a new VEGF inhibitor, ramucirumab, was FDA approved for treatment of advanced gastric adenocarcinoma. As the armamentarium of signal transduction inhibitors enlarges, it is likely that the clinical implications of radiogenomic profiling will grow. Moreover, increased need for non-invasive radiogenomic profiling can be expected as neoadjuvant procedures can increase in frequency since assessment of treatment response can be inadequate using standard imaging procedures (e.g., RECIST), and repeated tumor biopsy can be an impractical option.

Exemplary Survival Prediction Using Preoperative Computed Tomography Texture Analysis: Data and Outcomes Demographics, preoperative data (e.g., biliary stenting, total bilirubin, CA19-9), perioperative data and pathology (e.g., nodal status, tumor differentiation, lymphovascular invasion, perineural invasion) were collected. Adjuvant therapy and recurrence were reported as well. Local recurrence was defined as a local ill-defined mass in the pancreatic resection bed on CT with biopsy-proven recurrent PDAC or increased serum levels of tumor markers. Distant recurrence was defined based on radiologic or histologic evidence.

Overall survival was defined as the interval between the operative date and the last follow-up date. Death at the last follow-up was considered as an event. Any patient alive at last follow-up was censored.

Exemplary Survival Prediction Using Preoperative Computed Tomography Texture Analysis: CT Acquisition Each patient received a conventional portal venous phase contrast-enhanced CT imaging within 6 weeks prior to surgery was performed. Post-contrast CT images were obtained following the administration of 150 mL iodinated contrast (e.g., Omnipaque 300, GE Healthcare, New Jersey) at 4.0 mL/sec, on multi detector CT (e.g., Lightspeed 16 and VCT, GE Healthcare, Wisconsin). The following scan parameters were used: pitch/table speed=0.984-1.375/39.37-27.50 mm; autoMA 220-380; noise index 12.5-14; rotation time 0.7-0.8 ms; scan delay 80-85 s. Axial slices reconstructed at each 2.5 mm interval were used for the analysis.

Exemplary Survival Prediction Using Preoperative Computed Tomography Texture Analysis: Image Processing On preoperative portal venous phase CT imaging, the pancreas tumor was manually designated from surrounding structures by an attending radiologist (e.g., RKGD) who was blinded to all clinical data, using Scout Liver (e.g., Pathfinder Technologies Inc., Nashville, Tenn.). An attending computer scientist (e.g., ALS) developed custom software in C++ and MATLAB (e.g., MathWorks, Natick, Mass.) for automatic image analysis in the tumor region. Pixel values in the tumor region were thresholded by −100 HU and 300 HU to exclude extreme attenuation values such as air and metal from analysis. The tumor volume was normalized using an exemplary procedure that can change the range of pixel intensity values to [0,1] while maintaining the appearance and histogram of the image. (See, e.g., Reference 62).

Figure 8:
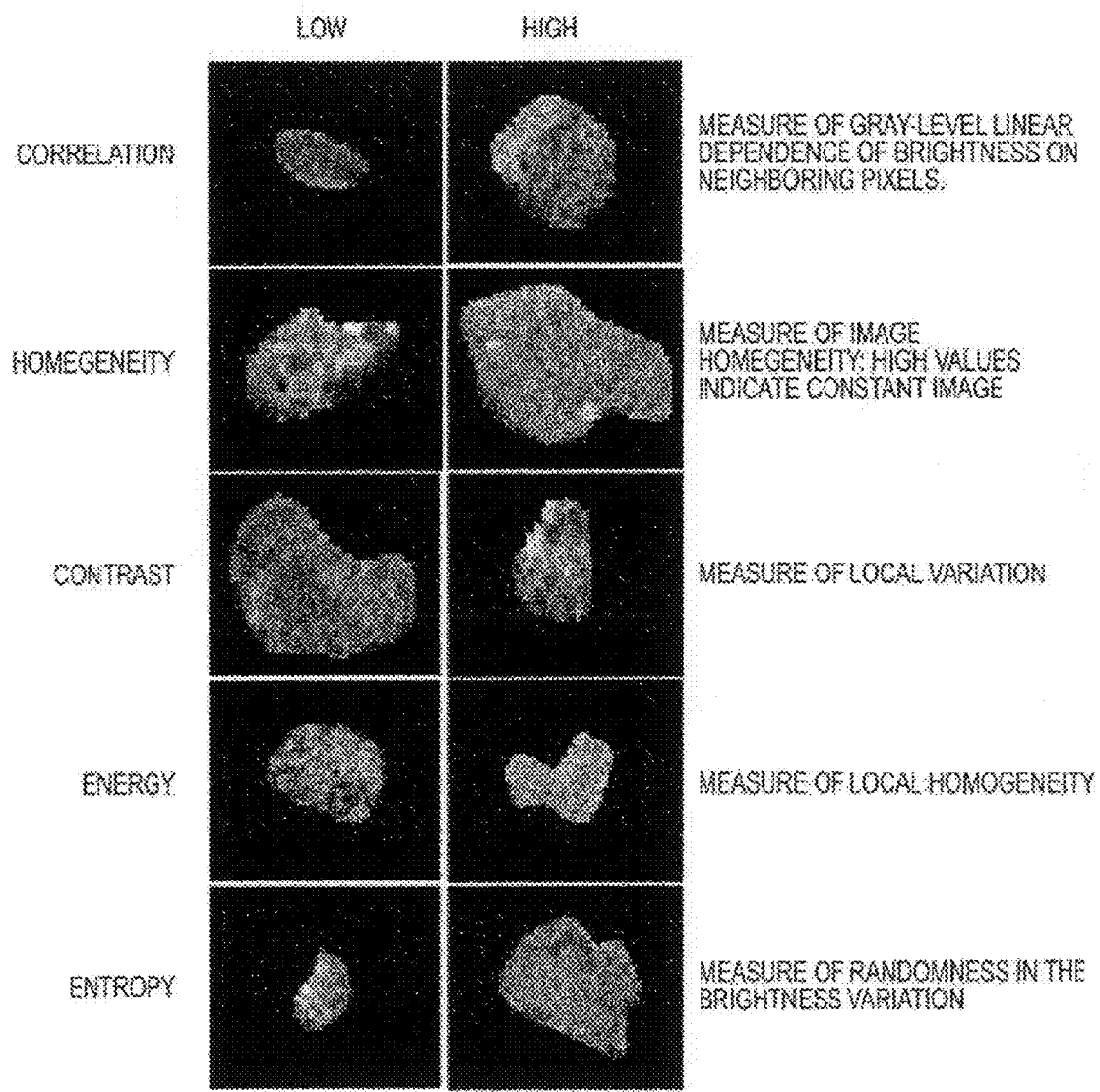
FIG. 8 is a set of images of exemplary tumors with high and low values for each second-order texture variables according to an exemplary embodiment of the present disclosure.

Exemplary Survival Prediction Using Preoperative Computed Tomography Texture Analysis: Texture Analysis The spatial relationship of pixels in the tumor volume were quantified with standard GLCMs (see, e.g., References 63-65) using implementations from the Image Processing Toolbox in MATLAB. GLCM can represent the number of neighboring gray levels over a specified pixel distance and direction in an image. Once the matrix was constructed, features were extracted using well-defined statistics. The matrix was constructed based on preliminary analysis that determined about a 10-pixel distance provided optimal discriminatory power in PDAC tumors. GLCM were constructed for each direction from 0°, 45°, 90°, to 135° and on each slice of the tumor. Four feature statistics were extracted from the GLCM: (i) contrast (e.g., local variation in the image), (ii) correlation (e.g., gray-level interdependence of brightness), (iii) energy (e.g., local homogeneity), and (iv) homogeneity (e.g., high values indicate constant image). Feature values were found to be directionally invariant, and were averaged over the four directions, yielding one feature value per CT slice. A fifth statistic, image entropy (e.g., measure of randomness in brightness variation), was computed for each slice. Averaging the feature values across the tumor yielded one value for each statistic for the entire tumor. Example tumors with high and low values for each feature are illustrated in FIG. 8. Five feature statistics were automatically generated for each tumor, and were submitted for independent statistical analysis by a senior attending statistician.

Exemplary Survival Prediction Using Preoperative Computed Tomography Texture Analysis: Statistical Analysis Descriptive statistics were expressed as numbers and percentages for categorical variables and mean with range for continuous variables. Correlation between texture variables and clinical variables was assessed using a nonparametric Spearman's correlation test. Each texture variable was dichotomized using the mean. Univariate (e.g., log-rank test) was performed regarding overall survival. Due to the low number of events, texture variables considered significant in univariate analysis (e.g., p<0.10) were subsequently tested in separate multivariate models (e.g., Cox-regression models) including other clinical variables significant in univariate analysis. Results from the Cox proportional hazards models were reported as hazard ratios (e.g., HRs), with 95% confidence intervals (e.g., CIs) and P values. All statistical analyses were performed with SPSS Statistics software (e.g., version 22.0, IBM, Armonk, N.Y., USA).

Exemplary Survival Prediction Using Preoperative Computed Tomography Texture Analysis: Perioperative Data During this period, 329 patients underwent resection of PDAC, of which 23 patients met the inclusion criteria. Perioperative data listed in Table 7 below show homogeneity across the cohort. Most patients were male (e.g., n=17; 73.9%) and most underwent preoperative endoscopic biliary stenting (e.g., n=17; 73.9%). Preoperative CA19-9 level was available in 18 patients, and was elevated in 17 patients (e.g., 94.4%). Preoperative CT imaging was performed at a median interval before surgery of 12 days (e.g., range, 1-43 days). Twenty one patients underwent pancreatoduodenectomy for a proximal pancreatic tumor, and a distal splenopancreatectomy was performed in the remaining two patients. Morbidity occurred in 6 patients, and was major in 4 patients (e.g., 17.4%) involving three intra-abdominal abscesses and one pancreatic leak, all utilizing percutaneous drainage. Median length of stay was eight days (e.g., range, 5-22). Adjuvant chemotherapy was delivered in 19 patients (e.g., gemcitabine alone, n=14; chemoradiation, n=4). Five patients did not receive any adjuvant therapy (e.g., unfit for adjuvant chemotherapy, n=1; prolonged postoperative recovery, n=1; chemotherapy declined, n=2).

TABLE 7

Descriptive data of the cohort.

|  | Overall cohort (n = 23) |
|---|---|
| Preoperative data | |
| Sex, male | 17 (73.9%) |
| Age, years | 72 (48-82) |
| Preoperative stent | 17 (73.9%) |
| Preoperative Total Bilirubin, mg/dl | 0.9 (0.4-14.3) |
| Preoperative CA19-9, U/l | 164.5 (31-9646) |
| Pathology data | |
| Positive nodal status | 19 (82.6%) |
| Lymphovascular invasion | 16 (69.6%) |
| Perineural invasion | 22 (95.7%) |
| Differentiation | |
| Moderate | 16 (69.6%) |
| Poor | 7 (30.4%) |
| Positive resection margin | 5 (21.7%) |
| Postoperative data | |
| Major Morbidity | 4 (17.4%) |
| Adjuvant Chemotherapy | 18 (78.3%) |
| Median FU, months | 14 (4-78) |

Unless otherwise specified, data are median with minimum and maximum in parentheses.

Exemplary Survival Prediction Using Preoperative Computed Tomography Texture Analysis: Pathologic Data Pathologic data are listed in Table 7. Tumor differentiation was intermediate in about 69.6% of patients. Most patients presented with lymphovascular invasion (e.g., about 69.6%), perineural invasion (e.g., about 95.7%), and lymph nodes metastasis (e.g., about 82.6%). Resection was incomplete in 5 patients (e.g., about 21.7%) with positive pancreatic margin (e.g., n=4) or posterior margin (e.g., n=2).

Figure 9:
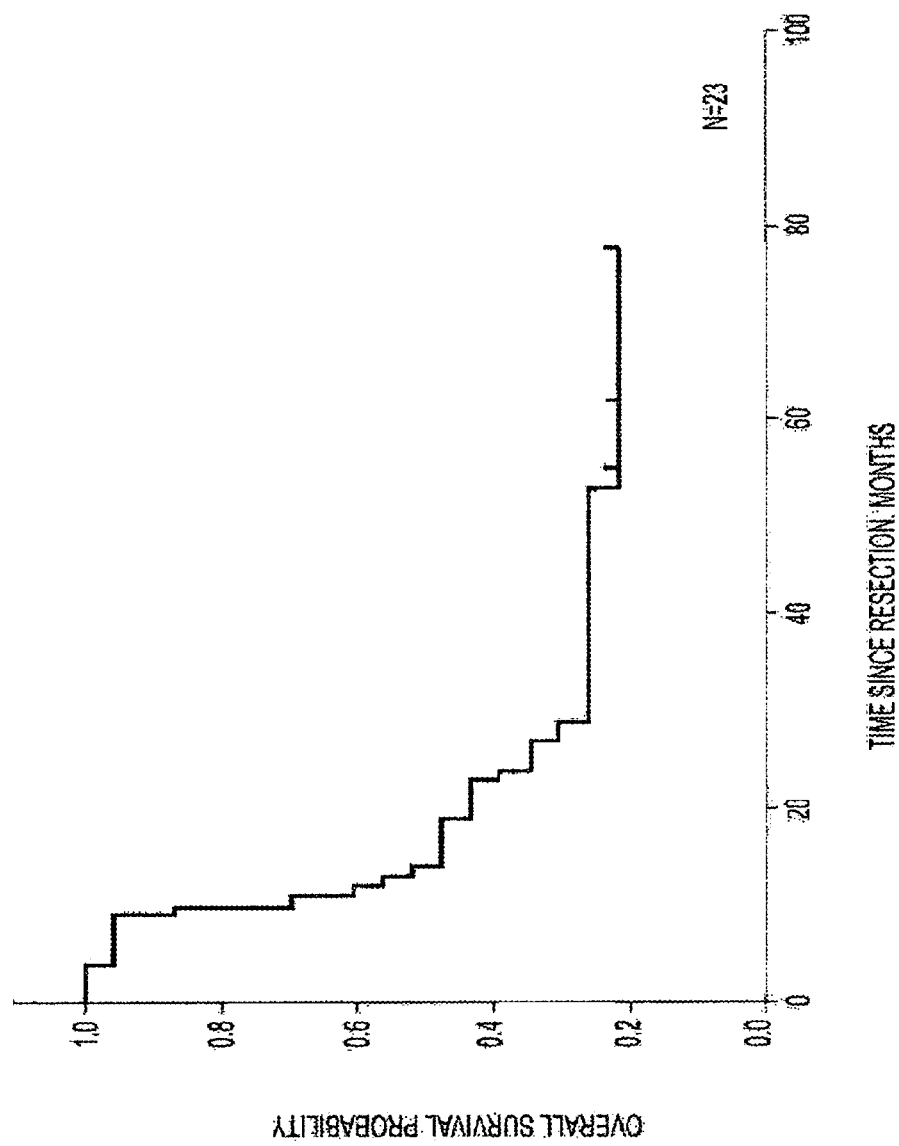
FIG. 9 is a graph of the Kaplan-Meier overall survival curve for patients according to an exemplary embodiment of the present disclosure.

Exemplary Survival Prediction Using Preoperative Computed Tomography Texture Analysis: Survival and Recurrence Five patients were alive after a median follow-up time of 73 months (e.g., range, 55-78). Median overall survival was 14 months in the whole cohort (see, e.g., graph shown in FIG. 9). Overall, 21 patients experienced recurrence with a median time to recurrence of 7.7 months (e.g., range, 1-23). Median recurrence-free survival was 8.4 months (e.g., range, 4.9-11.8). Recurrence patterns were distant only (e.g., n=16; 76.2%), local only (e.g., n=2; 9.5%) and both distant and local (e.g., n=3; 14.3%).

Exemplary Survival Prediction Using Preoperative Computed Tomography Texture Analysis: Clinical and Textures Variables and Survival No clinical variables correlated with tumor texture variables (e.g., a Spearman test). Among sex, age, nodal status, preoperative CA 19-9 level, tumor differentiation, lymphovascular invasion, perineural invasion and major morbidity, only tumor differentiation was significantly associated with overall survival (e.g., p=0.029).

Figure 10:
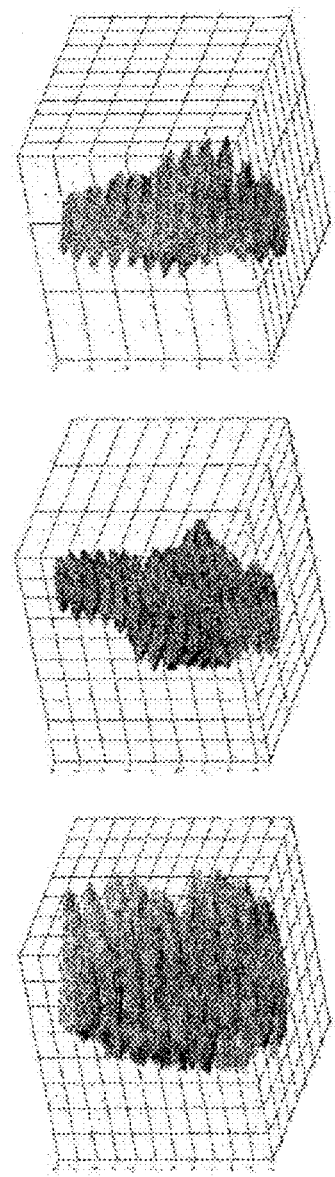
FIG. 10 is a set of images and corresponding texture data for a set of patients according to an exemplary embodiment of the present disclosure.
Figure 11:
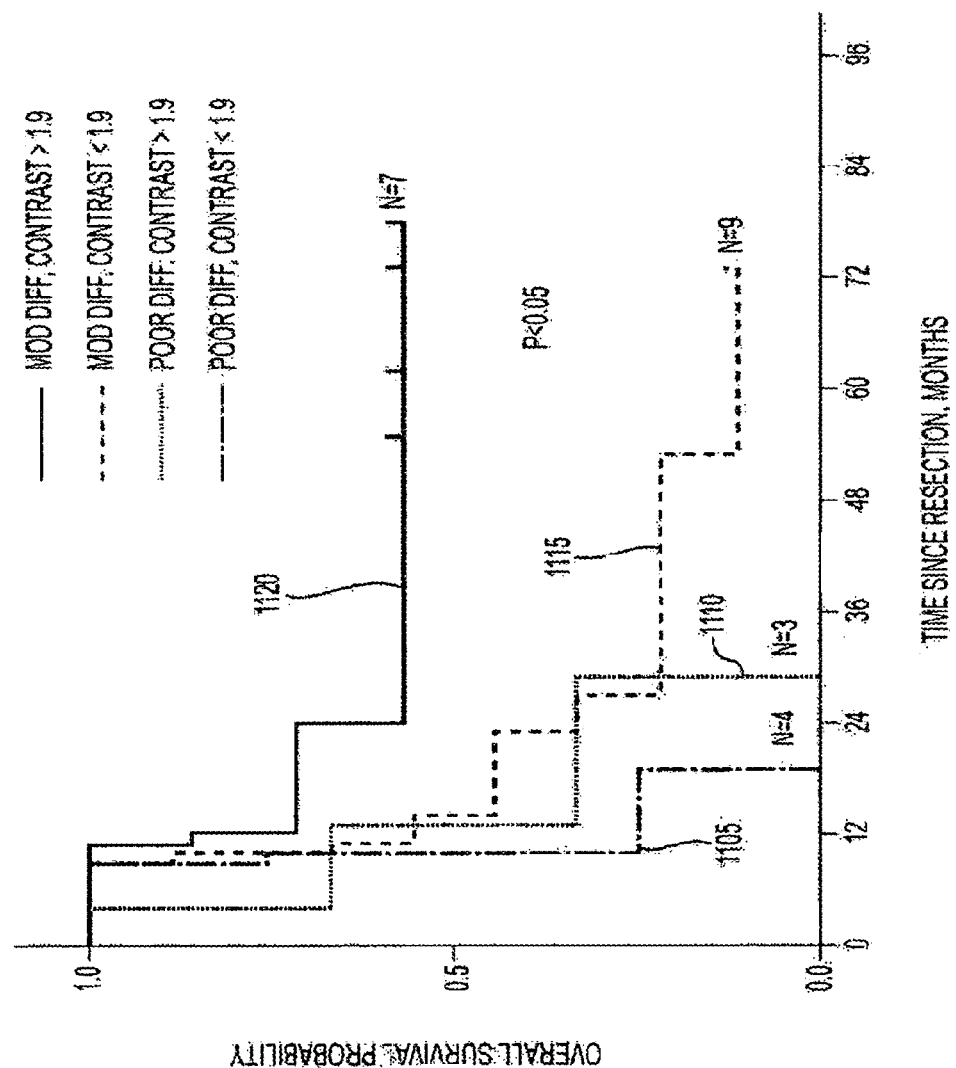
FIG. 11 is a graph illustrating the Kaplan-Meier overall survival curve using two variables according to an exemplary embodiment of the present disclosure.

A number of texture variables showed trends towards improved overall survival, including correlation <0.03 (e.g., p=0.09); contrast <1.9 (e.g., p=0.07) and homogeneity <0.62 (e.g., p=0.1) in univariate analysis (e.g., Table 8 below). These findings are illustrated in FIG. 10, with texture data from three patients included in the current cohort. Multiple multivariate models including alternatively tumor differentiation, correlation <0.03, homogeneity <0.62 and contrast <1.9 were then tested (e.g., Table 9 below). Out of the three exemplary multivariate models, the model that included tumor differentiation, and had a contrast <1.9, provided an accurate patient stratification (e.g., p=0.038). (See, e.g., graph shown in FIG. 11). Patients with high texture values and moderately differentiated tumors had better overall survival (e.g., line 1120), whereas patients with lower texture values and moderately differentiated tumors had poorer survival (e.g., line 1115). Similarly, tumors with lower texture values had better survival in poorly differentiated tumors (e.g., lines 1105 vs. lines 1110).

TABLE 8

Tumor Texture Variables and Overall Survival.

|  | Mean Tumor | Median Overall Survival | | |
|---|---|---|---|---|
|  | Texture | Below Mean | Above mean | p-value |
| Correlation | 0.03 (0.06) [−0.14 to 0.22] | 11 months (n = 14) | 27 months (n = 9) | 0.09 |
| Homogeneity | 0.62 (0.09) [0.5 to 0.72] | 24 months (n = 9) | 11 months (n = 14) | 0.1 |
| Contrast | 1.90 (1.29) [0.99 to 4.24] | 11 months (n = 13) | 24 months (n = 10) | 0.07 |
| Energy | 0.15 (0.07) [0.07 to 0.25] | 12 months (n = 12) | 19 months (n = 11) | 0.65 |
| Entropy | 0.05 (0.03) [0.01 to 0.11] | 19 months (n = 11) | 13 months (n = 12) | 0.96 |

Unless otherwise specified, data are median with interquartile range in parentheses and minimum and maximum in brackets.

TABLE 9

Cox-Proportional Hazards Regression Analysis of Clinical and Texture Variables.

|  | Variable | HR | p-value |
|---|---|---|---|
| MODEL 1 | Differentiation | 2.4 (0.8-6.5) | 0.087 |
|  | Correlation < 0.03 | 2 (0.7-5.8) | 0.202 |
| MODEL 2 | Differentiation | 2.3 (0.8-6.4) | 0.11 |
|  | Homogeneity < 0.62 | 0.5 (0.18-1.6) | 0.26 |
| MODEL 3 | Differentiation | 3.1 (1.1-8.4) | 0.03 |
|  | Contrast < 1.9 | 2.6 (0.9-7.1) | 0.069 |

Data in parentheses are 95% CIs.

Exemplary Survival Prediction Using Preoperative Computed Tomography Texture Analysis: Discussion An exemplary finding/determination in this homogeneous patient cohort can be that preoperative quantitative image analysis of PDAC can be integrated with other perioperative clinical variables to predict survival after resection. Three out of five texture variables were associated with overall survival, of which contrast showed the strongest association (e.g., HR=2.6; 95% CI=0.9-7.1; p=0.069).

To date, it is believed that no preoperative prognostic factor has been validated in PDAC management, while prolonged overall survival after curative resection remains rare. Using preoperative enhanced CT imaging to generate prognostic factors is of particular interest. First, CT imaging is currently the imaging modality of choice in clinical PDAC staging. (See, e.g., Reference 66). Second, CT scanning is noninvasive and widely available. Third, neoadjuvant therapy is worthy of further investigation in resectable PDAC and predicting long term post-surgical outcomes can improve patient selection in the neoadjuvant setting. (See, e.g., Reference 67). Recently, standardized uptake value greater than 6 on preoperative 18F-fluorodeoxyglucose positron emission tomography (e.g., FDG-PET) has been reported as a prognostic factor for resectable PDAC. (See, e.g., Reference 68). Texture analysis has also been reported on MRI and positron emission tomography ("PET"). (See, e.g., References 69, 70). However, these imaging modalities may not be used routinely for PDAC preoperative staging.

Perioperative clinical variables, and especially tumor pathology characteristics in the current cohort, were similar to those previously reported, with high rates of positive regional lymph nodes (e.g., about 82.6%), lymphovascular invasion (e.g., about 69.6%), perineural invasion (e.g., about 95.7%), moderate tumor differentiation (e.g., about 69.6%) and R1 resection rate (e.g., about 21.7%). No preoperatively available clinical variable was correlated with texture features meaning that tumor texture may not be a surrogate for these variables.

Associations between tumor texture features and overall survival can be explained. Texture variables were not associated with routinely obtained tumor histology features, such as tumor differentiation, lymphovascular invasion or perineural invasion. Nevertheless, this correlation with survival can arise from the correlation between texture analysis and other tumor histologic features previously related to PDAC enhancement patterns, and reported for supporting or restraining PDAC, such as tumor fibrosis and microvascular density. (See, e.g., References 71 and 72). Relationships between radiologic features and tumor gene expression, termed radiogenomics, or between tumor texture features and tumor protein expression patterns have been described in lung and head and neck cancers. (See, e.g., References 69 and 73). For instance, Hypoxia Induced Factor-1a ("HIF-1a"), and other hypoxia markers, mainly due to low tumor perfusion, has been reported as a predictive factor of resistance to both chemotherapy and radiation as well as a poor prognostic factor in lung cancer and PDAC. (See, e.g., References 74-77). Low tumor perfusion can be responsible for HIF-1α production, which can be evaluated on tumor CT enhancement and quantified by tumor texture analysis such as contrast.

Exemplary Computed Tomography Image Texture: A Non-Invasive Prognostic Marker of Liver Recurrence in Metastatic Colorectal Cancer Exemplary Population Such exemplary study included selected patients (e.g., N=198) from 384 consecutive patients previously included in an unrelated study. (see, e.g., Reference 102). Inclusion criteria were (i) pathologically confirmed resected CRLM, (ii) available data from the pathologic analysis of the underlying non-tumoral liver parenchyma, and (iii) available preoperative conventional portal venous phase contrast-enhanced multi-detector computed tomography ("MUM") performed within 6 weeks of the operative date. Patients who experienced 90-day mortality or who had less than 24 months at exemplary follow-up were excluded. Additionally, because pathologic alterations of the non-tumoral liver parenchyma caused by HAI-FUDR are not well described, any patient who received preoperative HAI-FUDR was excluded. Finally, to obtain the most accurate FLR 3D-model, patients who underwent either local tumor ablation, more than 3 wedge resections in the FLR, or had no visible tumor on preoperative imaging were excluded.

Exemplary Data and Outcomes

Demographics, preoperative data (e.g., co-morbidities, primary tumor features, neoadjuvant chemotherapy, portal vein embolization ("PVE") and metastatic disease characteristics), and operative data and pathology (e.g., morbidity, extent of resection, margin status) were collected from a database. Synchronous disease was defined as a diagnosis of liver metastasis within 6 months of the primary colorectal tumor diagnosis. Neoadjuvant chemotherapy was defined as any systemic chemotherapy administered within 6 months of liver resection. The extent of liver resection was classified as major (e.g., 3 or more hepatic segments) or minor, as well as bilateral (e.g., resections involving both hemi-livers) or unilateral. Perioperative morbidity was prospectively recorded in the exemplary database using a grading system consistent with the "Common Terminology Criteria for Adverse Events Version 4.0". (See, e.g., Reference 103). Major morbidity was defined as any complication greater than grade II.

Postoperative radiographic monitoring was generally performed every 3 to 6 months. Adjuvant therapy was offered at the discretion of the multidisciplinary team and consisted of systemic chemotherapy alone or combined with HAI-FUDR. Recurrence was defined as any sign of recurrent CRC, confirmed either by biopsy, or unequivocal cross-sectional imaging evidence with or without elevated carcinoembryonic antigen ("CEA") level. Hepatic recurrence was defined as any recurrence observed in the liver whether confined to the liver or not.

Exemplary Pathology

Pathology of the non-tumoral liver parenchyma had been re-assessed by a pathologist as part of a previously reported study. (See. e.g., Reference 19). Hematoxylin and eosin stained slides prepared from routinely processed tissue samples were reviewed by a pathologist blinded to the patients' chemotherapy history or clinical outcome. Patients were considered to have steatosis if about 5% or greater of the examined parenchyma was involved. Steatohepatitis was defined as an overall nonalcoholic fatty liver disease activity score of 4 or greater, graded based on the Kleiner-Brunt histologic scoring system. (See, e.g., Reference 104). Sinusoidal injury was scored from 0 to 3 based on the Rubbia-Brandt grading system. (See, e.g., Reference 105). Patients with a score of 1 or greater were considered to have sinusoidal injury. These characteristics from the resected underlying non-tumoral liver were assumed to be similar in the non-resected remnant liver, extracted from preoperative CT and assessed by TA.

The same cohort of patients also had the tumor re-assessed by a pathologist as part of a study looking at the predominant histologic response patterns in colorectal liver metastases. (See, e.g., Reference 106). Necrosis, fibrosis and acellular mucin were seen in tumor specimens treated with neoadjuvant chemotherapy. However, they were also present in patients without preoperative treatment. Hematoxylin and eosin stained tumor slides were re-reviewed and pathologic response was defined as the summation of percentage necrosis, fibrosis and acellular mucin. A median of 3 slides per tumor were analyzed; typically one per centimeter of tumor diameter. Fibrosis >40% had the greatest prognostic significance and can be associated with increased survival, so the same threshold was used for this study. These tumor characteristics, both for patients with and without preoperative chemotherapy, were recorded in order to correlate with the texture analysis features extracted from the preoperative CT scans.

Exemplary CT Acquisition

Each included patient had undergone a conventional portal venous phase contrast-enhanced CT imaging scan within 6 weeks prior to surgery. In patients who received a neoadjuvant chemotherapy, the post-treatment CT was used for TA. In patients undergoing a preoperative PVE, the pre-PVE CT was used for TA because PVE changes the appearance of parenchyma in CT imaging and the effect of PVE on results of TA were not examined.

Exemplary Image Processing

Figure 12:
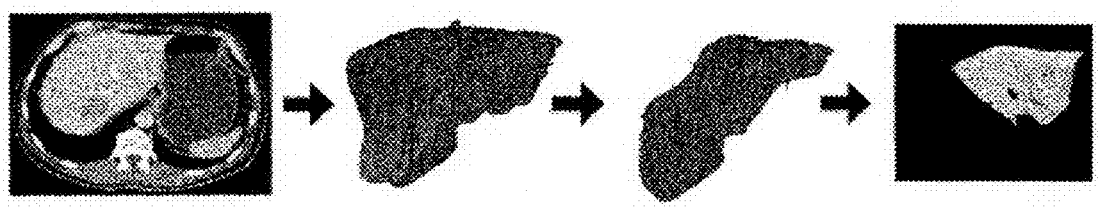
FIG. 12 is a set of exemplary images illustrating imaging processing according to an exemplary embodiment of the present disclosure.

Images were transferred from the picture archiving and communication system to a workstation for image processing. Standard image processing procedures were used to segment the liver parenchyma from surrounding structures. Liver, tumors, vessels and bile ducts were semi-automatically segmented, and a 3D model was generated using Scout Liver (e.g., Pathfinder Technologies Inc., Tennessee). The performed liver resection was virtually drawn on the 3D model of the liver. Transection lines to generate the FLR were based on postoperative imaging and/or resection margin width from pathology analysis. (See, e.g., FIG. 12). The CT image volume was clipped using the 3D models of the FLR, and hepatic and portal veins to create an image volume containing only the parenchyma of the FLR. A second image volume was created containing only the index tumor. FLR volume was defined as the percentage of remaining functional liver volume compared to the total preoperative functional liver volume.

Exemplary Texture Analysis

Figure 13:
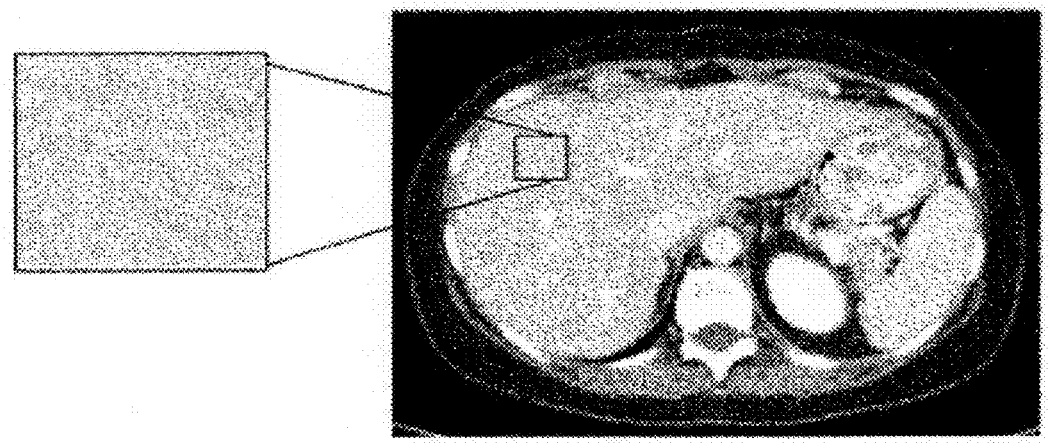
FIG. 13 is an exemplary image showing the variation in pixel density according to an exemplary embodiment of the present disclosure.

FIG. 13 illustrates the variation at the pixel level in a hepatic CT scan according to an exemplary embodiment of the present disclosure. Variation in pixel intensity can be measured statistically with a GLCM. (See, e.g., References 107 and 108). GLCM can compare gray-level brightness of neighboring pixels in an image. GLCM statistics were generated with automated software developed by a computer scientist (e.g., ALS). (See, e.g., Reference 17). These standard imaging features represent heterogeneity, with each statistic mathematically weighting aspects of heterogeneity differently. Some features, for example, place greater emphasis on image contrast. There can be 22 available GLCM features; however, five were chosen that can be considered the most discriminatory. (See, e.g., Reference 109).

Exemplary Contrast: Measure of local gray-level variation. If neighboring pixels can be similar, contrast can be very low. Contrast can be zero for a constant image with range from 0 to the size of the GLCM matrix, typically [0, 49] for CT images.

Exemplary Correlation: Measure of brightness interdependence on neighboring pixels with range [−1,1] for perfectly positively or negatively correlated image.

Exemplary Energy: Measure of local homogeneity with range [0,1] where energy can be one for a constant image.

Exemplary Entropy: Measure of randomness (e.g., or disorder) in brightness variation. Entropy can be lower for smooth textures where entropy can be zero for a constant image.

Exemplary Homogeneity: Measure of the uniformity with range [0,1] where one can be a perfectly homogenous image. High homogeneity refers to textures with spatially repetitive gray values.

Exemplary Statistical Analysis

Descriptive and comparative statistics were performed using SPSS. A P value of 0.05 or less was considered significant. Univariable OS and HDFS analysis was carried out with Kaplan-Meier statistics (e.g., log-rank test) for all preoperative clinical and texture variables and any variable with p<0.1 was included in a subsequent multivariable model. The OS event was death from any cause and any patient alive at last follow-up was censored. HDFS was defined as the interval from operation to any hepatic recurrence (e.g., regardless of other sites of recurrence). To test the statistical relationship between clinical and texture variables and outcomes, Spearman's correlation coefficients were calculated and presented in a correlation matrix. Dependence was ruled out with a correlation coefficient (e.g., absolute q value) of less than about 0.7. In the case of dependence between two or more variables, only the variable the most correlated with OS and HDFS, or the most clinically relevant variable, was included in multivariable analysis (e.g., Cox-regression model) using backward selection. Results from the Cox proportional hazards models were reported as hazard ratios ("HRs"), with 95% confidence intervals ("CIs"), and P values.

Exemplary Results

Exemplary Perioperative Data

Figure 14:
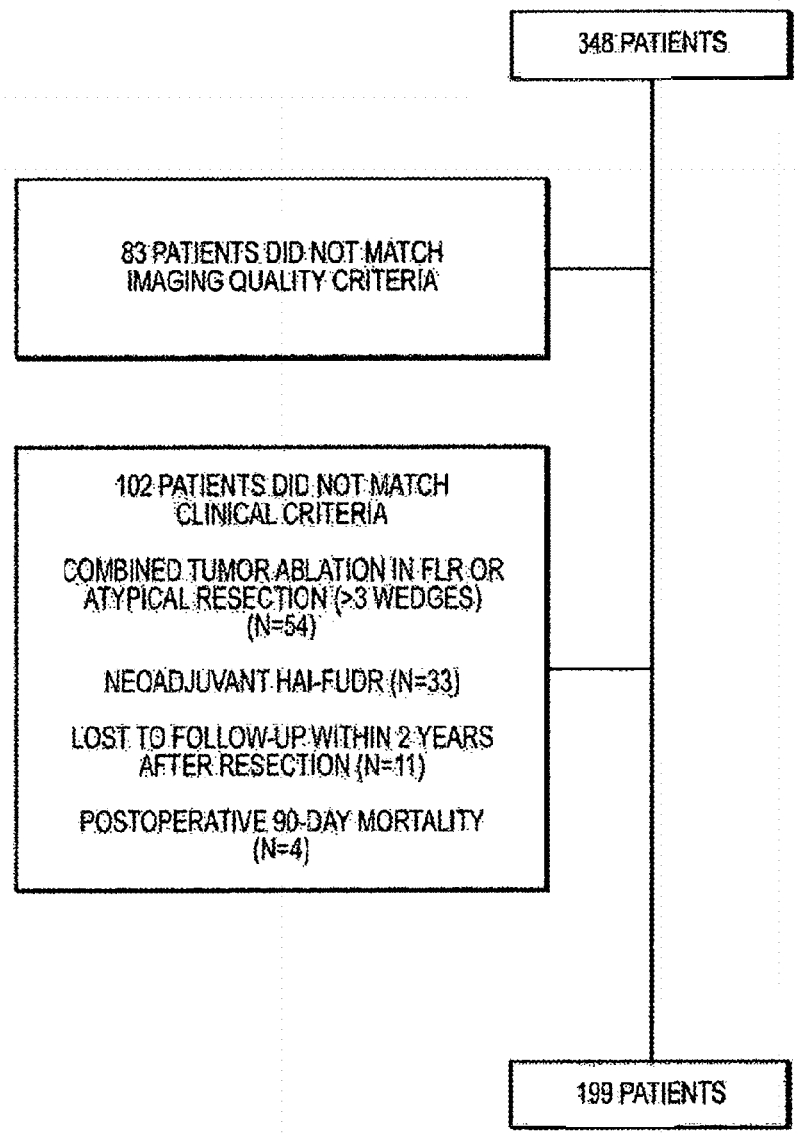
FIG. 14 is an exemplary flow chart showing patient selection according to an exemplary embodiment of the present disclosure.

Overall, 198 patients who underwent liver resection for metastatic CRC between April 2003 and March 2007 were included in the study. (See, e.g., FIG. 14). Demographic and clinicopathological factors are listed in Table 10 below. About two-thirds of patients (e.g., n=118) had a low (e.g., 0-2) clinical risk score ("CRS"). One hundred twenty-two patients (e.g., 61.3%) received neoadjuvant chemotherapy (e.g., FOLFOX, n=61; FOLFIRI, n=23; FOLFIRINOX, n=23; 5-FU alone, n=15). Additionally, 33 patients (e.g., 16.6%) received concomitant targeted therapy (e.g., bevacizumab, n=32; cetuximab, n=1). The median duration of neoadjuvant chemotherapy was four months (e.g., range, 1-58). The median interval between cessation of chemotherapy and liver resection was 8 weeks (e.g., range, 2-24). One hundred twenty patients (e.g., 60.3%) underwent a major liver resection. Major morbidity rate was 12.1% (e.g., n=24). The rate of margin negative (e.g., R0) resection was 86.4% (e.g., n=171). Median FLR volume was 70.0% (e.g., range, 17.2-99.0). Underlying non-tumoral liver abnormalities reassessed by a pathologist included steatosis (e.g., n=68; 34.3%), sinusoidal injury (e.g., n=26, 13.1%), and steatohepatitis (e.g., grade ≥4) (e.g., n=7, 3.5%). On pathologic review of the tumor, total response >75% was observed in 38 patients (e.g., 19%) and was the summation of the combined percent necrosis, fibrosis, and mucin. 24 patients (e.g., 12%) had tumors with fibrosis >40%. Adjuvant chemotherapy after liver resection was administered to 152 patients (e.g., 76.8%), of which about 40% (e.g., n=62) received systemic chemotherapy along with HAI-FUDR.

TABLE 10

Demographic, Clinicopathologic, and Texture Feature Details

| Demographics/Characteristics | Value (N = 198) |
|---|---|
| Demographics | |
| Sex, male, n (%) | 118 (60) |
| Age, years (range) | 61 (30-88) |
| Major Comorbidity, n (%) | 110 (56) |
| Body Mass Index, kg/m$^2$ (range) | 26.8 (17.2-44.3) |
| Preoperative Characteristics | |
| Node-positive Primary Tumor, n (%) | 69 (35) |
| Synchronous CRLM, n (%) | 112 (57) |
| Multiple Metastases, n (%) | 114 (58) |
| CRS (score 0-2), n (%) | 118 (60) |
| CEA > 200, n (%) | 3 (1.5) |
| Maximal Tumor Size, cm (±SD) | 3.5 ± 2.6 |
| Bilobar Disease, n (%) | 86 (43) |
| Extrahepatic Disease, n (%) | 17 (9) |
| Neoadjuvant Chemotherapy, n (%) | 122 (61) |
| Preoperative PVE, n (%) | 23 (12) |
| Pathology of Non-tumoral Liver, n (%) | |
| Steatosis | 68 (34) |
| Sinusoidal Dilation | 26 (13) |
| Steatohepatitis (grade ≥ 4) | 7 (4) |
| Pathology of Index Tumor | |
| Total Response > 75%, n (%) | 38 (19) |
| Tumor Fibrosis > 40%, n (%) | 24 (12) |
| Percent Necrosis, median % (range) | 30% (0-90) |
| Percent Fibrosis, median % (range) | 10% (0-100) |
| Percent Mucin, median % (range) | 0 (0-100) |
| Texture Features (mean ± SD) | |
| FLR Correlation | 0.028 ± 0.025 |
| FLR Homogeneity | 0.719 ± 0.064 |
| FLR Contrast | 0.895 ± 0.375 |
| FLR Energy | 0.239 ± 0.133 |
| FLR Entropy | 0.469 ± 0.157 |
| Tumor Correlation | 0.274 ± 0.156 |
| Tumor Homogeneity | 0.629 ± 0.077 |
| Tumor Contrast | 1.780 ± 0.843 |
| Tumor Energy | 0.111 ± 0.088 |
| Tumor Entropy | 0.052 ± 0.065 |

Figure 15:
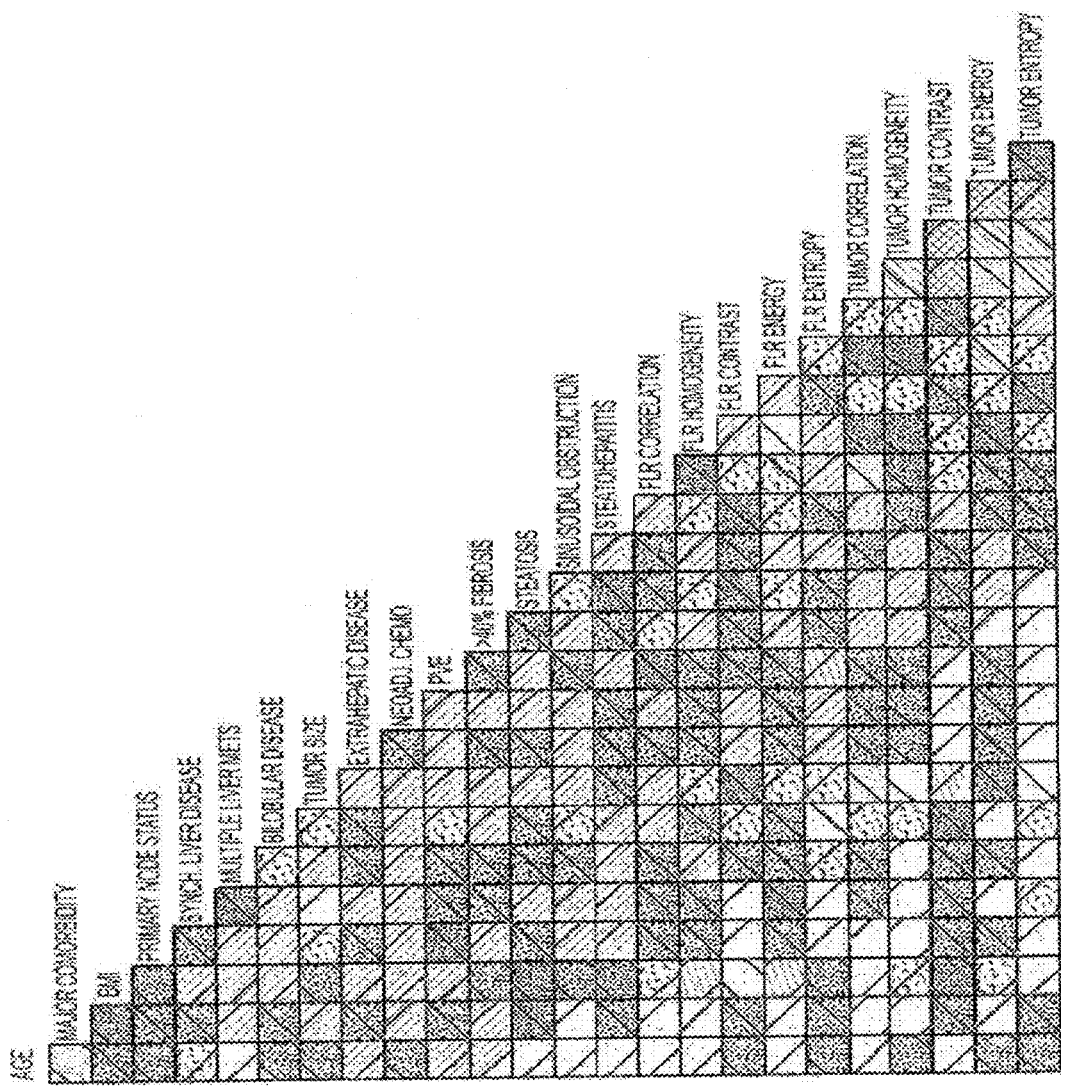
FIG. 15 is an exemplary Spearman correlation matrix for preoperative clinical, pathology and texture variables according to an exemplary embodiment of the present disclosure.

Abbreviations:
CRLM, colorectal liver metastases;
CRS, clinical risk score;
CEA, carcinoembryonic antigen;
PVE, portal vein embolization;
FLR, future liver remnant The Spearman correlation matrix demonstrating the statistical relationship between perioperative and texture variables is shown in FIG. 15. FLR homogeneity, FLR contrast, and FLR energy correlated with BMI (e.g., about p<0.001), steatosis (e.g., about p<0.05), and steatohepatitis (e.g., about p<0.05). Tumor texture variables correlated with tumor size (e.g., about p<0.05).

Exemplary Overall Survival

Median OS in the whole cohort was 75.7 months (e.g., 95% CI 60.7-90.7). After a median follow-up of 75 months (e.g., range 3.8-131.9), 90 patients (e.g., 45.5%) were alive, of which 70 had no evidence of disease. In univariable analysis, tumor size, extrahepatic disease, neoadjuvant chemotherapy, tumor fibrosis >40%, FLR homogeneity, FLR contrast, FLR energy, FLR entropy, tumor correlation, tumor homogeneity, and tumor contrast (e.g., Table 11 below, p<0.1) were significantly associated with OS and subsequently included in a multivariable Cox-regression model. Following Spearman's test for dependence (e.g., FIG. 15), FLR homogeneity and FLR contrast were highly correlated with FLR energy, and therefore removed from the model. FLR energy and FLR entropy were combined into a single linear predictor and included in the multivariable model. Tumor correlation and tumor contrast were similarly combined and included in the multivariable model. Neoadjuvant chemotherapy, extrahepatic disease, tumor fibrosis >40%, FLR energy/entropy, and tumor correlation/contrast were independently associated with OS (e.g., Table 12). Additional operative (e.g., blood loss, blood product transfusion, operative time) and outcome variables (e.g., complications, major complications, 90-day mortality, ICU admission) were not significantly correlated with OS (e.g., or HDFS) and therefore not shown.

TABLE 11

Predictors of Overall Survival and Recurrence in Univariable Analysis

| | Overall Survival (N = 198) | | | Hepatic Disease-Free Survival (N = 198) | | |
|---|---|---|---|---|---|---|
| Variable | Median (95% CI) (Months) | HR (95% CI) | P | 3YS (%) | HR (95% CI) | P |
| Demographics | | | | | | |
| Sex (male) | 82.0 (63.0-101.0) | | 0.184 | 68 (34) | | 0.341 |
| Age | | 1.00 (0.99-1.02) | 0.963 | | 0.99 (0.97-1.01) | 0.19 |
| Major Comorbidity | 80.7 (54.9-106.5) | | 0.531 | 62 (31) | | 0.759 |
| Body Mass Index | | 0.97 (0.94-1.01) | 0.177 | | 0.97 (0.92-1.01) | 0.13 |

TABLE 11-continued

Predictors of Overall Survival and Recurrence in Univariable Analysis

| | Overall Survival (N = 198) | | | Hepatic Disease-Free Survival (N = 198) | | |
|---|---|---|---|---|---|---|
| Variable | Median (95% CI) (Months) | HR (95% CI) | P | 3YS (%) | HR (95% CI) | P |
| Preoperative Characteristics | | | | | | |
| Node-positive Primary Tumor | 80.7 (55.2-106.2) | | 0.947 | 37 (19) | | 0.777 |
| Synchronous CRLM | 80.7 (51.7-109.8) | | 0.349 | 59 (30) | | 0.648 |
| Multiple Metastases | 67.6 (57.4-77.8) | | 0.118 | 57 (29) | | 0.066 |
| CEA >200 | 26.8 (—) | — | 0.288 | — | | 0.783 |
| Maximal Tumor Size | | 1.08 (1.02-1.15) | 0.014 | | 1.02 (0.94-1.11) | 0.59 |
| Bilobar Disease | 72.5 (61.7-83.4) | | 0.588 | 45 (23) | | 0.749 |
| Extrahepatic Disease | 36.2 (28.6-43.8) | | 0.003 | 4 (2) | | 0.004 |
| Neoadjuvant Chemotherapy | 65.3 (56.3-74.4) | | 0.003 | 58 (29) | | 0.146 |
| Preoperative PVE | 75.7 (40.8-110.5) | | 0.799 | 8 (4) | | 0.016 |
| Pathology | | | | | | |
| Steatosis | 98.9 (62.3-135.5) | | 0.121 | 40 (20) | | 0.561 |
| Sinusoidal Dilation | 75.3 (54.3-96.3) | | 0.783 | 14 (7) | | 0.464 |
| Steatohepatitis (grade ≥4) | 68.1 (30.5-105.6) | | 0.680 | 4 (2) | | 0.871 |
| Tumor Total Response >75% | 108.5 (79.4-137.6) | | 0.119 | 22 (11) | | 0.584 |
| Tumor Fibrosis >40% | — | | 0.031 | 15 (8) | | 0.059 |
| Tumor Percent Necrosis | | 0.99 (0.99-1.01) | 0.865 | | 1.00 (0.99-1.01) | 0.899 |
| Tumor Percent Fibrosis | | 0.99 (0.98-1.00) | 0.146 | | 0.99 (0.98-1.00) | 0.192 |
| Tumor Percent Mucin | | 0.98 (0.99-1.01) | 0.592 | | 1.00 (0.98-1.01) | 0.672 |
| Texture Features | | | | | | |
| FLR Correlation | | 4.76 (0.01-4347) | 0.654 | | 3.12 (0.00-18546) | 0.797 |
| FLR Homogeneity | | 18.73 (1.29-271.1) | 0.032 | | 70.24 (3.56-1384) | 0.005 |
| FLR Contrast | | 0.56 (0.31-1.01) | 0.055 | | 0.50 (0.25-1.00) | 0.050 |
| FLR Energy | | 3.20 (0.93-11.01) | 0.065 | | 6.36 (1.74-23.29) | 0.005 |
| FLR Entropy | | 0.20 (0.06-0.72) | 0.014 | | 0.16 (0.04-0.72) | 0.017 |
| Tumor Correlation | | 5.24 (1.58-17.42) | 0.007 | | 6.02 (1.51-24.03) | 0.011 |
| Tumor Homogeneity | | 8.47 (1.14-63.10) | 0.037 | | 5.23 (0.46-59.44) | 0.183 |
| Tumor Contrast | | 0.73 (0.58-0.92) | 0.009 | | 0.78 (0.60-1.03) | 0.078 |
| Tumor Energy | | 1.81 (0.37-8.84) | 0.463 | | 1.31 (0.17-10.24) | 0.796 |
| Tumor Entropy | | 5.61 (0.51-61.54) | 0.158 | | 0.54 (0.02-16.03) | 0.722 |

Figure 16A:
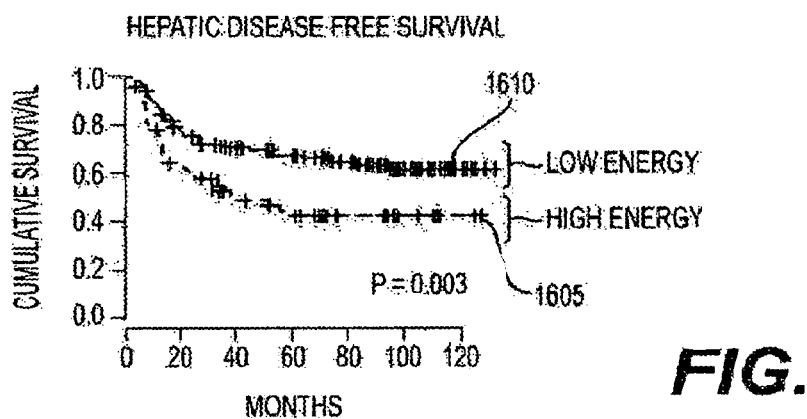
FIG. 16A is an exemplary graph illustrating a Kaplan-Meier curve of hepatic disease free survival by patients stratified by FLR energy according to an exemplary embodiment of the present disclosure.

Abbreviations:
CRLM, colorectal liver metastases;
CEA, carcinoembryonic antigen;
PVE, portal vein embolization;
FLR, future liver remnant Exemplary Hepatic Disease-Free Survival At last follow-up, the overall recurrence rate was 66.7% (e.g., n=132), with liver involvement in 81 patients (e.g., 61.4%). Recurrence was confined to the liver in 43 patients (e.g., 53.1%). Median overall recurrence-free survival was 22 months (e.g., 95% CI 14.0-30.6) and median HDFS was not reached. In the univariable analysis, multiple metastases, preoperative PVE, extrahepatic disease, tumor fibrosis >40%, FLR energy, and FLR entropy, tumor correlation, and tumor contrast (e.g., Table 11, p<0.1) were significantly associated with HDFS (e.g., as above, FLR homogeneity and FLR contrast were excluded) and subsequently included in a multivariable Cox-regression model. Extrahepatic disease, FLR energy/entropy, and tumor correlation/contrast were identified as independently associated with HDFS. (See, e.g., Table 12 below). There was no association with extrahepatic recurrence. After adjustment for other independent HDFS predictors, FLR energy, dichotomized using its mean (e.g., mean=0.239) into 'high energy' (e.g., line 1605) and 'low energy' (e.g., line 1610) groups, facilitating stratification of patients between two distinct risk groups of liver recurrence. (See, e.g., FIG. 16A). Patients with FLR energy >0.239 (e.g., n=68) had a significantly higher cumulative risk of liver recurrence (e.g., HR=1.91; 95% CI=0.23-2.97; p=0.004). The cumulative hazard of liver recurrence at 24 months after CRLM resection was 41% (e.g., 95% CI=29-52) in the "high-risk FLR" group, defined as FLR energy >0.239, and was 25% (e.g., 95% CI=17-32) in the "low-risk FLR" group.

Exemplary Impact of Adjuvant HAI-FUDR Therapy

Figure 16B:
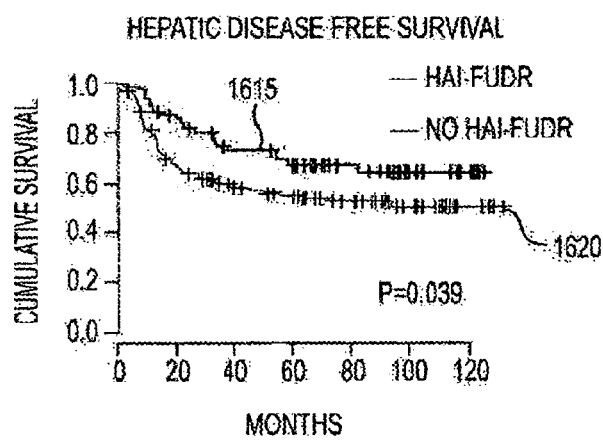
FIG. 16B is an exemplary graph illustrating the Kaplan-Meier curve of the hepatic disease free survival by patients stratified by adjuvant therapy according to an exemplary embodiment of the present disclosure.
Figure 16C:
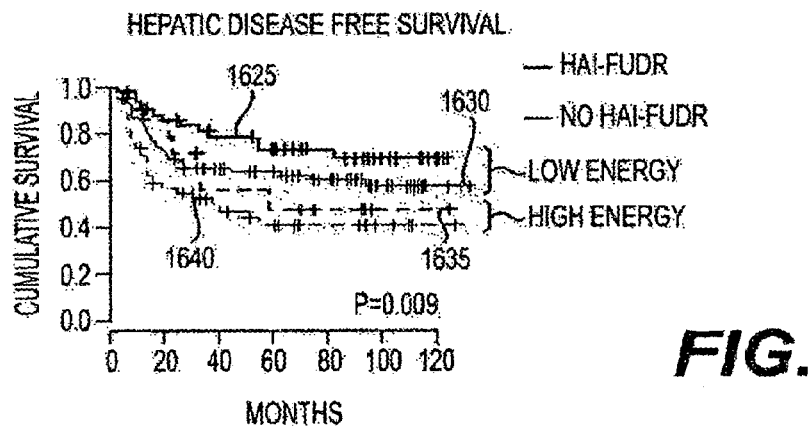
FIG. 16C is an exemplary graph illustrating the Kaplan-Meier curve of the hepatic disease free survival by patients stratified by the adjuvant therapy and FLR energy according to an exemplary embodiment of the present disclosure.

The administration of adjuvant HAI-FUDR therapy was associated with improved HDFS (e.g., HR=0.591; 95% CI=0.36-0.98; p=0.034). (See, e.g., HAI-FUDR 1615 and No HAO-FUDR 1620 in the graph of FIG. 16B). FLR energy, dichotomized using its mean, and grouped by HAI-FUDR, stratified patients into distinct risk groups of recurrence. (See, e.g., low energy HAI-FUDR 1625 and low energy No HAO-FUDR 1630 and high energy HAI-FUDR 1635 and high energy No HAO-FUDR 1640 in the graph of FIG. 16C). The administration of pump therapy did not alter the strength of association between FLR energy and HDFS in subset analysis (e.g., HAI-FUDR HR=111.2; 95% CI=0.87-14270, no HAI-FUDR HR=3.83; 95% CI=0.94-15.67; p=0.227).

Exemplary Discussion

Many predictive scores and prognostic models of survival after CRLM resection have been published based on preoperative or perioperative clinical variables. The exemplary shows that TA on preoperative CT images from a large consecutive series provides information about the tumor and liver parenchyma that can be associated with the risk of hepatic recurrence.

While the exact mechanism of intrahepatic recurrence after liver resection for CRLM can be unknown, it can likely be that environmental changes in the FIR and tumor can be related to this risk. In exemplary study, the role of TA in predicting survival and hepatic recurrence in a group of patients undergoing resection of CRLM was investigated. These findings suggest that the texture of the tumor and non-tumoral liver can contribute equally to the risk of intrahepatic CRLM recurrence.

In a multivariable analysis that included standard preoperative clinical variables, tumoral and non-tumoral texture features were associated with OS, FLR texture reached statistical significance for HDFS and a trend was noted for tumor texture features. Within the tumor, homogenous tumors demonstrated worse outcome, which can be consis-

TABLE 12

Results of Multivariable Cox Analysis of Predictors of Survival and Recurrence

| Variable | Overall Survival (HR, 95% CI) | P | Hepatic Disease-Free Survival (HR, 95% CI) | P |
|---|---|---|---|---|
| Full Model | | | | |
| Maximal Tumor Size, cm | 1.02 (0.95-1.10) | 0.515 | | |
| Multiple Metastases | | | 1.44 (0.90-2.32) | 0.131 |
| Extrahepatic Disease | 2.19 (1.15-4.16) | 0.036 | 2.25 (1.16-4.34) | 0.016 |
| Preoperative PVE | | | 1.62 (0.86-3.04) | 0.136 |
| Neoadjuvant Chemotherapy | 1.83 (1.20-2.78) | 0.005 | | |
| Tumor Fibrosis > 40% | 0.45 (0.21-0.98) | 0.045 | 0.42 (0.17-1.05) | 0.063 |
| FLR Energy/Entropy | 2.19 (1.09-4.40) | 0.028 | 1.94 (1.02-3.69) | 0.044 |
| Tumor Correlation/Contrast | 2.08 (0.97-4.45) | 0.081 | 2.2 (1.02-5.02) | 0.045 |
| Final Model | | | | |
| Extrahepatic Disease | 2.25 (1.21-4.17) | 0.010 | 2.39 (1.25-4.57) | 0.008 |
| Neoadjuvant Chemotherapy | 1.84 (1.21-2.80) | 0.005 | | |
| Tumor Fibrosis > 40% | 0.46 (0.21-1.00) | 0.049 | 0.45 (0.18-1.12) | 0.086 |
| FLR Energy/Entropy | 2.15 (1.08-4.29) | 0.029 | 2.21 (1.21-4.03) | 0.010 |
| Tumor Correlation/Contrast | 2.35 (1.21-4.55) | 0.013 | 2.09 (0.95-4.58) | 0.066 |

Abbreviations:
FLR, future liver remnant tent with trends observed in another study. (See, e.g., Reference 100). Homogeneous tumor attenuation, and sharp tumor-parenchyma interface (e.g., by radiographic assessment) can predict survival and pathologic response (e.g., scored based on residual tumor cells) following neoadjuvant chemotherapy. (See, e.g., Reference 101). Tumor fibrosis >40% and tumor texture were associated with overall survival (e.g., about p<0.05) and trends in HDFS (e.g., about p<0.10).

For example, the texture parenchyma shows that higher FLR energy can correspond to shorter survival. Thus, high FLR energy can correspond to a homogeneous FLR with limited gray pixel variation on CT imaging. In the current cohort, FLR energy varied from about 0.095 to about 0.988, with a mean of about 0.239, demonstrating a large variability in FLR appearance on portal venous phase CT. Using FLR energy as a dichotomized variable in a preoperative multivariable model, facilitated stratification of patients into two distinct groups. (See, e.g., FIG. 16A). Patients with "high-risk FLR," or FLR energy values above the mean, had shorter OS and HDFS. Thus, high FLR energy can suggest the presence of occult metastases or other underlying parenchymal changes associated with risk of recurrence. Structural changes (e.g., angiogenesis, extracellular matrix remodeling) in the remote and peritumoral non-tumoral liver parenchyma have been described in patients with CRLM. (See, e.g., References 110-112). Exosomes derived from pancreatic ductal adenocarcinoma can induce changes in the extracellular matrix, providing a favorable niche for metastasis development. (See, e.g., References 113 and 114). These parenchymal modifications involved in prometastatic mechanisms and metastatic tumor growth might be occurring in the FLR already at the time of resection and detected using preoperative TA. There was no association between FLR energy and extrahepatic disease, lending further support to this theory.

Texture variables of the FLR correlated with some clinical variables. Analysis using steatosis and steatohepatitis showed slight correlations with FLR contrast, energy, and homogeneity (e.g., about p<0.05). However, underlying steatosis and steatohepatitis were not associated with OS and HDFS in univariable analysis. Thus, while steatosis and steatohepatitis can contribute to alterations in the appearance of the FLR, they could not account for differences in OS and HDFS in the exemplary patient population. Validation of such assumptions, however, needs further investigation, including pairing preoperative FLR TA with specific pathologic assessment of regions of the FLR.

An exemplary analysis of the exemplary institutional data has shown a benefit of the use of adjuvant HAI-FUDR for patients after CRLM resection. (See, e.g., Reference 7). In the exemplary study, about 40% of patients (e.g., n=62) who received adjuvant chemotherapy also received HAI-FUDR. In this cohort, adjuvant HAI-FUDR can modify the postoperative risk of liver recurrence, and can be in line with previous randomized clinical trials that reported the positive impact of HAI-FUDR on HDFS, as compared to surgery alone and adjuvant systemic chemotherapy. (See, e.g., References 84 and 115). Preoperative FLR energy can further stratify patients into low- and high-risk groups for recurrence. HAI-FUDR was associated with improved HDFS regardless of high or low energy and can be a fruitful treatment strategy for patients at high risk of hepatic recurrence.

Extrahepatic disease was also independently associated with OS and HDFS in the exemplary study, which can be concordant with previously published results. (See, e.g., References 80, 88 and 116-118). Largest metastasis size was associated with OS in univariable analysis, in agreement with findings from previous large series (see, e.g., References 80, 87, 88, 116 and 117), but this finding did not hold in multivariable analysis. Neoadjuvant therapy was associated with a worse OS in univariable analysis. This variable was included in multivariable analysis, but the suitability for inclusion is debatable. First, neoadjuvant therapy was delivered at the discretion of the treating physician, mostly based on worrisome clinical features such as tumor size and multifocality, or the presence of extrahepatic or synchronous disease Neoadjuvant therapy delivery likely reflected the burden of metastatic disease. Second, the benefit of neoadjuvant chemotherapy is still debated and, according to a recent systematic review, appears to be limited to patients with borderline resectable tumors. (See, e.g., Reference 119).

Further, more important than the neoadjuvant approach, tumor response to neoadjuvant chemotherapy can be associated with prognosis, whereas neoadjuvant chemotherapy alone does not systematically result in tumor response. (See, e.g., Reference 120). In the exemplary dataset, the tumor response (e.g., defined as the summation of percent necrosis, fibrosis, and acellular mucin) was scored for all tumors regardless of chemotherapy status. Fibrosis >40% has been demonstrated to drive the improvement in disease specific survival observed in the subset of patients treated with neoadjuvant chemotherapy. (See, e.g., Reference 106). This variable remained true for overall survival, although total response >75% did not reach significance on univariable analysis.

Quantitative Measures of Tumor Heterogeneity for Survival Prediction of Patients with Pancreatic Ductal Adenocarcinoma Exemplary Methods Based on the observation that PDAC can have a variable appearance that can be associated with survival, PDAC texture was investigated as a prognostic factor prior to neoadjuvant chemotherapy. Texture was quantified using several intensity and directional edge-based features extracted from the tumor region, and then segmented under radiologist supervision. Fuzzy minimum-redundancy maximum-relevance (fMRMR)-based feature selection and naive Bayes classifier techniques were used in conjunction with cross-validation to evaluate feature performance for 2-year survival prediction.

Figure 17:
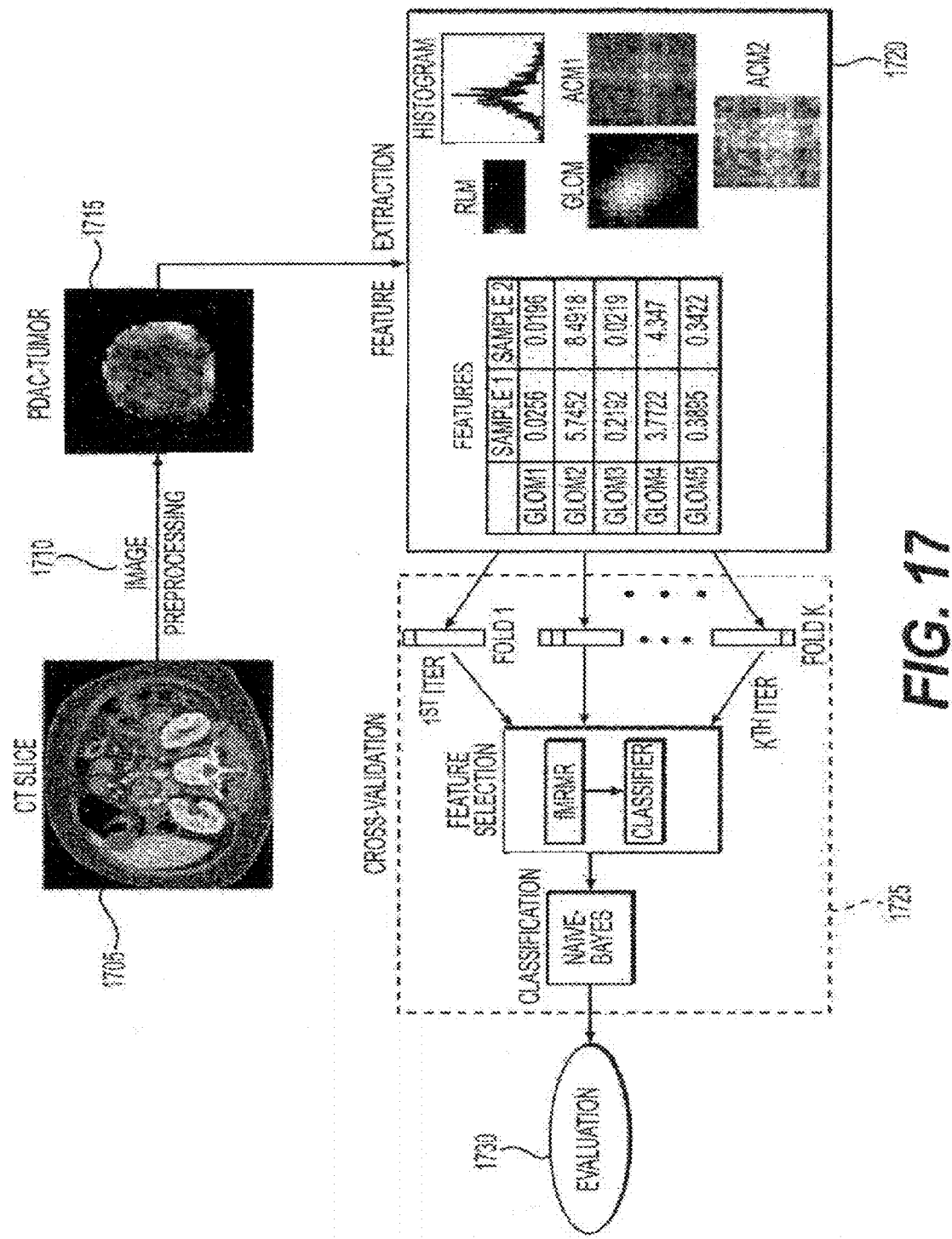
FIG. 17 is an exemplary diagram/method of the exemplary system, method and computer-accessible medium according to an exemplary embodiment of the present disclosure.

FIG. 17 shows an exemplary schematic/flow diagram of an exemplary method for evaluating a tumor according to an exemplary embodiment of the present disclosure. For example, a CT slice 1705 can be acquired, which can be processed at procedure 1710 into a PDAC-tumor image 1715. A feature extraction 1720 can be performed on the PDAC-tumor image, which can be cross-validated 1725, to be used in an evaluation at 1730.

Exemplary Study Design and Patients

Patients enrolled in a prospective clinical trial on the role of neoadjuvant chemotherapy in resectable pancreatic ductal adenocarcinoma patients were included in the exemplary retrospective analysis. (See, e.g., Reference 135). The neoadjuvent therapy was comprised of four cycles of gemcitabine dosed at 1000 mg/m$^2$ IV over 100 minutes and oxaliplatin 80 mg/m$^2$ IV over 2 hours at every 2 weeks. After neoadjuvent therapy, the patients who were eligible for resection proceeded for surgery within 2-6 weeks after adjuvent therapy and subsequently received 5 cycles of adjuvant gemcitabine (e.g., 1000 mg/m$^2$ IV over 30 minutes on days 1, 8, 15 every 4 weeks). Detailed description of patient selection and treatment characteristics of this cohort has been shown. (See, e.g., Reference 135). Of the original thirty-eight patients, three were excluded from the exemplary study due to insufficient imaging. The remaining thirty-five patients were included in the exemplary analysis. As part of the clinical trial, all patients were chemo naive, an ideal study population for texture analysis because chemotherapy changes the appearance of tumors on portal venous phase CT and would therefore include the exemplary texture analysis.

Patients received contrast-enhanced CT imaging as part of the clinical trial. The post-contrast CT images were acquired following the administration of 150 mL iodinated contrast (e.g., Omnipaque 300, GE Healthcare, New Jersey) at 4.0 mL/sec, on multidetector CT (e.g., Lightspeed 16 and VCT, GE Healthcare, Wisconsin). The scan parameters included the following: pitch/table speed=0.984-1.375/39.37-27.50 mm; autoMA 220-380; noise index 12.5-14; rotation time 0.7-0.8 ms; scan delay 80-85 s. For image analysis, axial slices reconstructed at each 2.5 mm interval were used.

Exemplary Preprocessing

Figures 18A, 18B, 18C:
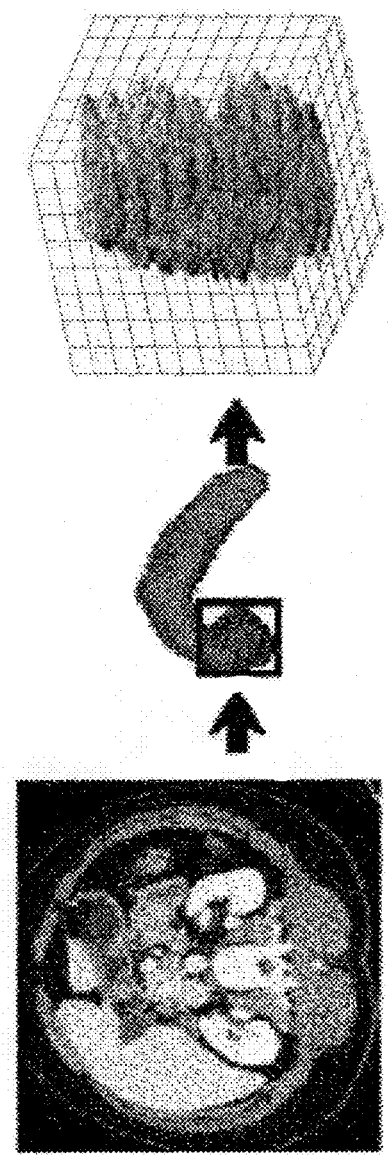
FIG. 18A-18C are exemplary images used and/or generated by the exemplary system, method and computer-accessible medium according to an exemplary embodiment of the present disclosure.

The PDAC tumor region was manually designated by an experienced radiologist, blinded to clinical outcome, using Scout Liver (e.g., Pathfinder Technologies Inc., Nashville, Tenn.). (See, e.g., FIGS. 18A-18C). For example, as shown therein, an extracted CT slice (see, e.g., FIG. 18A) can be acquired, and a 3-D view of the manually separated pancreas with a tumor can be generated. (See, e.g., FIG. 18B). The 3D view can be used to generate one or more 2D slices of the tumor. (See, e.g., FIG. 18C). Pixels affected by attenuation due to air or metal were excluded from the analysis with thresholding using the following criteria:

$$I_o(x,y)=0, \text{ if } I_o(x,y) \leftarrow -100 \text{ HU or } I_o(x,y) > 150 \text{ HU}.$$

The intensity of tumor region was normalized using the following equation:

$$I_n = (I_o - \min_o)\frac{(\max_n - \min_n)}{\max_o - \min_o} + \min_n, \quad (1)$$

where $I_o$ can be the original image with maximum and minimum intensity $\max_o$ and $\min_o$, respectively; $I_n$ represents the normalized image with maximum and minimum intensity $\max_n$ and $\min_n$, respectively. $\max_n=1$ and $\min_n=0$ were considered.

FIGS. 19A and 19B show exemplary images of CT slices containing tumor regions of a patient having an overall survival rate that is greater than and less than two years, respectively. FIGS. 19C and 19D illustrate images that show the corresponding gradient-magnitude of FIGS. 19A and 19B, respectively, and FIGS. 19E and 19F show the corresponding gradient angle for FIGS. 19A and 9B, respectively. FIGS. 19G and 19H show the corresponding LBP of FIGS. 19A and 19B, respectively, and FIGS. 19I and 19J show FIGS. 19A and 19B displayed by converting the data into gray levels.

Figure 20A:
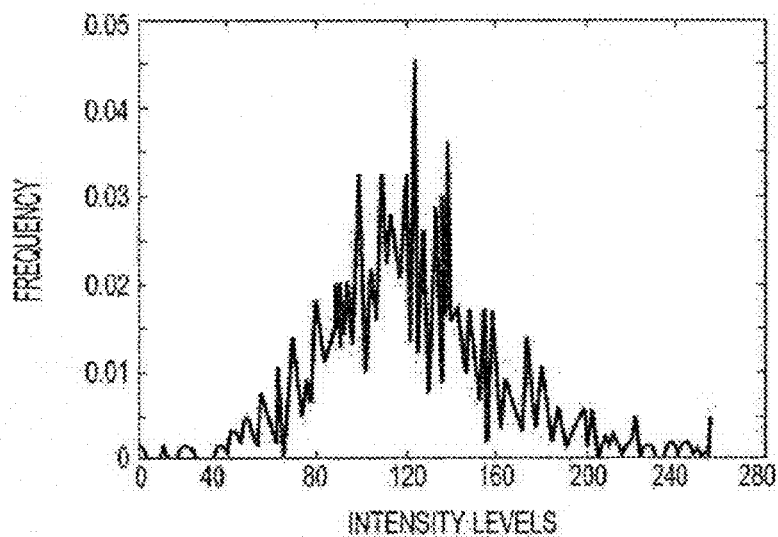
FIGS. 20A and 20B are exemplary histograms according to an exemplary embodiment of the present disclosure.
Figure 20B:
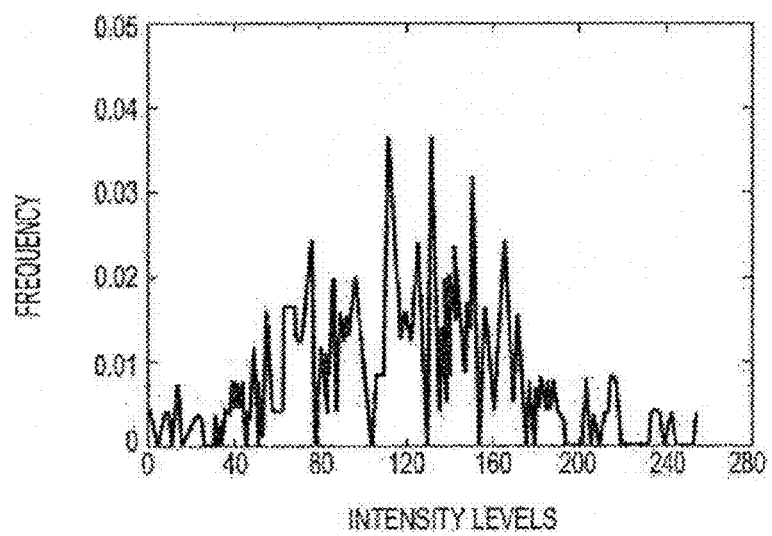
Figure 20I:
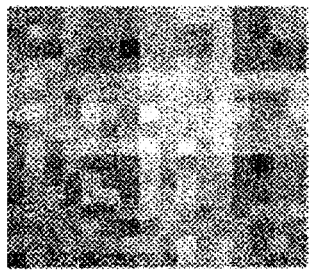
FIGS. 20C-20J are exemplary texture images according to an exemplary embodiment of the present disclosure.
Figure 20G:
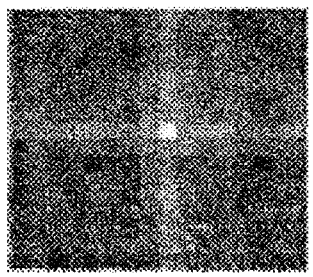
Figure 20E:
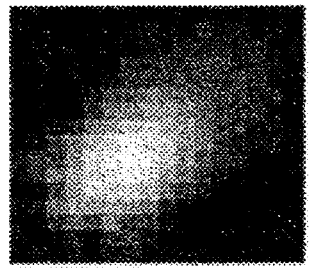
Figure 20C:
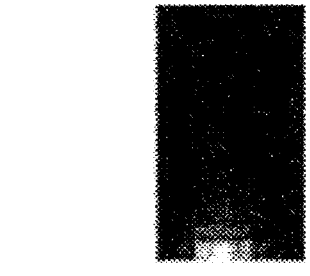
Figure 20J:
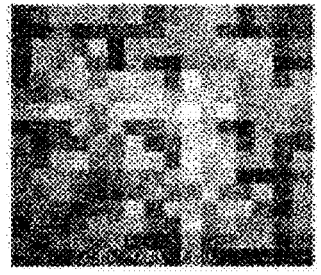
Figure 20H:
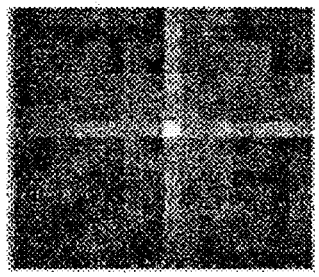
Figure 20F:
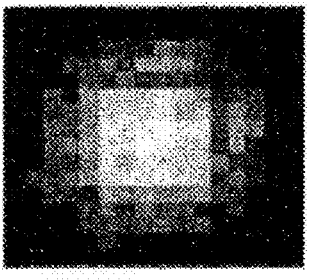
Figure 20D:
Figure 21:
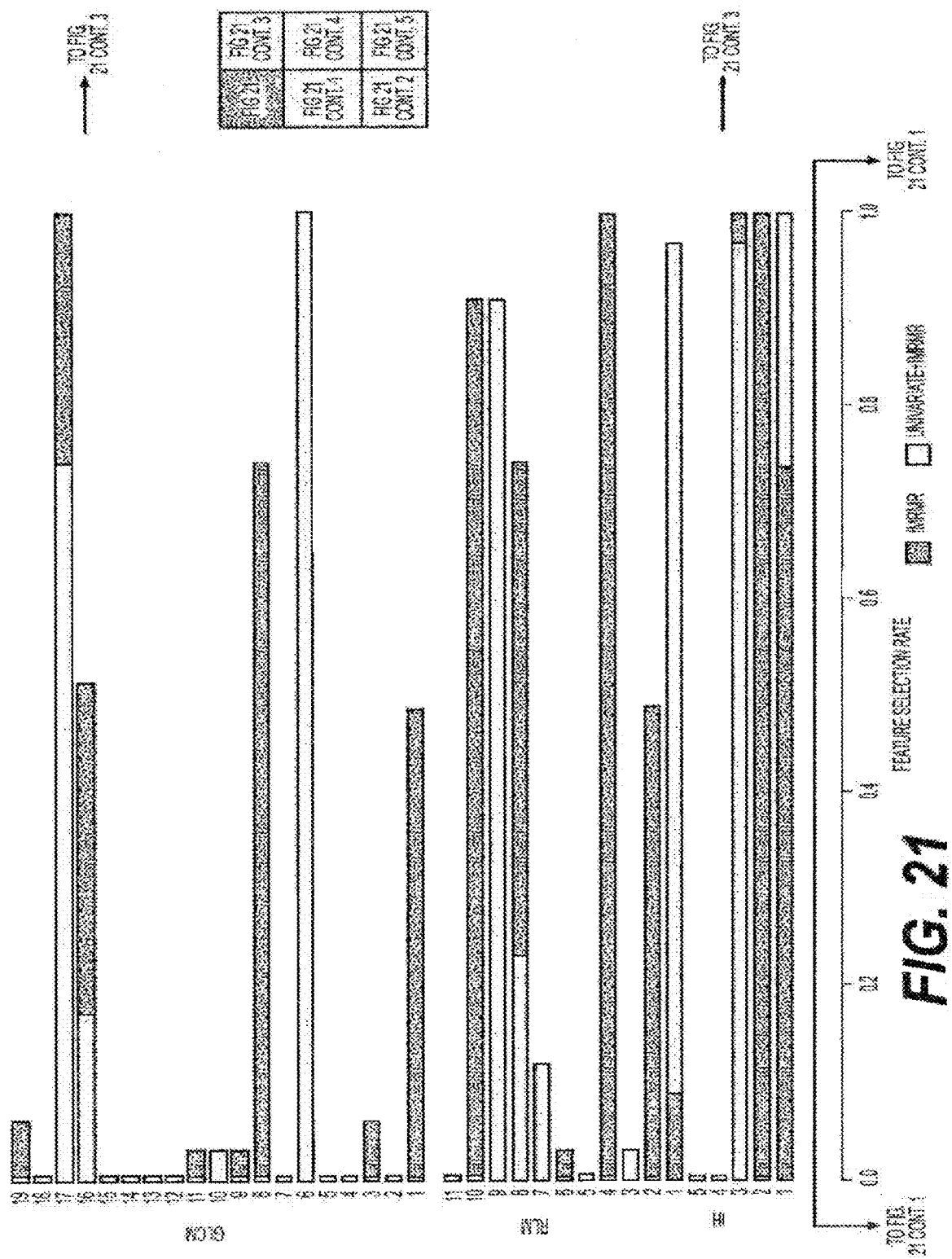
FIG. 21 is an exemplary diagram of the selection of feature rates when individual feature sets are evaluated according to an exemplary embodiment of the present disclosure.
Figure 21:
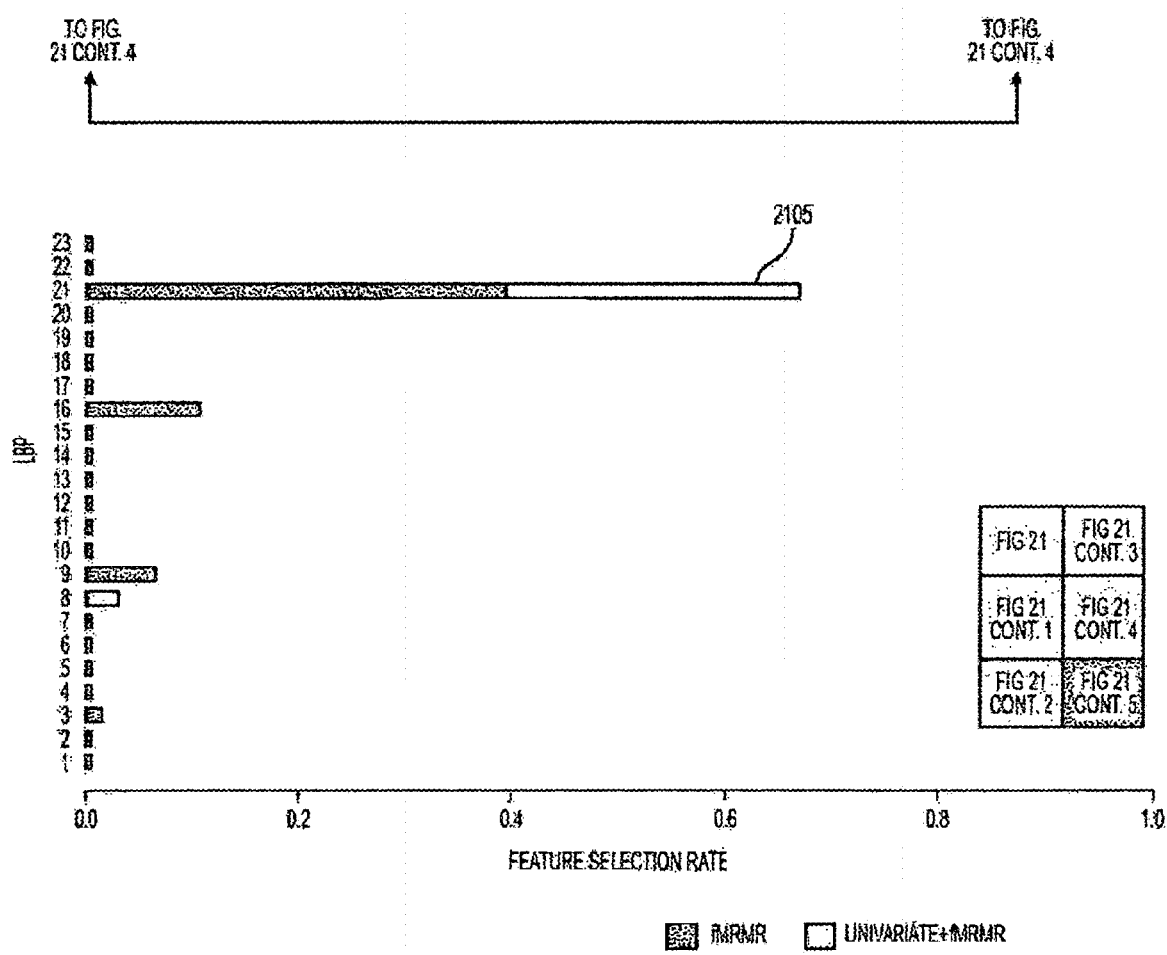
Figure 22A:
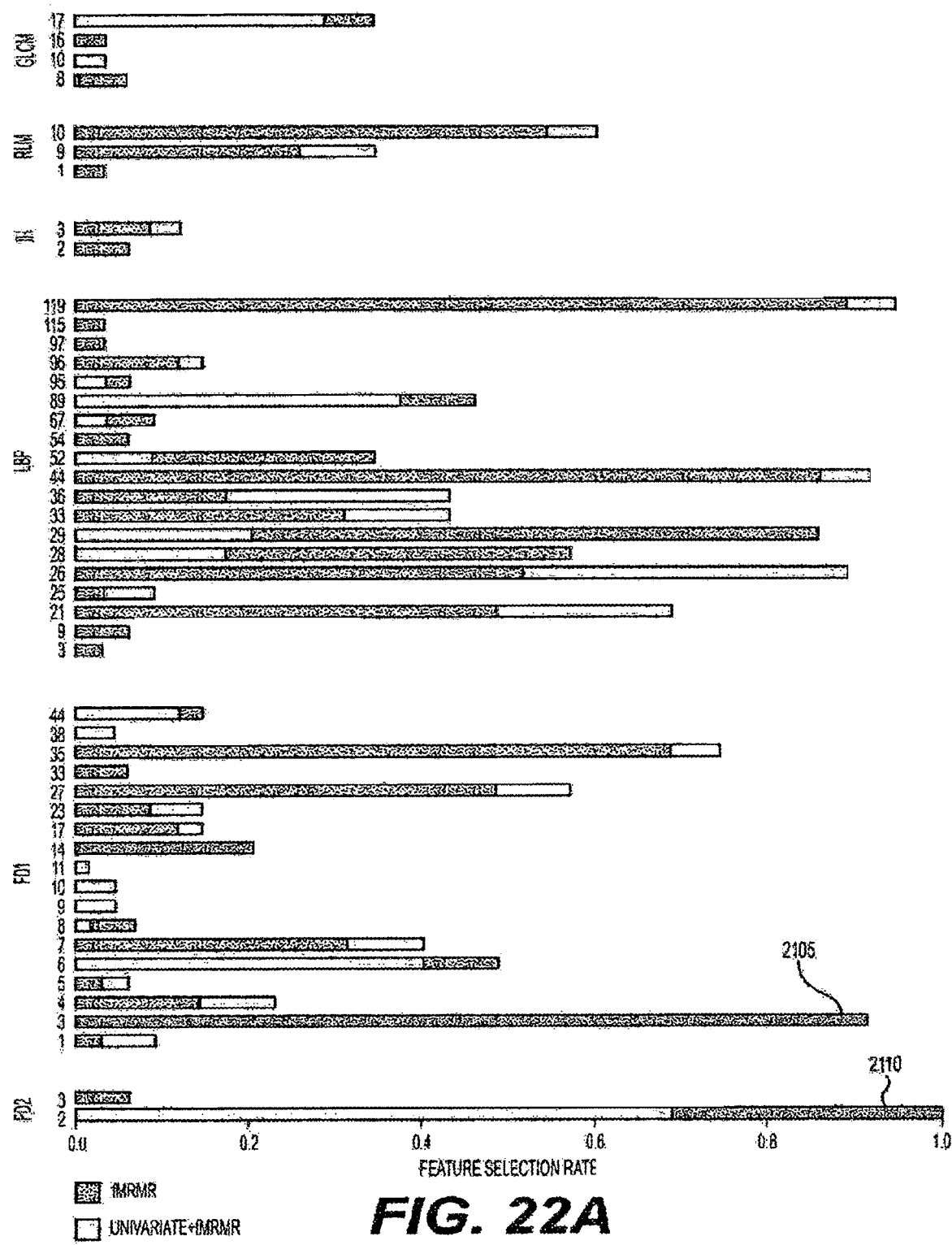
FIG. 22A is an exemplary diagram of the selection rate of individual features when the combined effect of all intensity features are used according to an exemplary embodiment of the present disclosure.
Figure 22B:
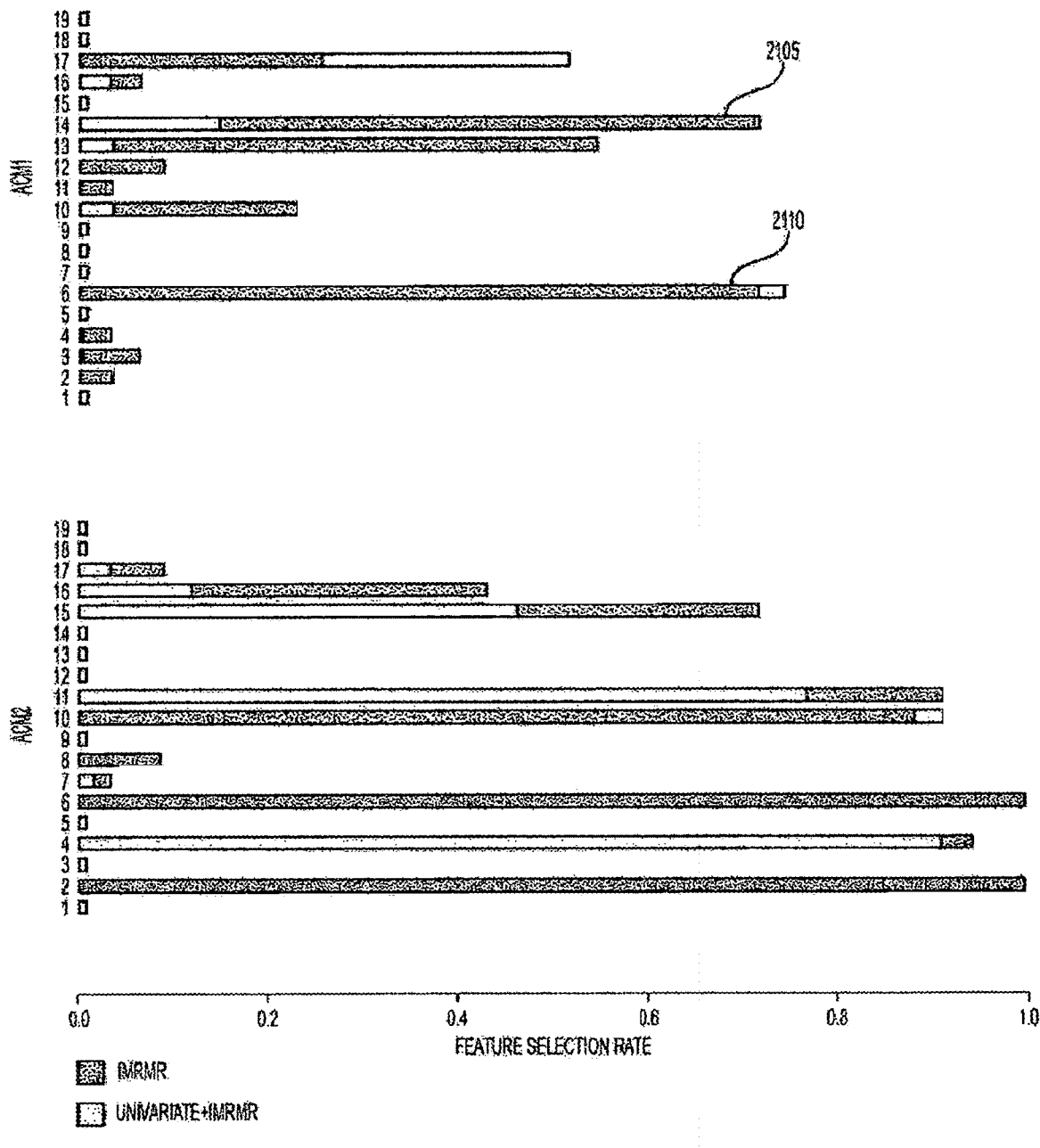
FIG. 22B is an exemplary diagram of the selection rate of individual features when the combined effect of orientation features are evaluated using a leave-one-image-out procedure according to an exemplary embodiment of the present disclosure.
Figure 23:
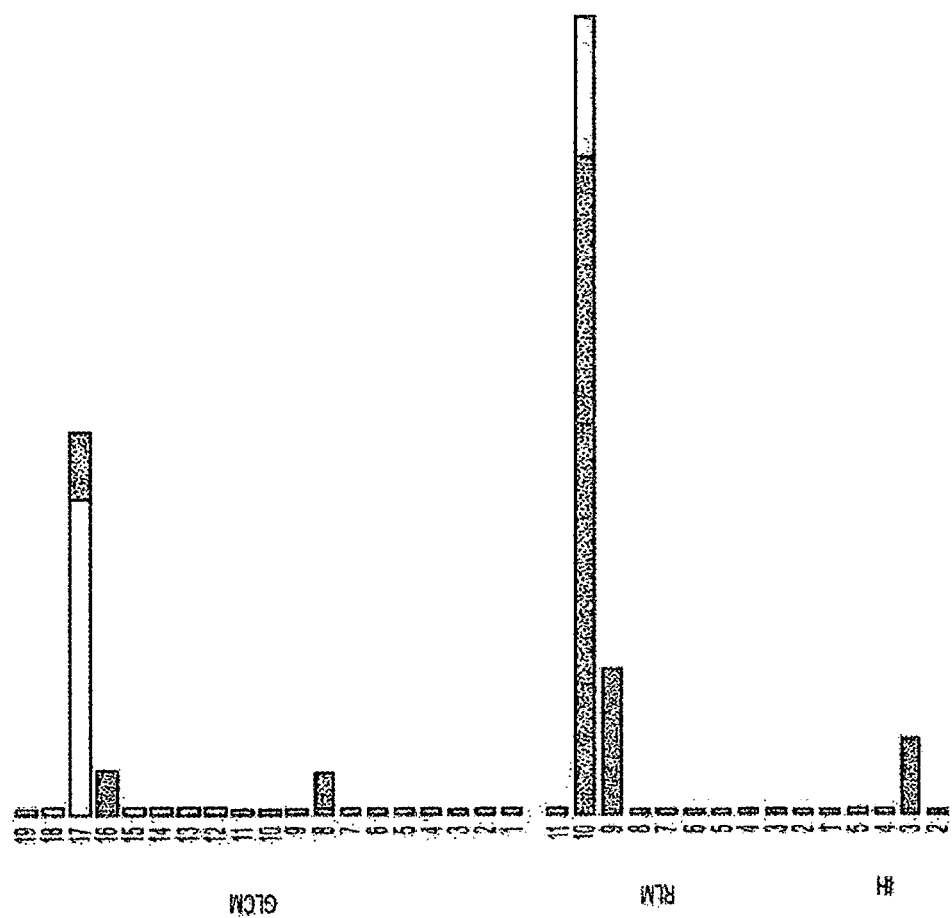
FIG. 23 is an exemplary diagram of the selection rate of individual features when all intensity and orientation features are combined and evaluated using a leave-one-image-out procedure according to an exemplary embodiment of the present disclosure.
Figure 23:
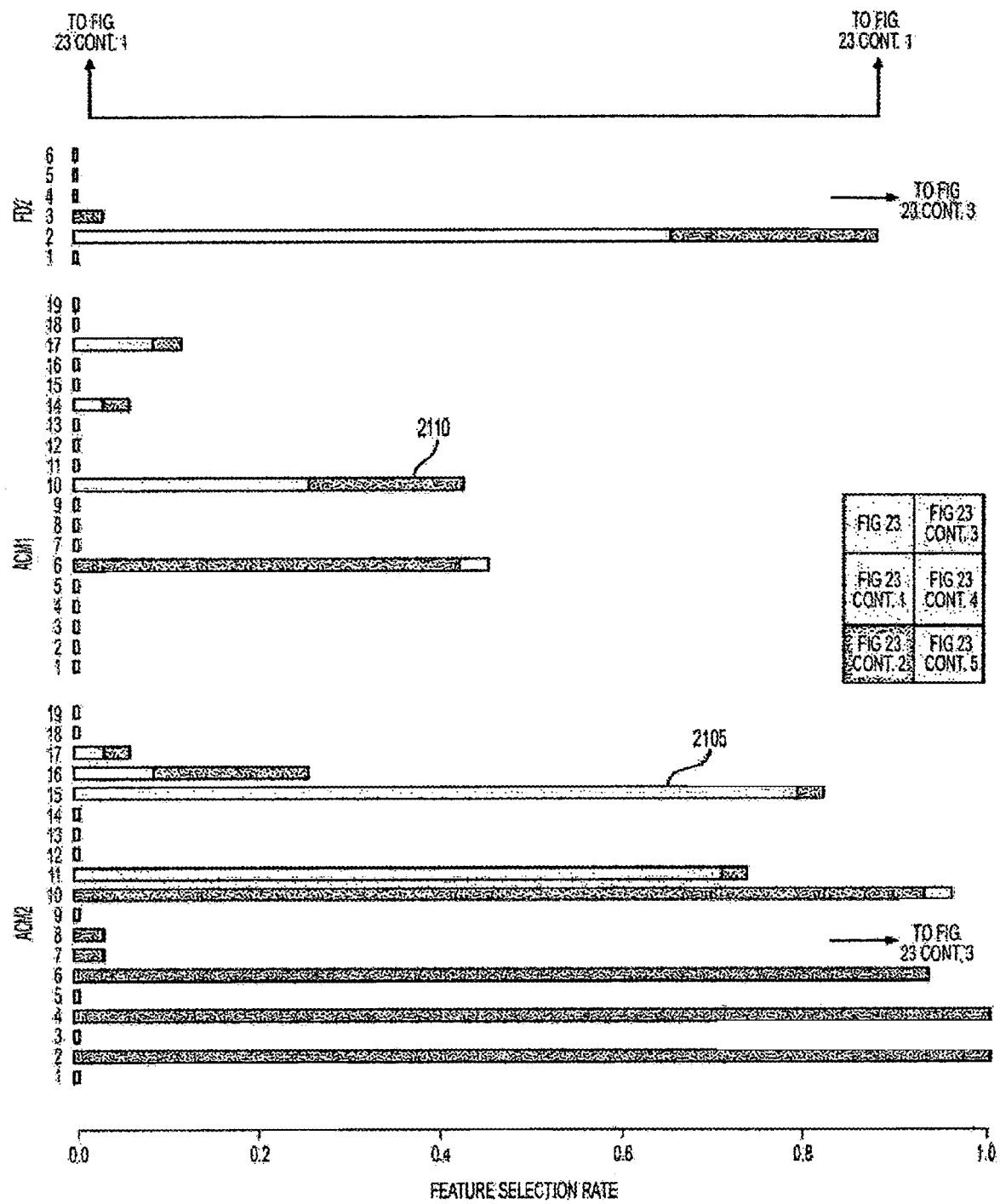
Figure 23:
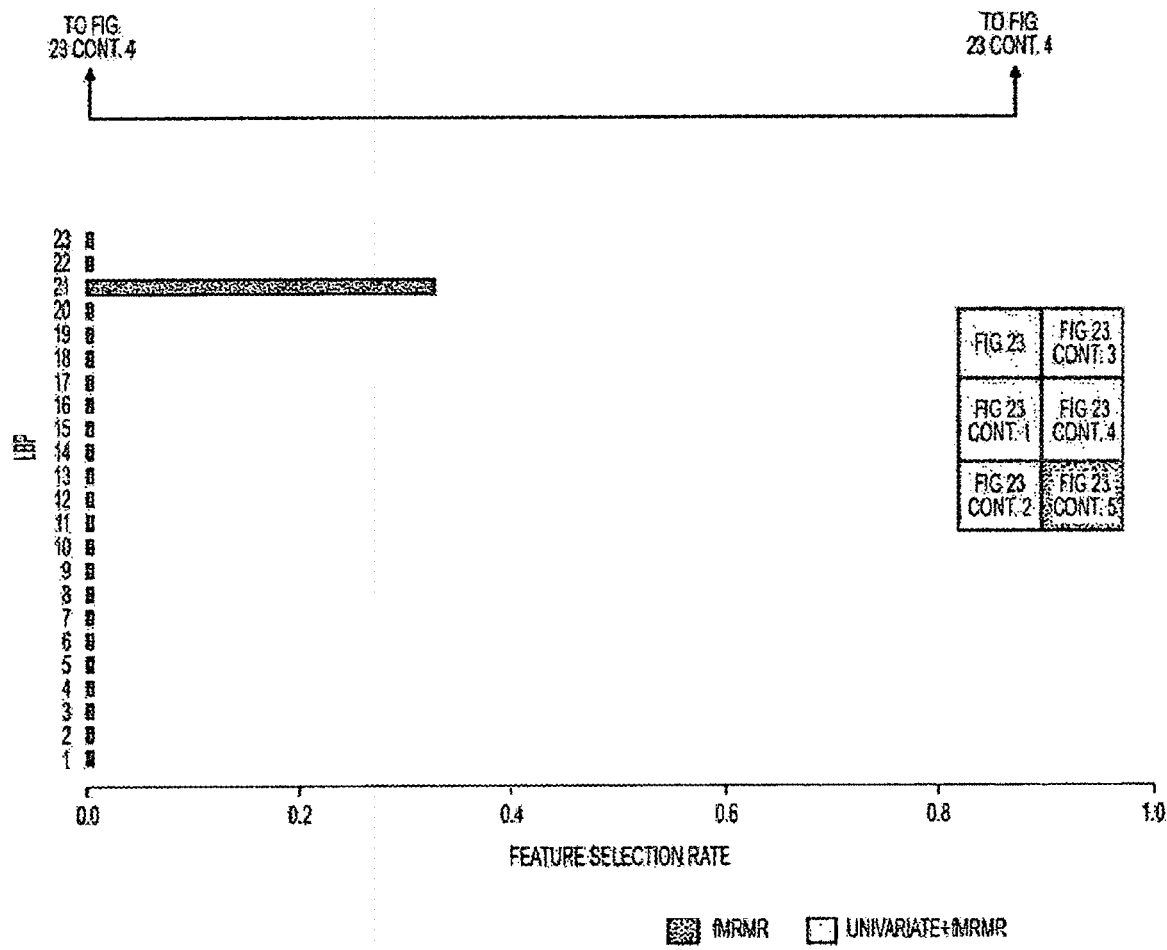
Figure 24:
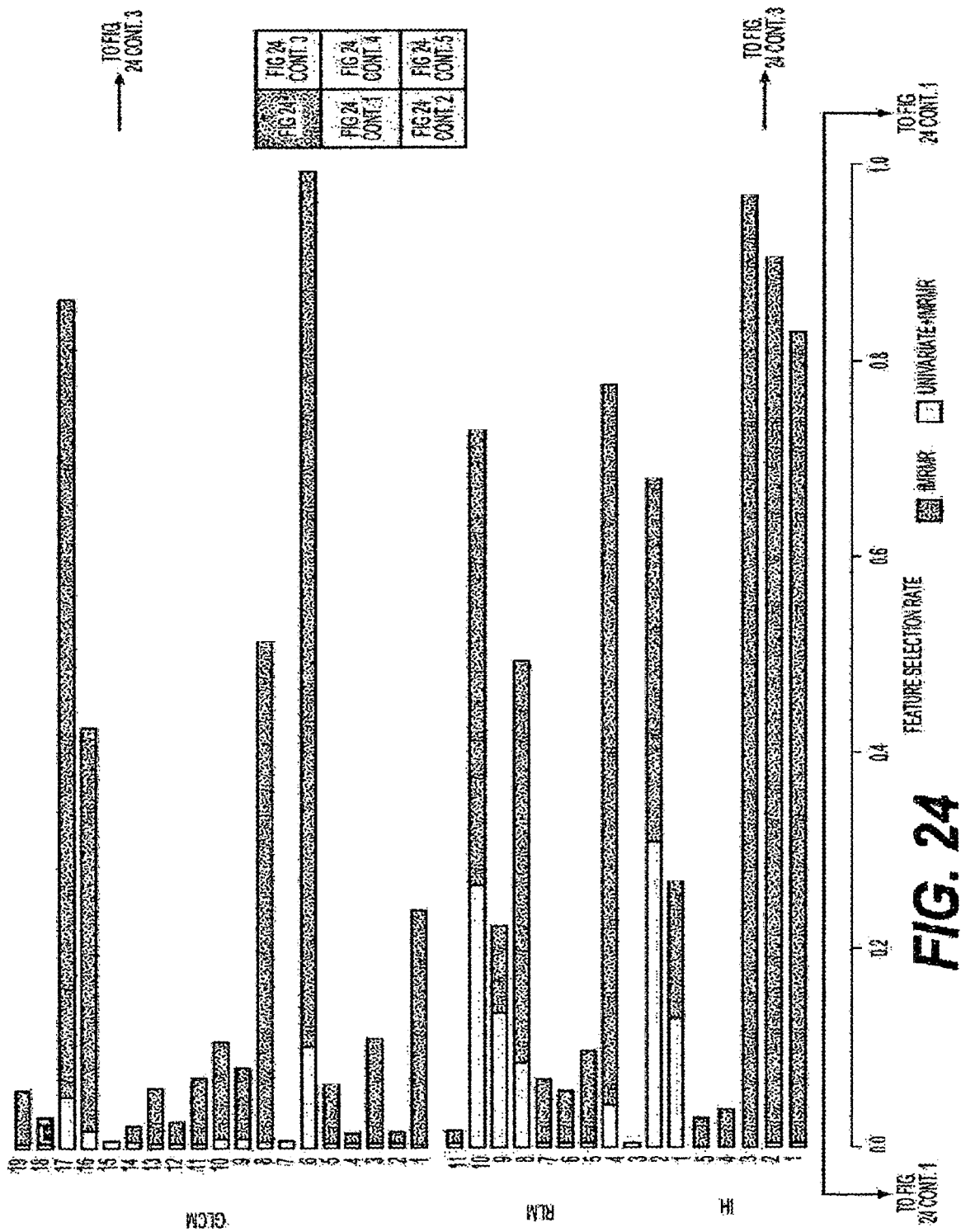
FIG. 24 is an exemplary diagram of the selection rate of features when individual feature sets are evaluated using a ten-fold cross-validation procedure according to an exemplary embodiment of the present disclosure.
Figure 24:
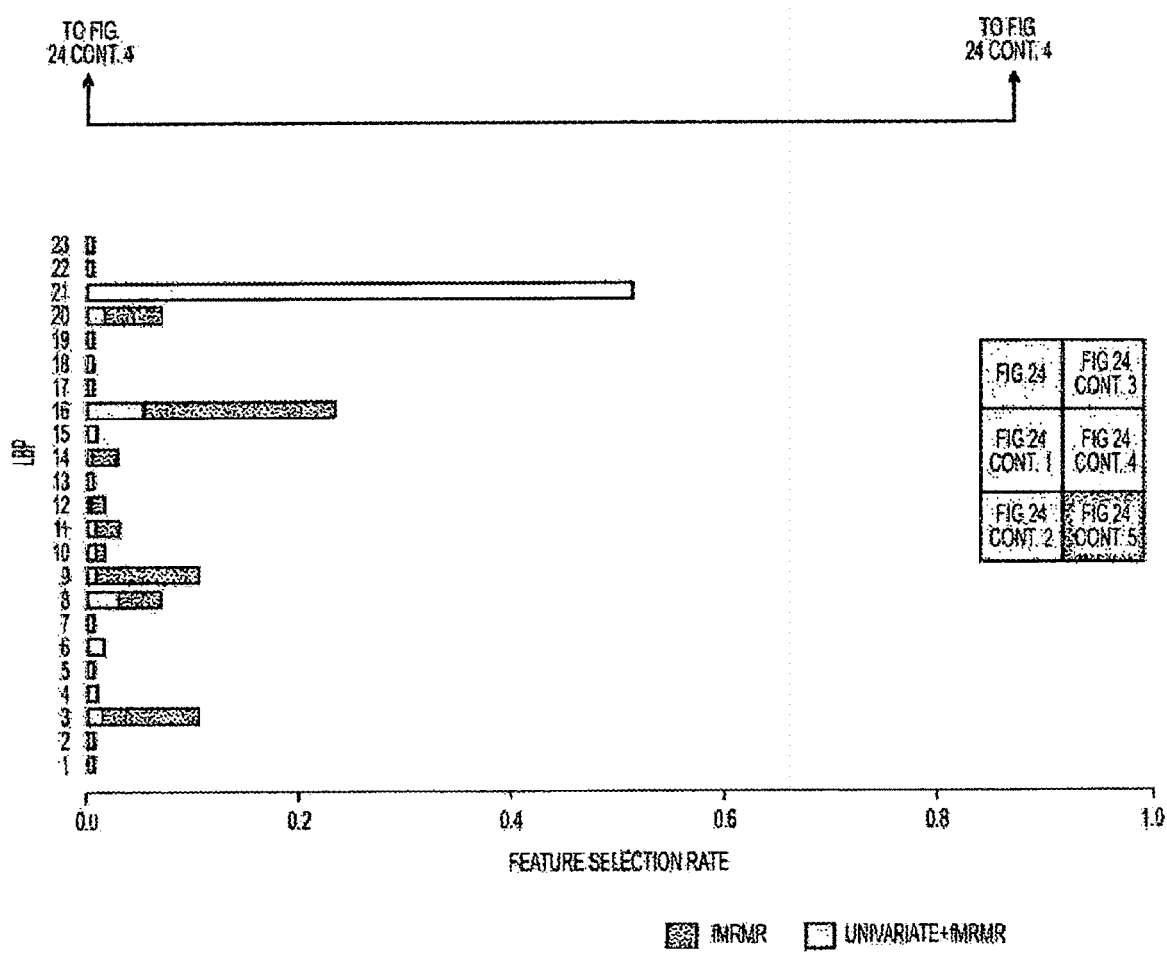
Figure 25A:
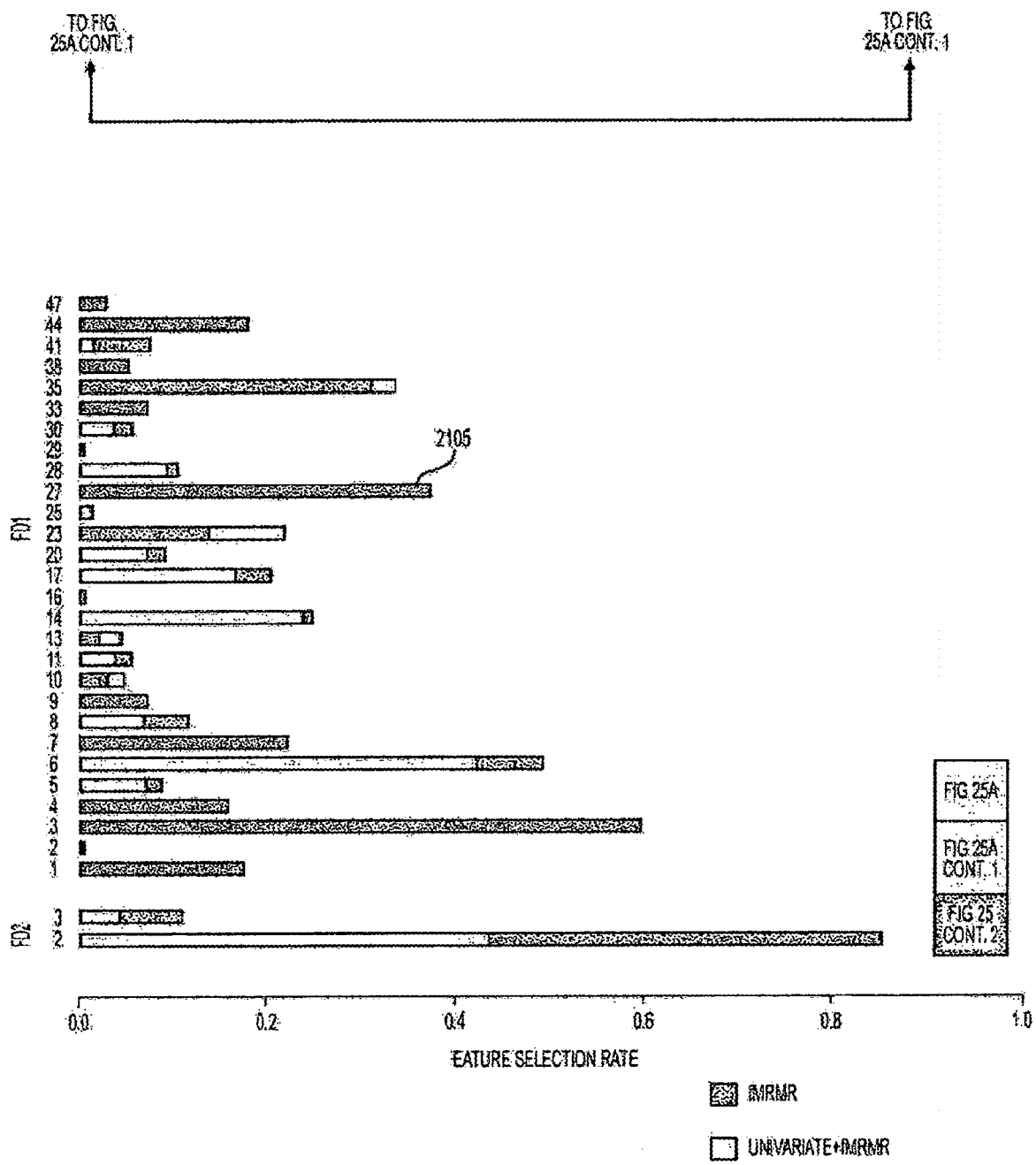
FIG. 25A is an exemplary diagram of the selection rate of individual features when the combined effect of all intensity features are used according to an exemplary embodiment of the present disclosure.
Figure 25B:
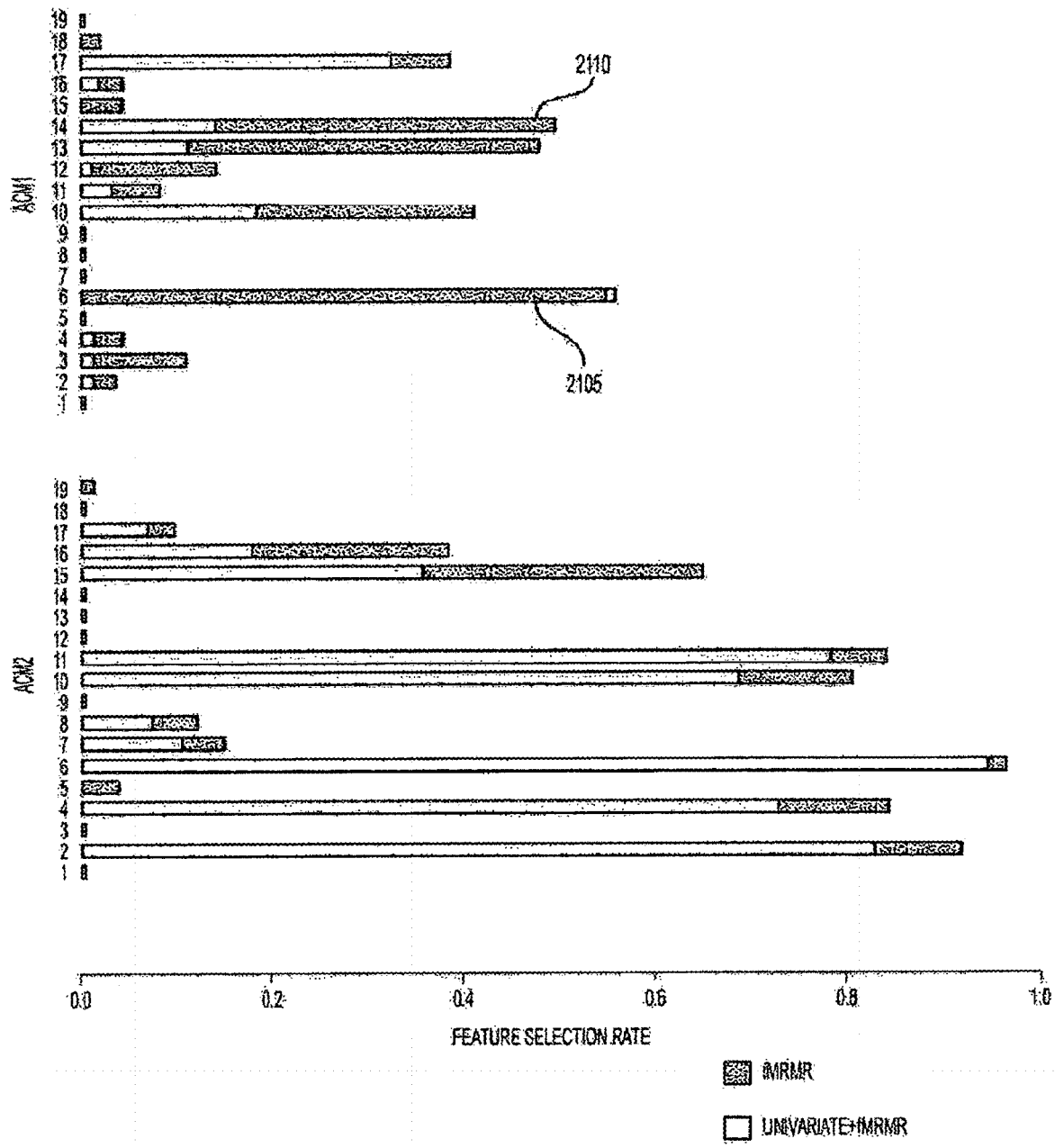
FIG. 25B is an exemplary diagram of the selection rate of individual features when the combined effect of orientation features are evaluated using a ten-fold cross-validation procedure according to an exemplary embodiment of the present disclosure.
Figure 26:
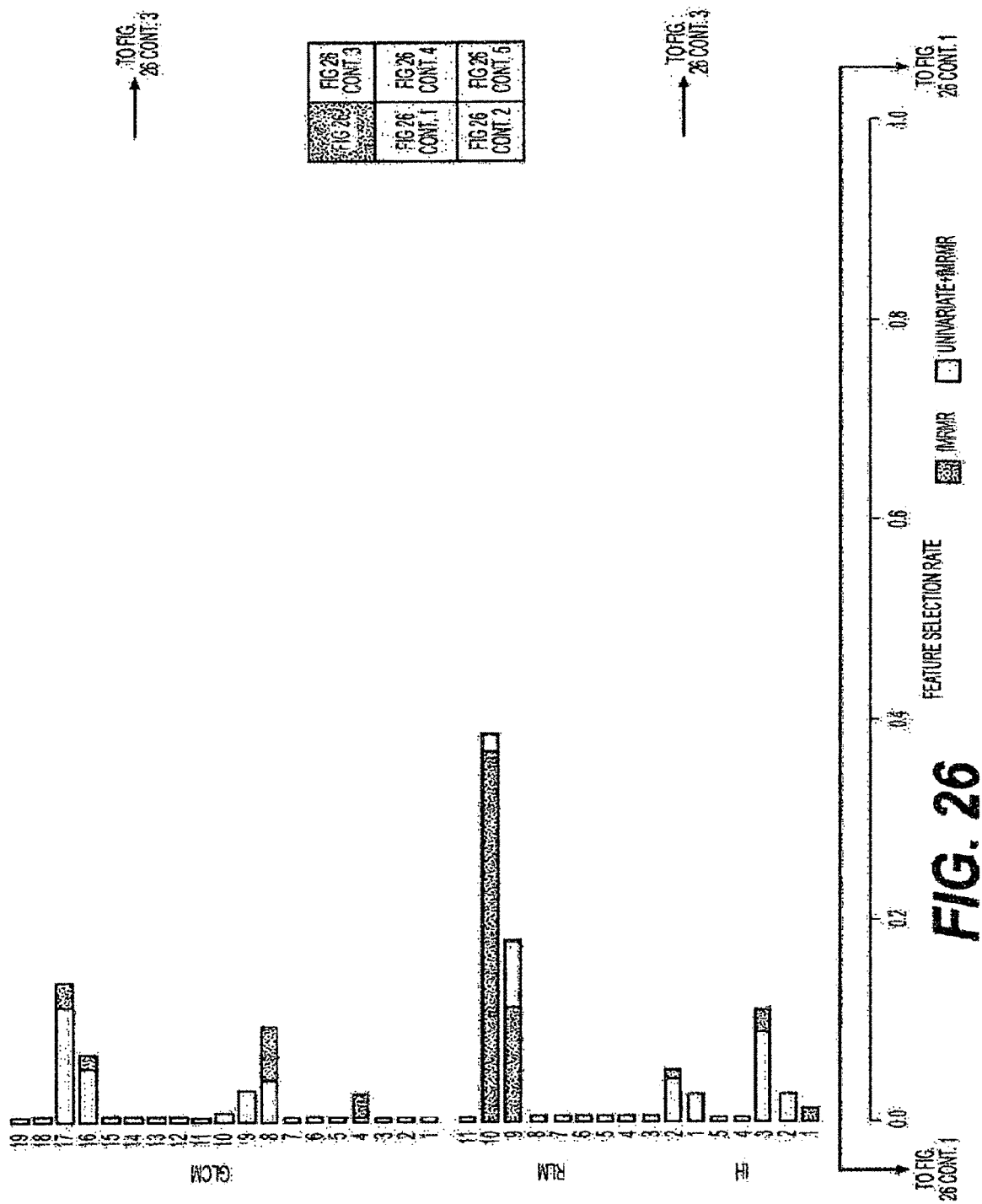
FIG. 26 is an exemplary diagram of the selection rate of individual features when all intensity and orientation features are combined and evaluated using a ten-fold cross-validation procedure according to an exemplary embodiment of the present disclosure.
Figure 26:
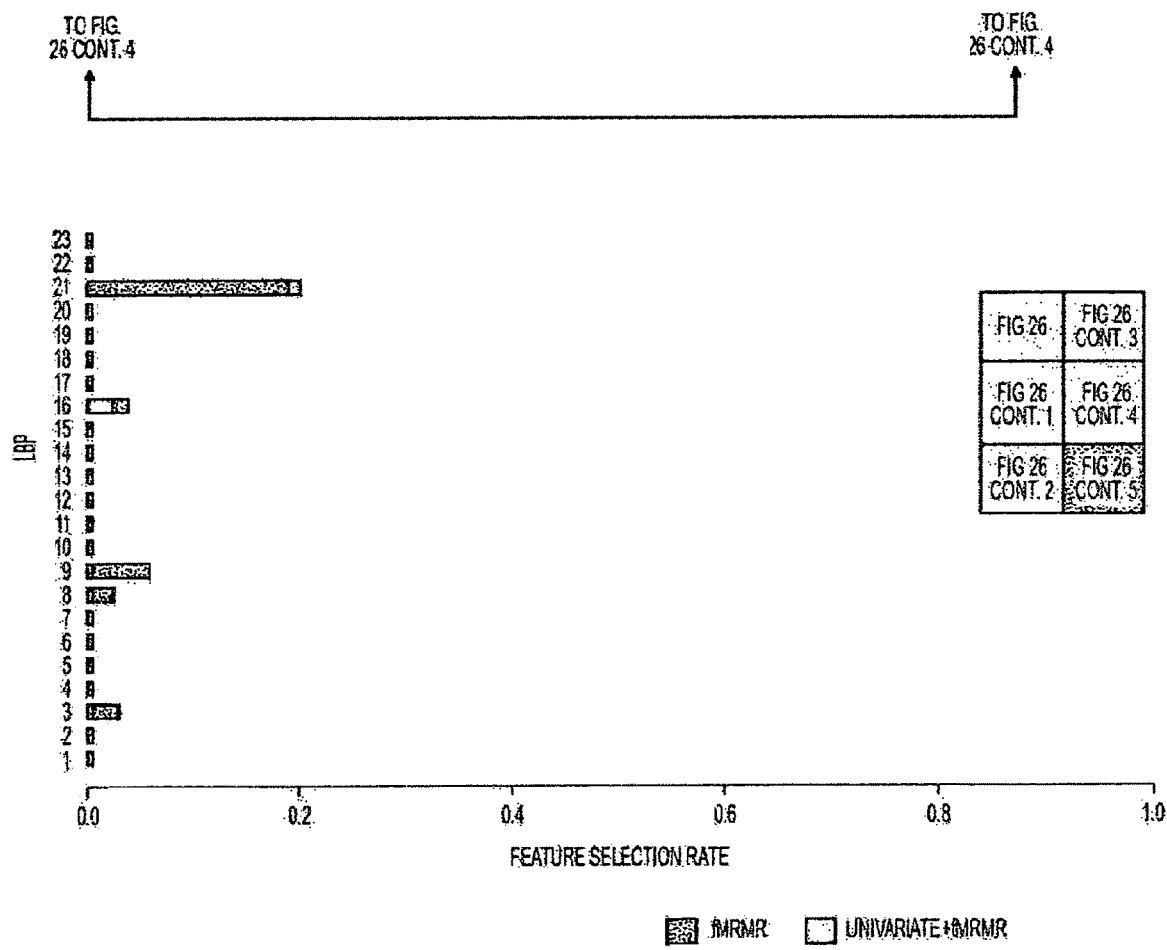

FIGS. 20A and 20B show exemplary histograms according to an exemplary embodiment of the present disclosure. FIGS. 20C and 20D illustrate exemplary images that show the RLM, FIGS. 20E and 20F are images that show the GLCM, FIGS. 20G and 20H illustrate exemplary images that show ACM1, and FIGS. 20I and 20J show exemplary images that show the ACM2, of the tumor regions shown in FIGS. 19A and 19B, respectively.

Exemplary Texture Feature Extraction

To quantify the texture in the tumor region, several well-established first and second order intensity-based features can be extracted using GLCMs, (see, e.g., Reference 136) run-length matrices ("RLM"), (see, e.g., Reference 137) local binary patterns ("LBP"), (see, e.g., References 138 and 139) fractal dimension ("FD"), (see, e.g., Reference 140) intensity histograms ("1H"). The directional edge patterns of the tumor texture were also analyzed using angle-concurrence matrices ("ACM"). (See, e.g., References 141 and 142). A 2D feature extraction technique can be employed, where features can be computed from each slice and averaged over the slices to get a single value for the entire tumor.

For example, GLCM can provide a spatial distribution of pixels present in an image by computing the probability of occurrences of each pixel pair located at a specific distance and a specific angle. To derive rotation invariant features from GLCM, four matrices can be calculated with different angles: 0°, 45°, 90°, and 135° for a specific distance d and can be averaged to form a single matrix (GLCM). Haralick's 14 statistical features, along with three commonly used features: inertia, cluster shade, and cluster prominence (see, e.g., Reference 143) ($G_1$-$G_{17}$), can then be calculated from the resultant matrix. (See, e.g., Reference 136). Renyi and Tsallis entropy ($G_{18}$, $G_{19}$) (see, e.g., Reference 144) was also determined from GLCM, observing the supportive performance of GLCM-based entropy in texture analysis, (see, e.g., Reference 145) which can be defined as, for example:

$$G_{18} = \frac{1}{1-q}\log_2 \sum_{i=1}^{N}\sum_{j=1}^{N}[GLCM(i,j)]^q,$$

$$G_{19} = \frac{1}{1-r}\sum_{i=1}^{N}\sum_{j=1}^{N}[GLCM(i,j)]^r,$$

where q and r can be the order of Renyi and Tsallis entropy, respectively. Based on the discriminatory performance of the features, d=2 pixels (e.g., size of the pixel neighborhood), q=8, r=2, and quantized intensity levels, N=16 can be selected.

Observing the persistent occurrence of long gray-level can run in coarser textures and short gray-level runs in finer textures, RLMs were introduced, which can quantify the coarseness of texture by counting number of consecutive pixels in a specific direction. (See, e.g., Reference 137). Similar to GLCM, RLM can also be calculated in four directions, for example, at 0°, 45°, 90°, and 135°. Eleven features can then be derived from each matrix, and can be averaged to obtain rotation invariant coarseness measures ($R_1$-$R_{11}$).

LBP can characterize the local textural patterns of an image, considering that texture has two components: pattern and strength. (See, e.g., References 138 and 139). The histograms and statistical properties of histograms of two modified LBP, uniform LBP ("ULBP"), and rotation invariant ULBP ("RI-ULBP"), (see, e.g., Reference 139) which can remove less occurring non-uniform patterns and can provide rotation invariant patterns, respectively, can be used. Furthermore, the rotation invariant LBP histogram Fourier features can be extracted by applying discrete Fourier transform on LBP-histogram. (See, e.g., Reference 146). A total of 128 LBP features can be created ($L_1$-$L_{128}$), as listed in Table 13.

Several procedures have been proposed to derive the FD of an image, (see, e.g., References 147 and 148) which can measure its self-similarity. In the exemplary study, a segmentation-based fractal texture analysis ("SFTA") can be employed to explore the segmented textural patterns. (See, e.g., Reference 149). It decomposes the exemplary system, method and computer-accessible medium, according to an exemplary embodiment of the present disclosure, can the image into a set of binary images and computes the FD from borders of segmented regions using box-counting method, which can generate 48 features ($F1_1$-$F1_{48}$). The popular differential box-counting ("DBC") procedure, (see, e.g., Reference 147) with 7×7 neighbors, can also be applied over each pixel of the image to obtain an FD image. The DBC procedure can be chosen due to its superior performance over the Brownian motion procedure. (See, e.g., Reference 147). The maximum and average value of mean, standard deviation and lacunarity extracted from FD images over all the slices were considered as another set of features ($F2_1$-$F2_6$).

To round out the intensity feature set, five elemental first-order statistical features: mean, standard deviation, skewness, kurtosis, and entropy, can be computed based on the intensity-histogram of tumor regions ($I_1$-$I_5$) using the exemplary system, method and computer-accessible medium.

For the characterization of directional edge patterns of tumor, two ACMs (see, e.g., References 141 and 142) can be computed based on joint occurrences of the texture orientation angles using gradient information of tumor, extracted with a sobel operator of size 3×3. The (i, j)$^{th}$ element of $ACM_{l,\theta}$ can represent the probability of the occurrence of the pair of angles (i, j) with a separation of distance l and angle θ. The first ACM (ACM1) can be computed using angle information, whereas the second ACM (ACM2) can be formed considering the gradient angle as well as magnitude, which can be written as $$ACM1_{l,\theta}(i,j) = \frac{S_a(i,j)}{\sum_{i=1}^{N_\theta}\sum_{j=1}^{N_\theta} S_a(i,j)}, ACM2_{(l,\theta)}(i,j) = \frac{S_m(i,j)}{\sum_{i=1}^{N_\theta}\sum_{j=1}^{N_\theta} S_m(i,j)}, \quad (2)$$

where $S_a(i,j)$ and $S_m(i,j)$ can be the number of occurrences and the sum of gradient magnitude responses, respectively, of all pixel-pairs with orientation angle i and j, separated by (l,θ); $N_\theta$ can be the number of quantized angle levels. In the exemplary study, l and $N_\theta$ can be empirically selected as 1 and 8, respectively. The similar features as computed for GLCM can be extracted from both the ACMs, after making them rotation invariant via averaging them over four directions: −0°, 45°, 90°, and 135°. All the derived features are listed in Table 13.

Exemplary Selection of Relevant Features

Feature selection can be employed because all features may not have sufficient discriminatory power, and can include too many features in the prediction model can cause overfitting. Therefore, to avoid overfitting and determine diagnostically relevant features, fMRMR-based feature selection procedure can be used. (See, e.g., References 150-153). With thirty-five patients and 256 features, selection can be a challenging task.

TABLE 13

List of extracted features

| Features Type | Features | Number of Features |
|---|---|---|
| GLCM | Haralick's, inertia, cluster shade and prominence, Renyi and Tsellis entropy | 19 |
| RLM | all run-length features | 11 |
| LBP | histograms of U-LBP and RI-LBP | 59, 10 |
|  | statistical | 21 |
|  | frequency descriptor | 38 |
| FD1 | SFTA feature | 48 |
| FD2 | maximum and average of mean, standard deviation, and lacunarity | 6 |
| IH | mean, standard deviation, kurtosis, skewness, entropy | 5 |
| ACM1 | Haralick's, cluster shade, prominence, inertia, Tselli's and Reny's entropy | 19 |
| ACM2 | Haralick's, cluster shade, prominence, inertia, Tselli's and Reny's entropy | 19 | fMRMR was chosen due to its simplicity and comparable performance with the other procedures (e.g., stepwise logistic regression, fisher score, and wrapper) investigated in the present study. The important features can be selected by the exemplary system, method and computer-accessible medium only using the training set to avoid the effect of bias. An incremental search procedure can be incorporated with fMRMR, where features can be selected in an incremental way (e.g., one by one), iteratively, based on their relevancy as measured by fuzzy mutual information of a feature within the classes and redundancy as measured by averaging fuzzy mutual information of the feature with the already selected features using Equation 3. This iterative process can create a total of D sequential feature sets $S_1, S_2, \ldots, S_D$ such that $S_1 \subset S_2 \subset \ldots \subset S_{D-1} \subset S_D$, if D can be the dimension of features, containing features with descending order of importance. The optimum feature set can be selected based on the minimum classification error obtained with a leave-one-image out and Naive-Bayes classifier applied on the training set. The incremental fMRMR method, used in the exemplary study, is described in Procedure 1 below.

Along with this fMRMR feature selection procedure, a two stage procedure where univariate analysis followed by fMRMR can be introduced for feature selection to observe the effect of feature's dimensionality on the fMRMR procedure. The exemplary system, method and computer-accessible medium, according to an exemplary embodiment of the present disclosure, can incorporate, an entry criteria based on the statistical significance of each feature, where features with p-value of the likelihood ratio test 0.1 may only be analyzed further to determine their importance using the fMRMR procedure. It can reduce the number of features to be analyzed with fMRMR than the earlier method.

Exemplary Results

The performance of texture features, for 2-years survival prediction of PDAC patients, was investigated using an ROC curve, area under ROC curve ("AUC"), and classification accuracy ("AC") with its corresponding sensitivity (e.g., $S_n$) and specificity (e.g., $S_p$). The ten-fold cross-validation procedure can be repeated 20 times and the results can be averaged over all the iterations.

An exemplary analysis indicates that individual features can predict survival; however, combinations of features obtained using the exemplary system, method and computer-accessible medium, provide better discriminatory

---

Exemplary Procedure 1
fMRMR feature selection

---

Input: Set of training data with D-dimensional feature vectors $F = \{f_1, f_2, \ldots, f_D\}$.
Output: optimum features set $F = \{f_1^r, f_2^r, \ldots, f_O^r\} \in F$
begin
1. For m = 1 to D
   i  With the incremental fMRMR procedure select feature using the following condition:

$$J(f_j) \overset{max}{_{f_j \in F - F_{m-1}^r}} \left[ MI(f_j; c) - \frac{1}{m-1} \sum_{f_i \in F_{m-1}^r} MI(f_j, f_i) \right], \quad (3)$$

where MI represents fuzzy mutual information between two variables, $c = [0, 1]$ represents the class vector, and $F_{m-1}^r$ can be the set of already selected features.
   ii  This creates a set of features, $F_m^r = \{f_1^r, f_2^r, \ldots, f_m^r\} \subset F$ and $\supset F_{m-1}^r$, ranked according to their importance.
2. Determine optimal size (O) of candidate feature set $F_o^r$ with leave-one-image-out technique that provide minimum classification error i.e.,
    $F = F_o^r = \{f_1^r, f_2^r, \ldots, f_o^r\}$, where $O = \arg_{k \in [1, D]}^{min}\{e_k\}$,
where $e_k$ = classification error with feature set $S_k$.

---

Exemplary Classification and Cross-Validation

To evaluate the predictive value of relevant features at 2 year survival, a simple yet effective NaiveBayes classifier (see, e.g., Reference 154) can be introduced, where the conditional probability of features for a given class can be assumed to follow a Gaussian distribution. Due to the small size of the dataset, splitting of data into two, groups-training and testing was not feasible. In this situation, cross validation can be an effective way of analyzing the performance of the exemplary system, method and computer-accessible medium. (See, e.g., Reference 155). Leave-one image-out and ten-fold cross-validation were used. The leave-one-image-out procedure can be the extreme form of cross-validation, where one sample can be used for testing and the remaining observations can be used to train the model. This can be repeated until all the images can be explored as test data. On the other hand, in ten-fold cross-validation, the observations can be randomly divided into ten groups; one can be retained as the test set and others can be used for training. The ten-fold cross-validation can then be repeated ten times, with each of the groups used exactly once as the test set.

power. Tables 15 and 16 below show the exemplary results acquired with different sets of selected features and Naive-Bayes based classifier using leave-one-image-out and ten-fold cross-validation, respectively using the exemplary system, method and computer-accessible medium. The exemplary fMRMR method, with and without univariate analysis, demonstrates comparable performance, except for small feature sets where fMRMR is marginally better. Among all the intensity- and orientation-based predictors, ACM2 provides the best performance with an AUC of about 0.90 and about 0.86 and Ac of about 82.86% and about 78.29% using fMRMR with leave-one-image-out and ten-fold cross-validation, respectively. The selection rate of individual features (e.g., feature selection rate, FSR) corresponding to Tables 15 and 16 are shown in FIGS. 21-23 and FIGS. 24-26, respectively (which show univariate+fMRMR 2105 and fMRMR 2110). The frequently selected features with FSR>0.5 are also listed in Table 14 below. Many of the selected features were common in both validation procedures, irrespective of the selection procedure.

TABLE 14

| | | List of frequently selected features (FSR > 0.50) | |
|---|---|---|---|
| Feature Set | Feature Selection | Selected Features | |
| | | Leave-one-image-out | Ten-fold cross-validation |
| GLCM | FMRMR | $G_6, G_8, G_{16}, G_{17}$ | $G_6, G_8, G_{17}$ |
| | univariate + FMRMR | $G_6, G_{17}$ | $G_6, G_{17}$ |

TABLE 14-continued

List of frequently selected features (FSR > 0.50)

| Feature Set | Feature Selection | Selected Features Leave-one-image-out | Ten-fold cross-validation |
|---|---|---|---|
| RLM | FMRMR | $R_4$, $R_8$, $R_{10}$ | $R_2$, $R_4$, $R_{10}$ |
|  | univariate + FMRMR | $R_1$, $R_9$ | *** |
| LBP | FMRMR | $L_{26}$, $L_{28}$, $L_{29}$, $L_{33}$, $L_{44}$, $L_{52}$, $L_{119}$ | $L_{26}$, $L_{28}$, $L_{29}$, $L_{33}$, $L_{44}$, $L_{52}$, $L_{119}$ |
|  | univariate + FMRMR | $L_{21}$, $L_{26}$, $L_{32}$, $L_{33}$, $L_{36}$, $L_{44}$, $L_{119}$ | $L_{26}$, $L_{33}$, $L_{36}$, $L_{44}$, $L_{119}$ |
| F1 | FMRMR | $F1_3$, $F1_4$, $F1_6$, $F1_7$, $F1_{17}$, $F1_{23}$, $F1_{27}$, $F1_{35}$ | $F1_3$, $F1_6$, $F1_{23}$, $F1_{27}$, $F1_{35}$ |
|  | univariate + FMRMR | $F1_1$, $F1_3$, $F1_4$, $F1_5$, $F1_6$, $F1_7$, $F1_{14}$, $F1_{17}$, $F1_{23}$, $F1_{27}$, $F1_{35}$ | $F1_1$, $F1_3$, $F1_4$, $F1_6$, $F1_7$, $F1_{14}$, $F1_{23}$, $F1_{27}$, $F1_{35}$ |
| F2 | FMRMR | $F2_2$, $F2_4$, $F2_6$ | $F2_1$, $F2_2$, |
|  | univariate + FMRMR | *** | *** |
| IH | FMRMR | $I_1$, $I_2$, $I_3$ | $I_1$, $I_2$, $I_3$ |
|  | univariate + FMRMR | $I_1$, $I_3$ | *** |
| ACM1 | FMRMR | $A_6$, $A_{10}$ | $A_6$, $A_{10}$ |
|  | univariate + FMRMR | $A_6$, $A_{10}$ | $A_6$, $A_{10}$ |
| ACM2 | FMRMR | $M_2$, $M_4$, $M_6$, $M_{10}$, $M_{11}$, $M_{16}$ | $M_2$, $M_4$, $M_6$, $M_{10}$, $M_{11}$, $M_{16}$ |
|  | univariate + FMRMR | $M_2$, $M_4$, $M_6$, $M_{10}$ | $M_2$, $M_4$, $M_6$, $M_{10}$, $M_{11}$ |
| All intensity | FMRMR | $R_{10}$, $L_{26}$, $L_{28}$, $L_{29}$, $L_{44}$, $L_{119}$, $F1_3$, $F1_{35}$, $F2_2$ | $L_{29}$, $L_{44}$, $L_{119}$, $F1_3$, $F1_6$, $F2_2$ |
|  | univariate + FMRMR | $R_{10}$, $L_{21}$, $L_{26}$, $L_{44}$, $L_{119}$, $F1_3$, $F1_{27}$, $F1_{35}$, $F2_2$ | $L_{26}$, $L_{33}$, $L_{36}$, $L_{44}$, $L_{119}$, $F1_3$ |
| All orient | FMRMR | $A_6$, $A_{13}$, $A_{14}$, $M_2$, $M_4$, $M_6$, $M_{10}$, $M_{11}$, $M_{15}$ | $A_6$, $M_2$, $M_4$, $M_6$, $M_{10}$, $M_{11}$, $M_{15}$ |
|  | univariate + FMRMR | $A_6$, $A_{17}$, $M_2$, $M_4$, $M_6$, $M_{10}$, $M_{11}$ | $A_6$, $M_2$, $M_4$, $M_6$, $M_{10}$, $M_{11}$ |
| All | FMRMR | $R_{10}$, $L_{44}$, $L_{119}$, $F1_3$, $F1_6$, $F1_{27}$, $F1_{35}$, $F2_2$, $M_2$, $M_4$, $M_6$, $M_{10}$, $M_{11}$, $M_{15}$ | $L_{119}$, $F1_3$, $M_2$, $M_4$, $M_6$, $M_{10}$, $M_{11}$, $M_{15}$ |
|  | univariate + FMRMR | $R_{10}$, $L_{44}$, $L_{119}$, $F1_3$, $F1_6$, $F1_{27}$, $F1_{35}$, $F2_2$, $M_2$, $M_4$, $M_6$, $M_{10}$, $M_{11}$, $M_{15}$ | $L_{119}$, $F1_3$, $M_2$, $M_4$, $M_6$, $M_{10}$, $M_{11}$, $M_{15}$ |

TABLE 15

The area under ROC, classification accuracy (in percentage), sensitivity and specificity obtained with the proposed method using leave-one-image-out technique.

| Feature Set | Univariate + fMRMR Feature Selection | | | | fMRMR Feature Selection | | | |
|---|---|---|---|---|---|---|---|---|
|  | AUC | Ac | Sn | Sp | AUC | Ac | Sn | Sp |
| GLCM | 0.58 | 62.86 | 0.47 | 0.75 | 0.66 | 62.86 | 0.47 | 0.75 |
| RLM | 0.58 | 65.71 | 0.40 | 0.85 | 0.68 | 68.57 | 0.47 | 0.85 |
| LBP | 0.52 | 45.71 | 0.40 | 0.50 | 0.50 | 54.29 | 0.33 | 0.70 |
| FD1 | 0.71 | 71.43 | 0.60 | 0.80 | 0.72 | 74.29 | 0.67 | 0.80 |
| FD2 | *** | *** | *** | *** | 0.54 | 54.29 | 0.33 | 0.70 |
| IH | 0.65 | 65.71 | 0.47 | 0.80 | 0.69 | 68.57 | 0.47 | 0.85 |
| ACM1 | 0.77 | 71.43 | 0.60 | 0.80 | 0.77 | 68.57 | 0.60 | 0.75 |
| ACM2 | 0.88 | 80.0 | 0.67 | 0.90 | 0.90 | 82.86 | 0.67 | 0.95 |
| All Intensity | 0.60 | 71.4 | 0.60 | 0.80 | 0.62 | 71.4 | 0.60 | 0.85 |
| All Orient | 0.88 | 80.0 | 0.73 | 0.85 | 0.81 | 77.14 | 0.67 | 0.85 |
| All | 0.84 | 68.57 | 0.53 | 0.80 | 0.83 | 74.29 | 0.60 | 0.85 |

The maximum AUC and $A_c$ were highlighted with bold face.

"***" corresponds no outcome due to the selection of zero features with the feature selection procedure.

TABLE 16

The area under ROC, classification accuracy (in percentage), sensitivity and specificity obtained with the proposed method using ten-fold cross-validation technique.

| Feature Set | Univariate + fMRMR Feature selection | | | | fMRMR Feature selection | | | |
|---|---|---|---|---|---|---|---|---|
| | AUC | Ac | Sn | Sp | AUC | Ac | Sn | Sp |
| GLCM | 0.60 ± 0.05 | 60.0 ± 3.3 | 0.47 ± 0.06 | 0.70 ± 0.05 | 0.62 ± 0.03 | 63.29 ± 4.28 | 0.45 ± 0.06 | 0.77 ± 0.05 |
| RLM | 0.62 ± 1.65 | 65.71 ± 0.02 | 0.43 ± 0.05 | 0.85 ± 0.03 | 0.62 ± 0.06 | 64.57 ± 3.87 | 0.41 ± 0.07 | 0.82 ± 0.04 |
| LBP | 0.56 ± 0.08 | 55.43 ± 6.58 | 0.49 ± 0.09 | 0.60 ± 0.08 | 0.53 ± 0.07 | 52.86 ± 6.11 | 0.42 ± 0.08 | 0.61 ± 0.10 |
| FD1 | 0.71 ± 0.03 | 72.29 ± 2.09 | 0.61 ± 0.05 | 0.81 ± 0.02 | 0.69 ± 0.03 | 71.14 ± 3.33 | 0.58 ± 0.06 | 0.81 ± 0.03 |
| FD2 | *** | *** | *** | *** | 0.55 ± 0.07 | 58.14 ± 6.95 | 0.49 ± 0.10 | 0.65 ± 0.11 |
| IH | *** | *** | *** | *** | 0.66 ± 0.04 | 67.57 ± 3.85 | 0.46 ± 0.08 | 0.84 ± 0.02 |
| ACM1 | 0.77 ± 0.04 | 71.57 ± 4.86 | 0.62 ± 0.07 | 0.79 ± 0.07 | 0.74 ± 0.06 | 68.86 ± 6.35 | 0.56 ± 0.11 | 0.79 ± 0.07 |
| ACM2 | 0.84 ± 0.04 | 77.0 ± 0.05 | 0.65 ± 0.05 | 0.86 ± 0.05 | 0.86 ± 0.04 | 78.29 ± 3.98 | 0.66 ± 0.06 | 0.88 ± 0.08 |
| All Intensity | 0.57 ± 0.06 | 59.0 ± 4.93 | 0.48 ± 0.09 | 0.68 ± 0.07 | 0.57 ± 0.06 | 60.29 ± 5.15 | 0.46 ± 0.09 | 0.71 ± 0.06 |
| All Orient | 0.84 ± 0.03 | 77.29 ± 3.98 | 0.66 ± 0.06 | 0.86 ± 0.05 | 0.85 ± 0.03 | 78.0 ± 2.95 | 0.67 ± 0.04 | 0.87 ± 0.03 |
| All | 0.76 ± 0.06 | 71.43 ± 6.55 | 0.61 ± 0.12 | 0.79 ± 0.05 | 0.77 ± 0.06 | 71.14 ± 6.28 | 0.59 ± 0.13 | 0.80 ± 0.06 |

The maximum AUC and $A_c$ were highlighted with bold face.
'***' corresponds no outcome due to the selection of zero features with the feature selection technique.

Figure 27B:
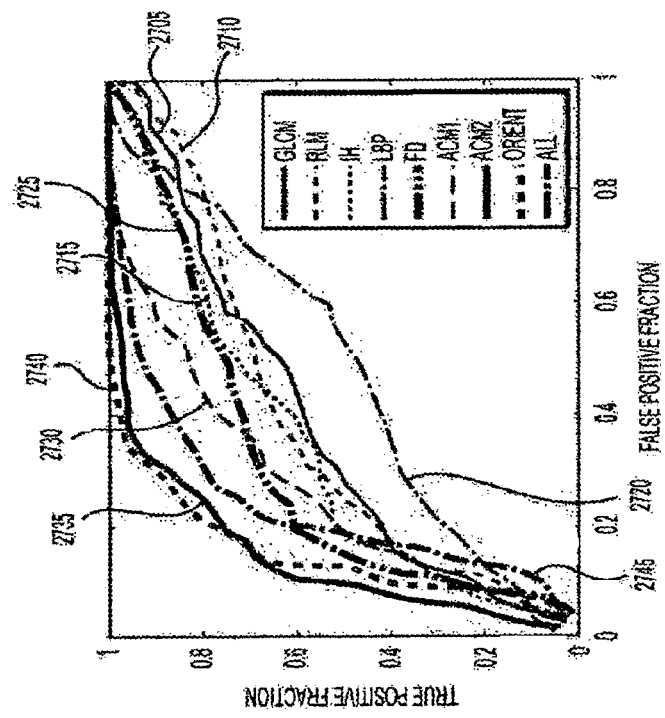
FIG. 27B is an exemplary graph showing a ROC curve obtained with different feature sets, extracted from tumor region using a ten-fold cross-validation procedure according to an exemplary embodiment of the present disclosure.
Figure 27A:
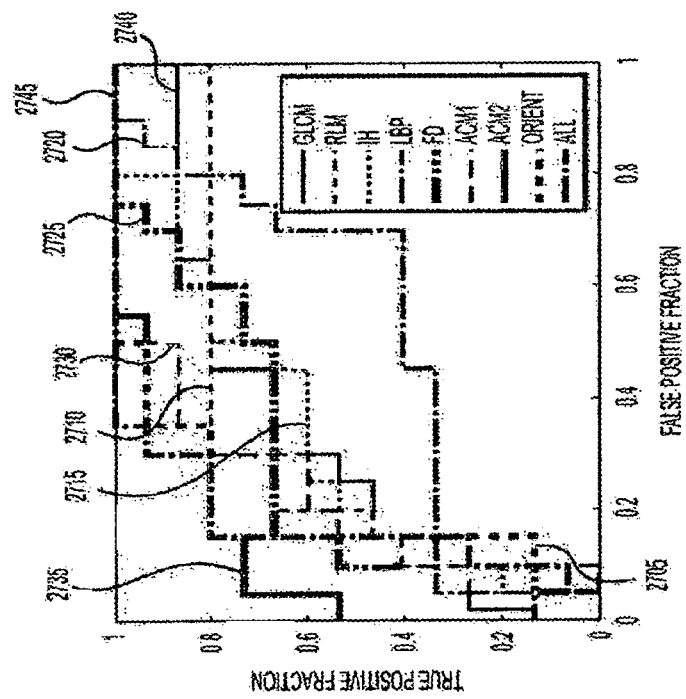
FIG. 27A is an exemplary graph showing a ROC curve obtained with different feature sets, extracted from a tumor region, using a leave-one-image-out procedure according to an exemplary embodiment of the present disclosure.

The fMRMR procedure, with and without univariate analysis, shows comparable performance along with a few commonly selected features. However, no FD2 features were selected when fMRMR was combined with univariate analysis, for both validation procedures, since the features obtain p>0.1. Similar phenomenon can be observed for IH features ten-fold cross-validation. Among all the intensity, and orientation-based predictors, ACM2 can provide the best performance with AUC of about 0.90 and about 0.86 and Ac of about 82.86% and about 78.29% using the fMRMR procedure with leave-one-image-out and ten-fold cross-validation, respectively (e.g., see, Tables 15 and 16). No improvement can be observed while all types of intensity and edge descriptors can be combined. ROC curves, obtained for different feature sets selected with fMRMR, are shown in the graphs of FIGS. 27A and 27B (e.g., GLCM 2705, RIM 2710, IH 2715, LBP 2720, FD 2725, ACM1 2730, ACM2 2735, Orient 2740 and for all 2745).

Exemplary Discussion

Although the performance of fMRMR and univariate fMRMR were comparable, the exemplary results indicate superiority of fMRMR alone for smaller feature sets, and vice-versa, when analyzed with leave-one-image-out. However, for ten-fold cross-validation, fMRMR alone obtained slightly better results. This observation is likely due to the smaller training data in the ten-fold cross-validation; thus, fewer features can be significant on univariate analysis when compared to the leave-one-image-out method. For example, no single III feature was selected in several iterations of cross-validation, whereas in leave-one-image-out significant performance was observed with the same feature set (e.g., See, Tables 15 and 16). The consistency of features is confirmed via the selection of several common features irrespective of the feature selection and validation procedures.

For example, ACM-based features achieved the best performance among all features, and were selected most often. These features can represent directional change in intensity (e.g., directional edge patterns) of an image. Radiographically, differences in ACM2 can reflect areas of necrosis within the tumor with decreased enhancement on CT. These would have developed before the administration of neoadjuvant therapy due to underlying histologic or genetic alterations. Within all the statistical features, extracted from the orientation image, contrast (e.g., $M_2$), variance (e.g., $M_4$), sum average (e.g., $M_6$), difference variance (e.g., $M_{10}$), difference entropy (e.g., $M_{11}$), inertia (e.g., $M_{15}$ of orientation patterns were mostly preferred (FSR>0.5), whereas energy, correlation coefficient, inverse difference, Shannon entropy, Information-theoretic measures of correlation, Maximal Correlation Coefficient, Renyi entropy, Tsallis entropy were never selected. Intensity features were not so effective, in comparison to the edge-based features; fractal dimension achieved best AUC of 0.72 and Ac of about 74.29% among all the intensity descriptors. The combination of different intensity and edge features did not improve performance (e.g., Tables 15 and 16), due to the overfitting problem of high-dimensional data. It should also be noted that the specificity obtained by the methods were higher than the sensitivity, which can imply better predictability of features for patients alive greater than 2-years than died before 2-years.

The exemplary system, method and computer-accessible medium, according to an exemplary embodiment of the present disclosure, can utilize texture information extracted from pre-treatment CT images obtained under controlled clinical trial conditions in order to predict the survival rate of PDAC patients. This can have significant clinical implications because it is believed that there are no known pre-treatment prediction tools for PDAC. A prediction prior to treatment can facilitate optimal selection of patients for surgery or neoadjuvant chemotherapy, and can provide further insight into this disease. CT is the standard imaging modality used in the clinical staging of PDAC. (See, e.g., Reference 156). Thus, the exemplary system, method and computer-accessible medium, according to an exemplary embodiment of the present disclosure, can provide non-invasive disease characteristics in any medical center.

Exemplary Quantitative Measures of Tumor Heterogeneity Predict Response to Chemotherapy from Pre-Treatment CT in Patients with Colorectal Liver Metastases Exemplary Methods Patients and relevant imaging were pooled from two previous prospective trials evaluating hepatic artery infusion plus systemic chemotherapy for unresectable colorectal liver metastases at Memorial Sloan Kettering Cancer Center. (See, e.g., References 157 and 158). For inclusion in these trials, patients must have histologically confirmed colorectal adenocarcinoma. In both previously published trials, patients received hepatic artery infusion of floxuridine/ dexamethasone ("HAI FUDR") in combination with systemic chemotherapy. According to an exemplary protocol, patients received pre-treatment CT images of the chest, abdomen and pelvis. This baseline CT scan was used for quantitative image analysis, and to determine the tumor volume and the largest tumor diameter of the index lesion. Following administration of HAI FUDR, and systemic chemotherapy, the first response assessment occurred between 8 and 10 weeks with further CT images of the chest, abdomen and pelvis. Patients were excluded if the baseline or post-treatment CT scan was unavailable for review or was inadequate quality for quantitative image analysis.

Treatment records were pooled to analyze the clinical, laboratory and radiologic variables of selected patients. Clinical follow-up was collected from the electronic medical record and the Hepatopancreatobiliary Service prospectively maintained database. Variables with association to percent volume and diameter response were assessed using the Mann-Whitney U test for continuous variables. Spearman's correlation was used to assess non-parametric statistical dependence between two continuous variables. A p value of less than about 0.05 was considered statistically significant and about a 95% confident interval was. Clinical analyses were conducted using SPSS statistical software (Version 22.0; Armonk, N.Y.).

Exemplary CT Contrast Image Acquisition and Segmentation

Patients underwent standard CT imaging for pre-treatment and follow-up scans. The multidetector CT (e.g., Lightspeed 16 and VCT, GE Healthcare, Wisconsin) was employed for abdomen imaging with main parameters as: autoMA 220-380; a noise index 12-14; a rotation time of about 0.7-0.8 milliseconds; a scan delay of about 80 seconds. Index tumors for each patient were manually segmented by using Scout Liver (e.g., Pathfinder Technologies Inc., Tennessee).

Exemplary Prediction Model Design

An exemplary prediction model was constructed with the pre-treatment CT texture of the index tumor as a predictor, and the index tumor volume change rate and the longest dimension change rate as the outcome. The outcome (e.g., volume change and the longest dimension change) was obtained from the baseline scan and the follow-up scan. The data were randomly assigned to the model building set (e.g., n=93) or validation set (e.g., n=10). A least square boosted random forest regression model was tuned with learning rate of about 0.25, and the tree number of 40. A nine fold cross validation was used to construct the model, with nine regression models. Performance was evaluated with prediction error (e.g., mean error from these regression models) and root mean squared error ("RMSE"). A second exemplary model was constructed based on the longest dimension change rate in the axial plane, built using the same exemplary procedure.

Feature Extraction and Selection

There were 57 features obtained from the baseline index tumor volume. 16 first order statistics for the volume and the specific slice were extracted. The GLCM procedure algorithm generated 22 features. The run length, the fractal dimension, and the region property covered 11, 3 and 5 features respectively. (See, e.g., References 20-22 and 137). Feature selection was undertaken with univariate analysis applied to each of the 57 factors relating to the index tumor volume change rate. Ten resultant features (e.g., p<0.05) were chosen as input to the prediction model.

Exemplary Results

Percentage diameter change and percentage volume change were calculated based on the baseline and post-treatment CT scan. For the whole cohort, median percent diameter change was about −32.8% (range about −63% to about +13%) and median percent volume change was −about 69% (range about −97% to about +37%).

Cross validation based on the model building with the training set (e.g., n=93) from 9 regression models and validation test set (e.g., n=10) are listed in Table 17. The model building cross validation step utilized all of the training samples to construct 9 regression models, each model containing sub-training sets and sub-test sets. The prediction error for the model building cross validation is the average of the mean error from each regression models, similar for the RMSE. The prediction error and RMSE for the validation set was the average of the prediction error from the nine individual regression models.

Figure 28A:
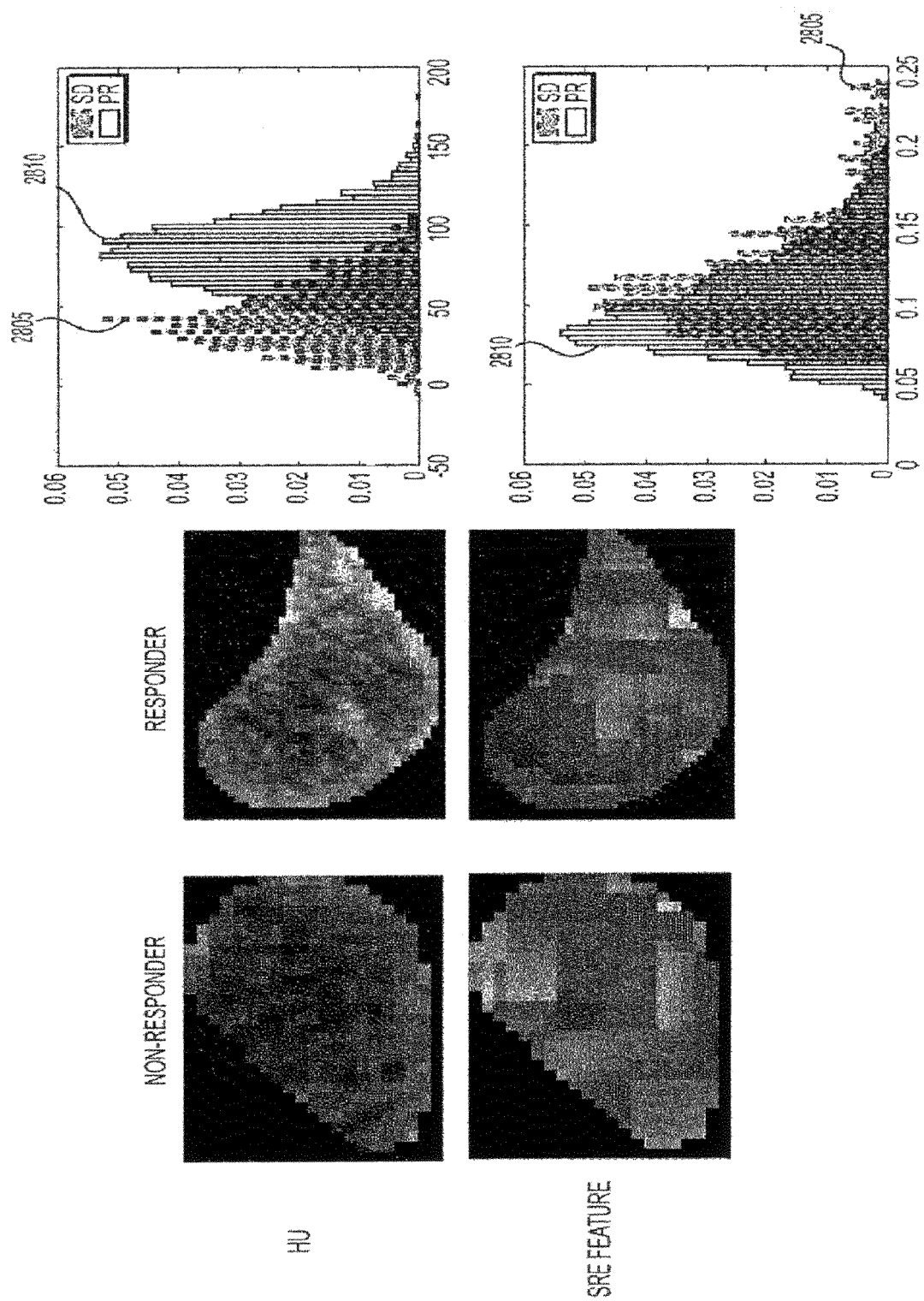
FIG. 28A is a set of images and corresponding histograms for an exemplary responder and non-responder according to an exemplary embodiment of the present disclosure.
Figure 28B:
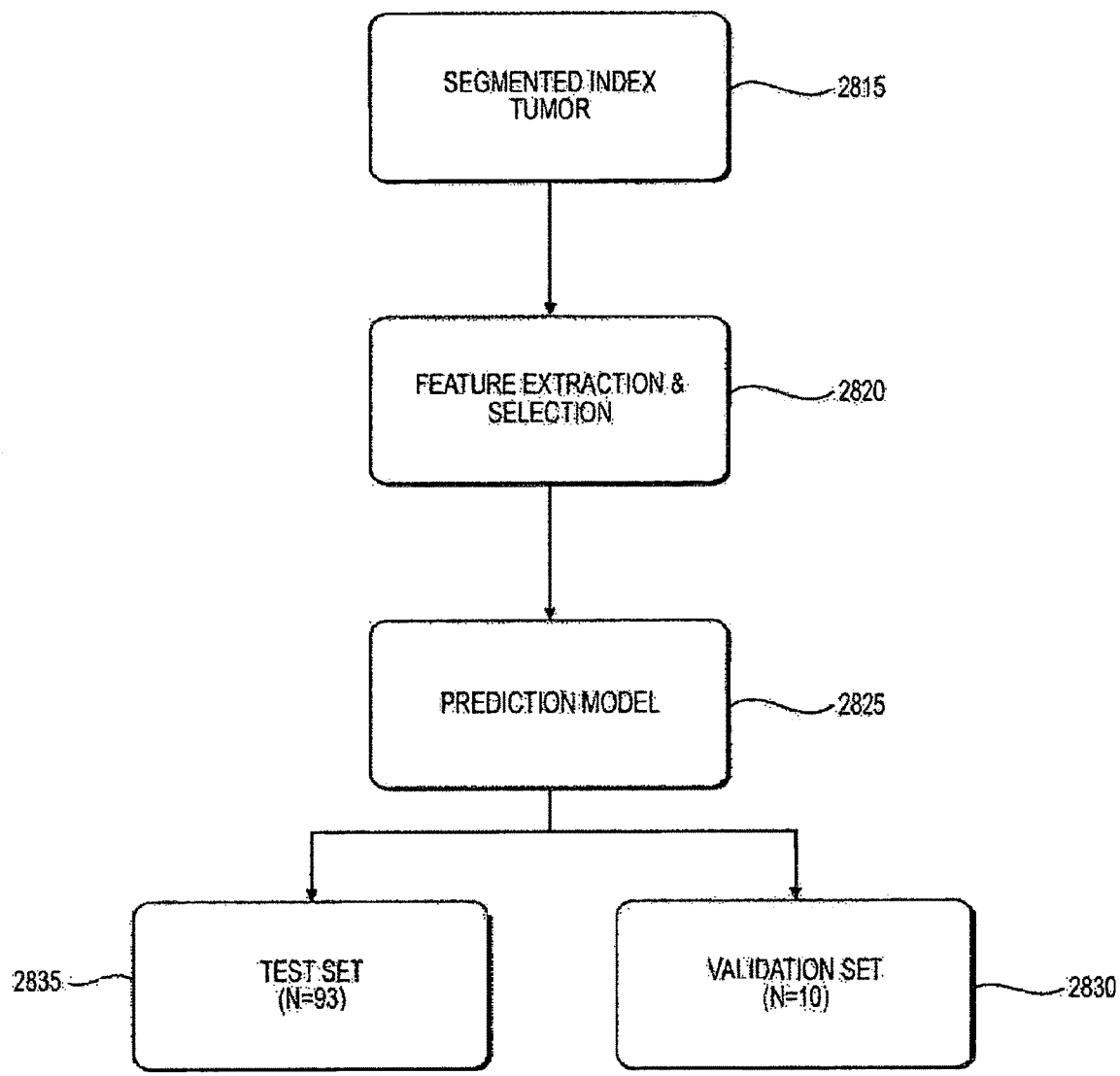
FIG. 28B is an exemplary flow diagram of a method for using a prediction model according to an exemplary embodiment of the present disclosure.

The mean HU density and the short run emphasis ("SRE") were the top two discriminatory features in the feature selection. The HU can reflect the linear attenuation coefficient of the tissue. The SRE can be obtained from the run length procedure emphasizing the shorter continuity of different gray levels. Mean HU values in partial responders by Response Evaluation Criteria in Solid Tumors were about 91.2 (e.g., n=56) and about 82.2 for stable disease (e.g., n=47). SRE for partial responders was lower than the stable disease group (e.g., 0.0864 vs. 0.098), suggesting that coarser grained image texture (e.g., more heterogeneity) may be related to better response. FIG. 28A shows a set of exemplary images, and corresponding histograms (e.g., SD 2805 and PR 2810), showing heterogeneity differences for responders and non-responders. Increased heterogeneity reflects higher contrast uptake, which may result in greater intake of chemotherapy to the tumor for better response. FIG. 2813 shows a flow diagram of an exemplary method for using a prediction model according to an exemplary embodiment of the present disclosure. For example, as shown in FIG. 28B, a segmented tumor index 2815 can be used in a feature extraction and selection procedure 2820. A prediction model 2825 can be used to predict a characteristic of a patient or of a tissue. An exemplary validation set 2830 (e.g., n=10) can be used, as well as an exemplary test set 2830 (e.g., n=93).

TABLE 17

Prediction results for model building and validation set.

| | Model Building | | Validation Set | |
| --- | --- | --- | --- | --- |
| | Error | RMSE | Error | RMSE |
| Volume Change | 20.3% | 26.29% | 13.32% | 15.45% |
| Longest Dimension Change | 15.43% | 18.79% | 10.13% | 11.98% |

Exemplary Discussion

Quantitative imaging features extracted from pre-treatment CT are promising predictors of volumetric response to chemotherapy in patients with CRLM. External validation is required prior to using these novel imaging marker in a clinical setting.

Exemplary Conclusion

Differences in enhancement in hepatic parenchyma and tumors can be quantified by texture analysis from underlying pixel variations on portal venous phase CT scans. These parenchymal and tumor differences in preoperative CT scans appear to correlate with postoperative insufficiency after major hepatic resections, protein expression in cholangiocarcinoma, hepatic recurrence in colorectal liver metastases, survival of pancreas cancer, and response to chemotherapy. These results have the potential to improve preoperative risk stratification by adding a measure of liver parenchymal quality to the standard assessments of liver remnant volume and non-invasive surveillance of disease progression.

Figure 29A:
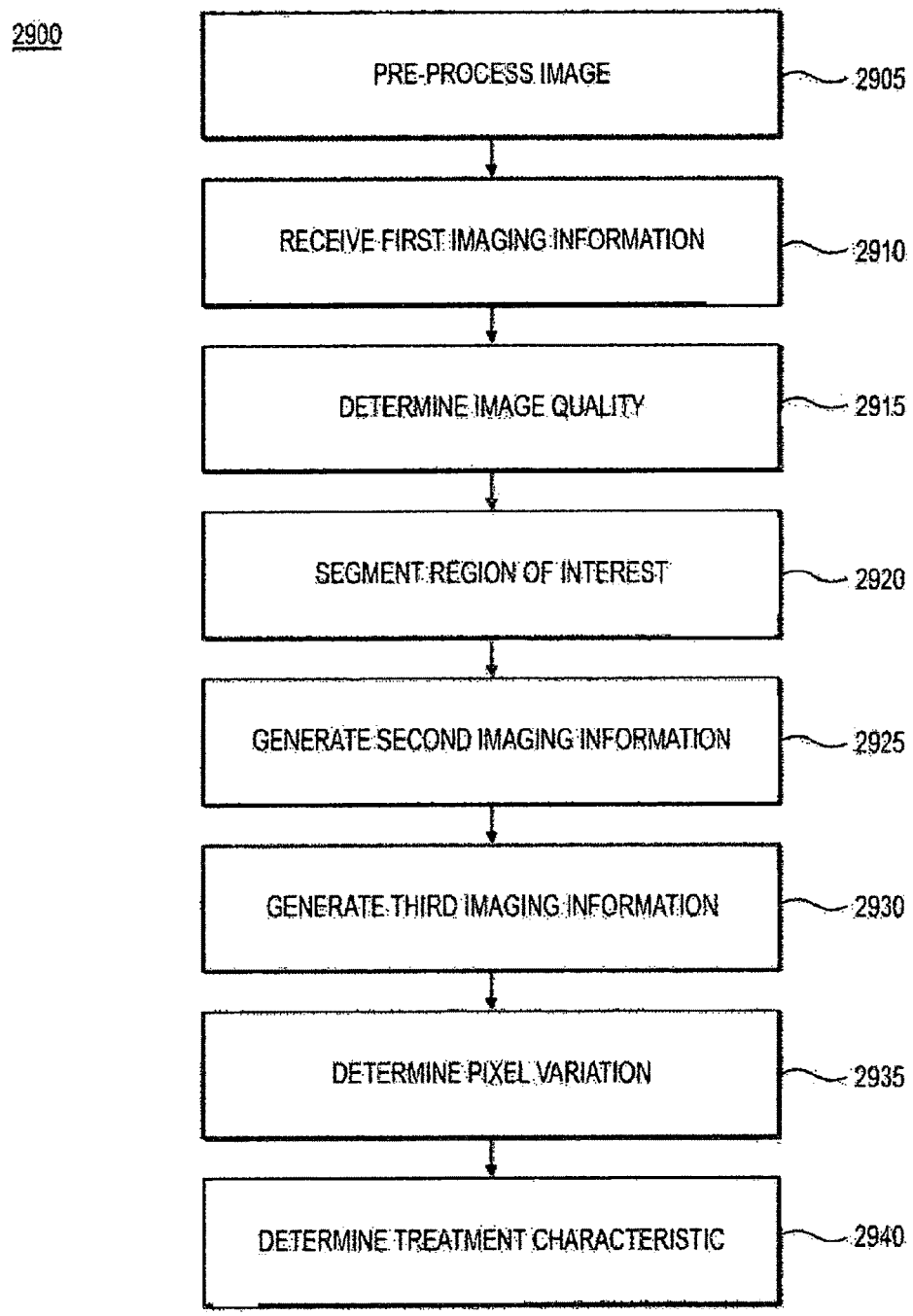
FIG. 29A is an exemplary flow diagram of an exemplary method for determining a pixel variation of a tissue in an image according to an exemplary embodiment of the present disclosure.

FIG. 29A shows an exemplary flow diagram of an exemplary method 2900 for determining a pixel variation of a tissue in an image according to an exemplary embodiment of the present disclosure. For example, at procedure 2905, an image (e.g., a CT image) can be pre-processed to determine a region of interest. At procedure 2910, first imaging information related to the at least one image (e.g., the pre-processed CT image) can be received. At procedure 2915, the image quality can be determined, and if the quality is determined to be sufficient, the region of interest can be segmented from the first imaging information at procedure 2920. At procedure 2925, second imaging information can be generated by subtracting a structure from the region of interest. Third imaging information related to a volume of the region of interest can be generated at procedure 2930, based on the second imaging information, which can be used to determine a pixel variation at procedure 2935. At procedure 2940, a treatment characteristic can be determined based on the pixel variation.

Figure 29B:
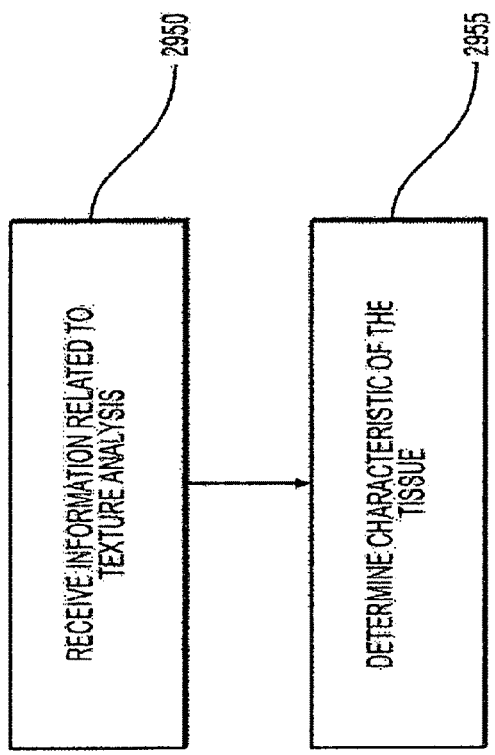
FIG. 29B is an exemplary flow diagram of an exemplary method for determining a characteristic of a tissue according to an exemplary embodiment of the present disclosure.

FIG. 29B shows an exemplary flow diagram of an exemplary method 2945 for determining a characteristic of a tissue according to an exemplary embodiment of the present disclosure. For example, at procedure 2950 information related to a texture analysis of a tissue can be received, and at procedure 2955, a characteristic of the tissue can be determined based on the texture analysis.

Figure 30:
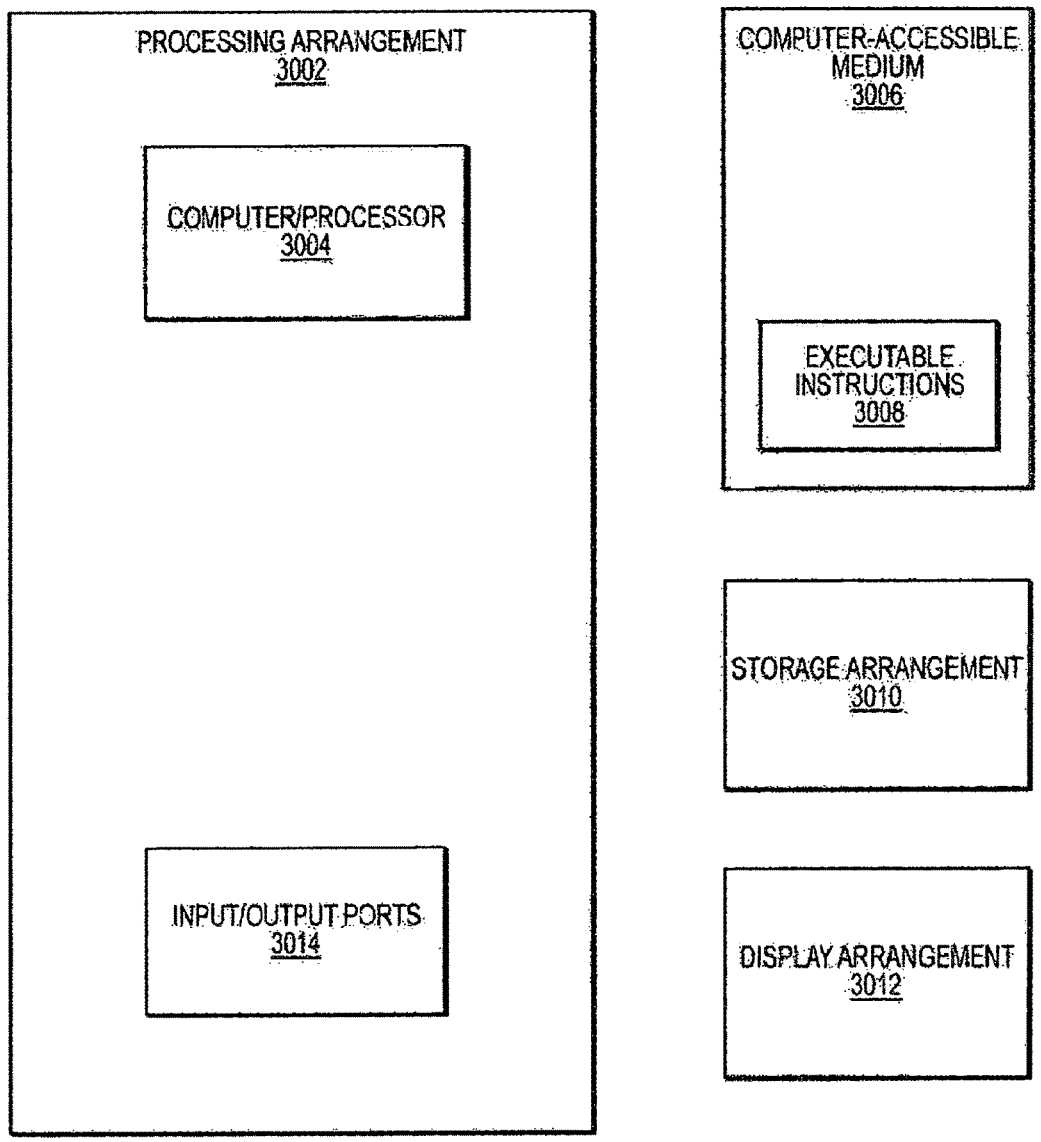
FIG. 30 is an illustration of an exemplary block diagram of an exemplary system in accordance with certain exemplary embodiments of the present disclosure.

FIG. 30 shows a block diagram of an exemplary embodiment of a system according to the present disclosure. For example, exemplary procedures in accordance with the present disclosure described herein can be performed by a processing arrangement and/or a computing arrangement 3002. Such processing/computing arrangement 3002 can be, for example entirely or a part of, or include, but not limited to, a computer/processor 3004 that can include, for example one or more microprocessors, and use instructions stored on a computer-accessible medium (e.g., RAM, ROM, hard drive, or other storage device).

As shown in FIG. 30, for example a computer-accessible medium 3006 (e.g., as described herein above, a storage device such as a hard disk, floppy disk, memory stick, CD-ROM, RAM, ROM, etc., or a collection thereof) can be provided (e.g., in communication with the processing arrangement 3002). The computer-accessible medium 3006 can contain executable instructions 3008 thereon. In addition or alternatively, a storage arrangement 3010 can be provided separately from the computer-accessible medium 3006, which can provide the instructions to the processing arrangement 3002 so as to configure the processing arrangement to execute certain exemplary procedures, processes and methods, as described herein above, for example.

Further, the exemplary processing arrangement 3002 can be provided with or include an input/output arrangement 3014, which can include, for example a wired network, a wireless network, the internet, an intranet, a data collection probe, a sensor, etc. As shown in FIG. 30, the exemplary processing arrangement 3002 can be in communication with an exemplary display arrangement 3012, which, according to certain exemplary embodiments of the present disclosure, can be a touch-screen configured for inputting information to the processing arrangement in addition to outputting information from the processing arrangement, for example. Further, the exemplary display 3012 and/or a storage arrangement 3010 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

Exemplary References

The following references are hereby incorporated by reference in their entirety.
1. Davnall F, Yip C S, Ljungqvist G, et al. Assessment of tumor heterogeneity: an emerging imaging tool for clinical practice? Insights into Imaging 2012; 3:573e589.
2. Miles K A, Ganeshan B, Griffiths M R, et al. Colorectal cancer: texture analysis of portal phase hepatic CT images as a potential marker of survival. Radiology 2009; 250: 114e452.
3. Ganeshan B, Burnand K, Young R, et al. Dynamic contrast-enhanced texture analysis of the liver: initial assessment in colorectal cancer. Investigative Radiol 2011; 46:160e168.
4. Romero-Gomez M, Gomez-Gonzalez E, Madrazo A, et al. Optical analysis of computed tomography images of the liver predicts fibrosis stage and distribution in chronic hepatitis C. Hepatology 2008; 47:810e816.
5. Barry B, Buch K, Soto J A, et al. Quantifying liver fibrosis through the application of texture analysis to diffusion weighted imaging. Magnetic Resonance Imaging 2014; 32: 84e90.
6. Dokmak S, Fteriche F S, Borscheid R, et al. 2012 Liver resections in the 21st century: we are far from zero mortality. HPB 2013; 15:908e915.
7. Jarnagin W R, Gonen M, Fong Y, et al. Improvement in perioperative outcome after hepatic resection: analysis of 1,803 consecutive cases over the past decade. Ann Surg 2002; 236: 397e406; discussion 406e407.
8. Schindl M J, Redhead D N, Fearon K C, et al. The value of re-sidual liver volume as a predictor of hepatic dysfunction and infection after major liver resection. Gut 2005; 54:289e296.

9. Kishi Y, Abdalla E K, Chun Y S, et al. Three hundred and one consecutive extended right hepatectomies: evaluation of outcome based on systematic liver volumetry. Ann Surg 2009; 250:540e548.
10. Shoup M, Gonen M, D'Angelica M, et al. Volumetric analysis predicts hepatic dysfunction in patients undergoing major liver resection. J Gastrointest Surg 2003; 7:325e330.
11. Hoekstra L T, de Graaf W, Nibourg G A, et al. Physiological and biochemical basis of clinical liver function tests: a review. Ann Surg 2013; 257:27e36.
12. Lam C M, Fan S T, Lo C M, Wong J. Major hepatectomy for hepatocellular carcinoma in patients with an unsatisfactory indocyanine green clearance test. Br J Surg 1999; 86: 1012e1017.
13. Wong J S, Wong G L, Chan A W, et al. Liver stiffness measurement by transient elastography as a predictor on posthepatectomy outcomes. Ann Surg 2013; 257: 922e928.
14. Marsman H A, van der Pool A E, Verheij J, et al. Hepatic stea-tosis assessment with CT or MRI in patients with colorectal liver metastases after neoadjuvant chemotherapy. J Surg Oncol 2011; 104:10e16.
15. Wibmer A, Prusa A M, Nolz R, et al. Liver failure after major liver resection: risk assessment by using preoperative gadoxetic acid-enhanced 3-TMR imaging. Radiology 2013; 269: 777e786.
16. Martin R C, Jaques D P, Brennan M F, Karpeh M. Achieving RO resection for locally advanced gastric cancer: is it worth the risk of multiorgan resection? J Am Coll Surg 2002; 194: 568e577.
17. Kleiner D E, Brunt E M, Van Natta M, et al. Design and validation of a histological scoring system for nonalcoholic fatty liver disease. Hepatology 2005; 41:1313e1321.
18. Rubbia-Brandt L, Audard V, Sartoretti P, et al. Severe hepatic sinusoidal obstruction associated with oxaliplatin-based chemotherapy in patients with metastatic colorectal cancer. Ann Oncol 2004; 15:460e466.
19. Russ J C. The Image Processing Handbook. 6th ed. Boca Raton: CRC Press; 2011. xviii, 867.
20. Haralick R M, Shanmugam K, Dinstein I H. Textural features for image classification. Systems, Man and Cybernetics, IEEE Transactions on. 1973; SMC-3: 610e621.
21. Haralick R M. Statistical and structural approaches to texture. Proceedings of the IEEE 1979; 67:786e804.
22. Soh L K, Tsatsoulis C. Texture analysis of SAR sea ice imagery using gray level co-occurrence matrices. Geoscience and Remote Sensing, IEEE Transactions on 1999; 37:780e795.
23. van den Broek M A, Olde Damink S W, Dejong C H, et al. Liver failure after partial hepatic resection: definition, pathophysiology, risk factors and treatment. Liver Int 2008; 28: 767e780.
24. Lock J F, Reinhold T, Malinowski M, Pratschke J, Neuhaus P, Stockmann M. The costs of postoperative liver failure and the economic impact of liver function capacity after extended liver resection—a single-center experience. Langenbecks Arch Surg 2009; 394(6):1047-1056.
25. Julesz B, Gilbert E N, Shepp L A, Frisch H L. Inability of humans to discriminate between visual textures that agree in second-order statistics-revisited. Perception 1973; 2:391e405.
26. Ohanian P P, Dubes R C. Performance evaluation for four classes of textural features.
Pattern Recognition 1992; 25: 819e833.
27. Huang Y L, Chen J H, Shen W C. Diagnosis of hepatic tumors with texture analysis in nonenhanced computed tomography images. Acad Radiol 2006; 13:713e720.
28. Harrison L C, Luukkaala T, Pertovaara H, et al. Non-Hodgkin lymphoma response evaluation with MRI texture classification. J Experiment Clin Cancer Res 2009; 28:87.
29. O'Connor J P, Rose C J, Jackson A, et al. DCE-MRI bio-markers of tumour heterogeneity predict CRC liver metastasis shrinkage following bevacizumab and FOL-FOX-6. Br J Cancer 2011; 105:139e145.
30. Yang X, Tridandapani S, Beitler J J, et al. Ultrasound GLCM texture analysis of radiation-induced parotid-gland injury in head-and-neck cancer radiotherapy: an in vivo study of late toxicity. Med Phys 2012; 39:5732e5739.
31. Hunter L A, Krafft S, Stingo F, et al. High quality machine robust image features: Identification in non-small cell lung cancer computed tomography images. Med Phys 2013; 40: 121916.
32. Aguirre D A, Behling C A, Alpert E, et al. Liver fibrosis: noninvasive diagnosis with double contrast materiale enhanced MR imaging. Radiology 2006; 239:425e437.
33. Ratti F, Cipriani F, Ferla F, et al. Hilar cholangiocarcinoma: preoperative liver optimization with multidisciplinary approach. Toward a better outcome. World J Surg 2013; 37: 1388e1396.
34. Marmé D, Fusenig N. Tumor angiogenesis: basic mechanisms and cancer therapy: Springer-Verlag; 2008.
35. Ding Z, Yang L, Xie X, Xie F, Pan F, Li J, et al. Expression and significance of hypoxia-inducible factor-1 alpha and MDR1/P-glycoprotein in human colon carcinoma tissue and cells. Journal of cancer research and clinical oncology. 2010; 136:1697-707.
36. Perez-Sayans M, Supuran C T, Pastorekova S, Suarez-Penaranda J M, Pilar G D, Barros-Angueira F, et al. The role of carbonic anhydrase IX in hypoxia control in OSCC. Journal of oral pathology & medicine: official publication of the International Association of Oral Pathologists and the American Academy of Oral Pathology. 2013; 42:1-8.
37. Thomas S, Harding M A, Smith S C, Overdevest J B, Nitz M D, Frierson H F, et al. CD24 is an effector of HIF-1-driven primary tumor growth and metastasis. Cancer Res. 2012; 72:5600-12.
38. Cleven A H, van Engeland M, Wouters B G, de Bruine A P. Stromal expression of hypoxia regulated proteins is an adverse prognostic factor in colorectal carcinomas. Cellular oncology: the official journal of the International Society for Cellular Oncology. 2007; 29:229-40.
39. Lee J H, Jin Y, He G, Zeng S X, Wang Y V, Wahl G M, et al. Hypoxia activates tumor suppressor p53 by inducing ATR-Chk1 kinase cascade-mediated phosphorylation and consequent 14-3-3gamma inactivation of MDMX protein. J Biol Chem. 2012; 287:20898-903.
40. Thou S, Gu L, He J, Zhang H, Thou M. MDM2 regulates vascular endothelial growth factor mRNA stabilization in hypoxia. Mol Cell Biol. 2011; 31:4928-37.
41. Yopp A C, Schwartz L H, Kemeny N, Gultekin D E L Gonen M, Bamboat Z, et al. Antiangiogenic therapy for primary liver cancer: correlation of changes in dynamic contrast-enhanced magnetic resonance imaging with tissue hypoxia markers and clinical response. Ann Surg Oncol. 2011; 18:2192-9.

42. Shia J, Klimstra D S, Li A R, Qin J, Saltz L, Teruya-Feldstein J, et al. Epidermal growth factor receptor expression and gene amplification in colorectal carcinoma: an immunohistochemical and chromogenic in situ hybridization study. Modern pathology: an official journal of the United States and Canadian Academy of Pathology, Inc. 2005; 18:1350-6.
43. Marotta L L, Almendro V, Marusyk A, Shipitsin M, Schemme J, Walker S R, et al. The JAK2/STAT3 signaling pathway is required for growth of CD44(+)CD24(-) stem cell-like breast cancer cells in human tumors. J Clin Invest. 2011; 121:2723-35.
44. Simpson A L, Geller D A, Hemming A W, Jarnagin W R, Clements L W, D'Angelica M I, et al. Liver planning software accurately predicts postoperative liver volume and measures early regeneration. J Am Coll Surg. 2014; 219:199-207.
45. Russ J C. The image processing handbook. 6th ed. Boca Raton: CRC Press; 2011.
46. Kemeny N E, Schwartz L, Gonen M, Yopp A, Gultekin D, D'Angelica M I, et al. Treating primary liver cancer with hepatic arterial infusion of floxuridine and dexamethasone: does the addition of systemic bevacizumab improve results? Oncology 2011; 80:153-9.
47. Jarnagin W R, Schwartz L H, Gultekin D H, Gonen M, Haviland D, Shia J, et al. Regional chemotherapy for unresectable primary liver cancer: results of a phase II clinical trial and assessment of DCE-MRI as a biomarker of survival. Annals of oncology: official journal of the European Society for Medical Oncology/ESMO. 2009; 20:1589-95.
48. Thelen A, Scholz A, Weichert W, Wiedenmann B, Neuhaus P, Gessner R, et al. Tumor-associated angiogenesis and lymphangiogenesis correlate with progression of intrahepatic cholangiocarcinoma. Am J Gastroenterol. 2010; 105:1123-32.
49. Yoshikawa D, Ojima H, Iwasaki M, Hiraoka N, Kosuge T, Kasai S, et al. Clinicopathological and prognostic significance of EGFR, VEGF, and HER2 expression in cholangiocarcinoma. British journal of cancer. 2008; 98:418-25.
50. Cuzick J, Dowsett M, Pineda S, Wale C, Salter J, Quinn E, et al. Prognostic value of a combined estrogen receptor, progesterone receptor, Ki-67, and human epidermal growth factor receptor 2 immunohistochemical score and comparison with the Genomic Health recurrence score in early breast cancer. Journal of clinical oncology: official journal of the American Society of Clinical Oncology. 2011; 29:4273-8.
51. Diehn M, Nardini C, Wang D S, McGovern S, Jayaraman M, Liang Y, et al. Identification of noninvasive imaging surrogates for brain tumor gene-expression modules. Proc Natl Acad Sci USA. 2008; 105:5213-8.
52. Segal E, Sirlin C B, Ooi C, Adler A S, Gollub J, Chen X, et al. Decoding global gene expression programs in liver cancer by noninvasive imaging. Nature biotechnology. 2007; 25:675-80.
53. Su M C, Hsu C, Kao Jeng Y M. CD24 expression is a prognostic factor in intrahepatic cholangiocarcinoma. Cancer letters. 2006; 235:34-9.
54. Gatenby R A, Grove O, Gillies R J. Quantitative imaging in cancer evolution and ecology. Radiology. 2013; 269: 8-15.
55. Davenport M S, Khalatbari S, Liu P S, Maturen K E, Kaza R K, Wasnik A P, et al. Repeatability of diagnostic features and scoring systems for hepatocellular carcinoma by using MR imaging. Radiology. 2014; 272:132-42.
56. Keeratichamroen S, Leelawat K, Thongtawee T, Narong S, Aegem U, Tujinda S, et al. Expression of CD24 in cholangiocarcinoma cells is associated with disease progression and reduced patient survival. International journal of oncology. 2011; 39:873-81.
57. Agrawal S, Kuvshinoff B W, Khoury T, Yu J, Javle M M, LeVea C, et al. CD24 expression is an independent prognostic marker in cholangiocarcinoma. J Gastrointest Surg. 2007; 11:445-51.
58. Tortora G, Ciardiello F, Gasparini G. Combined targeting of EGFR-dependent and VEGF-dependent pathways: rationale, preclinical studies and clinical applications. Nature clinical practice Oncology. 2008; 5:521-30.
59. National Comprehensive Cancer Network. NCCN clinical practice guidelines in oncology; version 3.2014. Available at http://www.neen.org/professionals/physician_gls/pdf/colon.pdf. Accessed Aug. 20, 2014.
60. Mascaux C, Wynes M W, Kato Y, Tran C, Asuncion B R, Zhao J M, et al. EGFR protein expression in non-small cell lung cancer predicts response to an EGFR tyrosine kinase inhibitor—a novel antibody for immunohistochemistry or AQUA technology. Clin Cancer Res. 2011; 17:7796-807.
61. Lambrechts D, Lenz H J, de Haas S. Carmeliet P, Scherer S J. Markers of response for the antiangiogenic agent bevacizumab. Journal of clinical oncology: official journal of the American Society of Clinical Oncology. 2013; 31:1219-30.
62. Gonzalez R C. Digital image processing. 3rd ed. Upper Saddle River, N.J: Prentice Hall; 2008. 954 p.
63. Haralick R M, Shanmugam K, Dinstein I. Textural Features for Image Classification. IEEE Trans Syst Man Cybern. 1973 November; 3(6):610-21.
64. Haralick R M. Statistical and structural approaches to texture. Proc IEEE. 1979; 67(5):786-804.
65. Leen-Kiat Soh, Tsatsoulis C. Identifying classes in SAR sea ice imagery using correlated texture. IEEE; 1997 [cited 2014 Dec. 17]. p. 1177-9. Available from: http://ieeexplore.ieee.org/lpdcos/epic03/wrapper.htm?arnumber=606389
66. Callery M P, Chang K J, Fishman E K, Talamonti M S, William Traverso L, Linehan D C. Pretreatment Assessment of Resectable and Borderline Resectable Pancreatic Cancer: Expert Consensus Statement. Ann Surg Oncol. 2009 July; 16(7):1727-33.
67. O'Reilly E M, Perelshteyn A, Jarnagin W R, Schaffner M, Gerdes H, Capanu M, et al. A Single-Arm, Nonrandomized Phase II Trial of Neoadjuvant Gemcitabine and Oxaliplatin in Patients With Resectable Pancreas Adenocarcinoma: Ann Surg. 2014 July; 260(1):142-8.
68. Yamamoto T, Sugiura T, Mizuno T, Okamura Y, Aramaki T, Endo M, et al. Preoperative FDG-PET Predicts Early Recurrence and a Poor Prognosis After Resection of Pancreatic Adenocarcinoma. Ann Surg Oncol [Internet]. 2014 Sep. 5 [cited 2014 Dec. 17]; Available from: http://link.springer.com/10.1245/s10434-014-4046-2
69. Dang M, Lysack J T, Wu T, Matthews T W, Chandarana S P, Brockton N T, et al. MRI Texture Analysis Predicts p53 Status in Head and Neck Squamous Cell Carcinoma. Am J Neuroradiol [Internet]. 2014 Sep. 25 [cited 2014 Dec. 17]; Available from: http://wvvw.ajnr.org/cgi/doi/10.3174/ajnr.A4110
70. Chicklore S, Goh V, Siddique M, Roy A, Marsden P K, Cook G J R. Quantifying tumour heterogeneity in 18F-FDG PET/CT imaging by texture analysis. Eur J Nucl Med Mol Imaging. 2013 January; 40(1):133-40.

71. Hattori Y, Gabata T, Zen Y, Mochizuki K, Kitagawa H, Matsui O. Poorly enhanced areas of pancreatic adenocarcinomas on late-phase dynamic computed tomography: comparison with pathological findings. Pancreas. 2010 November; 39(8):1263-70.
72. Hata H, Mori H, Matsumoto S, Yamada Y, Kiyosue H, Tanoue S, et al. Fibrous stroma and vascularity of pancreatic carcinoma: correlation with enhancement patterns on CT. Abdom Imaging. 2010 April; 35(2):172-80.
73. Aerts HJWL, Velazquez E R, Leijenaar R T H, Parmar. C, Grossmann P, Cavalho S, et al. Decoding tumour phenotype by noninvasive imaging using a quantitative radiomics approach. Nat Commun. 2014; 5:4006.
74. Song X, Liu X, Chi W, Liu Y, Wei L, Wang X, et al. Hypoxia-induced resistance to cisplatin and doxorubicin in non-small cell lung cancer is inhibited by silencing of HIP-1 alpha gene. Cancer Chemother Pharmacol. 2006 December; 58(6):776-84.
75. Harrison L B, Chadha M, Hill R J, Hu K, Shasha D. Impact of tumor hypoxia and anemia on radiation therapy outcomes. The Oncologist. 2002; 7(6):492-508.
76. Swinson D E B, Jones J L, Richardson D, Wykoff C, Turley H, Pastorek J, et al. Carbonic anhydrase IX expression, a novel surrogate marker of tumor hypoxia, is associated with a poor prognosis in non-small-cell lung cancer. J Clin Oncol Off J Am Soc Clin Oncol. 2003 Feb. 1; 21(3):473-82.
77. Zhao T, Ren H, Li J, Chen J, Zhang H, Xin W, et al. LASP1 is a HIF-1 target gene critical for metastasis of pancreatic cancer. Cancer Res [Internet]. 2014 Nov. 10 [cited 2014 Dec. 17]; Available from: http://cancerres.aacrjournals.org/cgi/doi/10.1158/0008-5472.CAN-14-2040.
78. Siegel R, DeSantis C, Virgo K, Stein K, Mariotto A, Smith T, et al. Cancer treatment and survivorship statistics, 2012. C A Cancer J Clin. 2012 August; 62(4):220-41.
79. Mena J, Biffin A, Radcliffe A G, Stamatakis 3D, Steele R J. Population-based audit of colorectal cancer management in two UK health regions. Colorectal Cancer Working Group, Royal College of Surgeons of England Clinical Epidemiology and Audit Unit. Br J Surg. 1997 December; 84(12):1731-6.
80. Fong Y, Former J, Sun R L, Brennan M F, Blumgart L H. Clinical score for predicting recurrence after hepatic resection for metastatic colorectal cancer: analysis of 1001 consecutive cases. Ann Surg. 1999; 230(3):309-21.
81. House M G, Ito H, Gonen M, Fong Y, Allen P J, DeMatteo R P, et. al. Survival after hepatic resection for metastatic colorectal cancer: trends in outcomes for 1,600 patients during two decades at a single institution. J Am Coll Surg. 2010; 210(5):744-52, 752-5.
82. D'Angelica M, Komprat P, Gonen M, DeMatteo R P, Fong Y, Blumgart L H, et al. Effect on Outcome of Recurrence Patterns After Hepatectomy for Colorectal Metastases. Ann Surg Oncol. 2011 April; 18(4):1096-103.
83. Portier G, Elias D, Bouche O, Rougier P, Bosset J F, Saric J, et al. Multicenter randomized trial of adjuvant fluorouracil and folinic acid compared with surgery alone after resection of colorectal liver metastases: FFCD ACHBTH AURC 9002 trial. J Clin Oncol. 2006; 24(31):4976-82.
84. Kemeny N, Huang Y, Cohen A M, Shi W, Conti J A, Brennan M F, et al, Hepatic arterial infusion of chemotherapy after resection of hepatic metastases from colorectal cancer. N Engl J Med. 1999; 341(27):2039-48.
85. Goéré D, Benhaim L, Bonnet S, Malka D, Faron M, Elias D, et al. Adjuvant chemotherapy after resection of colorectal liver metastases in patients at high risk of hepatic recurrence: a comparative study between hepatic arterial infusion of oxaliplatin and modern systemic chemotherapy. Ann Surg. 2013; 257(1):114-20.
86. Kemeny N. Phase I Trial of Systemic Oxaliplatin Combination Chemotherapy With Hepatic Arterial Infusion in Patients With Unresectable Liver Metastases From Colorectal Cancer. J Clin Oncol. 2005 June; 23(22):4888-96.
87. Nordlinger B, Guiguet M, Vaillant J C, Balladur P, Boudjema K, Bachellier P, et al. Surgical resection of colorectal carcinoma metastases to the liver. A prognostic scoring system to improve case selection; based on 1568 patients. Association Française de Chirurgie. Cancer. 1996 April; 77(7):1254-62.
88. Rees M, Tekkis P P, Welsh F K S, O'Rourke T, John T G. Evaluation of long-term survival after hepatic resection for metastatic colorectal cancer: a multifactorial model of 929 patients. Ann Surg. 2008 January; 247(1): 125-35.
89. Zakaria S, Donohue J H, Que F G, Farnell M B, Schleck C D, Ilstrup D M, et al. Hepatic resection for colorectal metastases: value for risk scoring systems? Ann Surg. 2007 August; 246(2):183-91.
90. Leen E. The detection of occult liver metastases of colorectal carcinoma. J Hepatobiliary Pancreat Surg. 1999; 6(1):7-15.
91. Conzelmann M, Linnemann U, Berger M R. Detection of disseminated tumour cells in the liver of colorectal cancer patients. Eur J Surg Oncol J Eur Soc Surg Oncol Br Assoc Surg Oncol. 2005 February; 31(1):38-44.
92. Rao S-X, Lambregts D M, Schnerr R S, van Ommen W, van Nijnatten Ti, Martens M H, et al. Whole-liver C T texture analysis in colorectal cancer: Does the presence of liver metastases affect the texture of the remaining liver? United Eur Gastroenterol J. 2014 December; 2(6):530-8.
93. Ganeshan B, Miles K A, Young R C D, Chatwin C. R. Hepatic entropy and uniformity: additional parameters that can potentially increase the effectiveness of contrast enhancement during abdominal C T. Clin Radiol. 2007 August; 62(8):761-8.
94. Simpson A L, Adams L B, Allen P J, D'Angelica M I, DeMatteo R P, Fong Y, et al. Texture Analysis of Preoperative C T Images for Prediction of Postoperative Hepatic Insufficiency: A Preliminary Study. J Am Coll Surg. 2015; 220(3):339-46.
95. Wu Z, Matsui O, Kitao A, Kozaka K, Koda W, Kobayashi S, et al. Hepatitis C Related Chronic Liver Cirrhosis: Feasibility of Texture Analysis of MR Images for Classification of Fibrosis Stage and Necroinflammatory Activity Grade. PLoS One. 2015; 10(3):e0118297.
96. Ba-Ssalamah A, Muin D, Schernthaner R, Kulinna-Cosentini C, Bastati N, Stift J, et al. Texture-based classification of different gastric tumors at contrast-enhanced CT. Eur J Radiol. Elsevier Ireland Ltd; 2013; 82(10): e537-43.
97. Ng F, Kozarski R, Miles K A, Goh V, Ganeshan. B. Assessment of primary colorectal cancer heterogeneity by using whole-tumor texture analysis: contrast-enhanced CT texture as a biomarker of 5-year survival. Radiology. 2013; 266(1):177-84.
98. Hayano K, Yoshida H, Zhu A X, Sahani D V. Fractal analysis of contrast-enhanced CT images to predict survival of patients with hepatocellular carcinoma treated with sumitinib. Dig Dis Sci. 2014 August; 59(8):1996-2003.
99. Miles K A, Ganeshan B, Griffiths M R, Young R C D, Chatwin C R. Colorectal cancer: texture analysis of portal phase hepatic CT images as a potential marker of survival. Radiology. 2009; 250(2):444-52.
100. Lubner M G, Stabo N, Lubner S J, del Rio A M, Song C, Halberg R B, et al. C T textural analysis of hepatic metastatic colorectal cancer: pre-treatment tumor heterogeneity correlates with pathology and clinical outcomes. Abdom imaging. 2015 May 13;
101. Chun Y S, Vauthey J-N, Boonsirikamchai P, Maru D M, Kopetz S, Palavecino M, et al. Association of computed tomography morphologic criteria with pathologic response and survival in patients treated with bevacizumab for colorectal liver metastases. JAMA. American Medical Association; 2009 Dec. 2; 302(21):2338-44.
102. Wolf P S, Park J O, Bao F, Allen P J, DeMatteo R P, Fong Y, et al. Preoperative chemotherapy and the risk of hepatotoxicity and morbidity after liver resection for metastatic colorectal cancer: a single institution experience. J Am Coll Surg. 2013; 216(1):41-9.
103. Basch E, Reeve B B, Mitchell S A, Clauser S B, Minasian L M, Dueck A C, et al. Development of the National Cancer Institute's patient-reported outcomes version of the common terminology criteria for adverse events (PRO-CTCAE). J Natl Cancer Inst. 2014 September; 106(9).
104. Kleiner D E, Brunt E M, Van Natta M, Behling C, Contos M. J. Cummings O W, et al. Design and validation of a histological scoring system for nonalcoholic fatty liver disease. Hepatology. 2005; 41(6):1313-21.
105. Rubbia-Brandt L, Audard V, Sartoretti P, Roth A D, Brezault C, Le Charpentier M, et al. Severe hepatic sinusoidal obstruction associated with oxaliplatin-based chemotherapy in patients with metastatic colorectal cancer. Ann Oncol. 2004; 15(3):460-6.
106. Poultsides G A, Bao F, Servais E L, Hernandez-Boussard T, DeMatteo R P, Allen P J, et al. Pathologic Response to Preoperative Chemotherapy in Colorectal Liver Metastases: Fibrosis, not Necrosis, Predicts Outcome. Ann Surg Oncol. 2012; 19(9):2797-804.
107. Haralick R M, Shanmugam K, Dinstein I. Textural Features for Image Classification. Syst Man Cybern IEEE Trans. 1973; SMC-3(6):610-21.
108. Haralick R M. Statistical and structural approaches to texture. Proc IEEE. 1979; 67(5):786-804.
109. Soh L-K, Tsatsoulis C. Texture analysis of SAR sea ice imagery using gray level co-occurrence matrices. IEEE Transactions on Geoscience and Remote Sensing. 1999. p. 780-95.
110. van der Wal G E, Gouw A S H, Kamps JAAM, Moorlag H E, Bulthuis M L C, Molema G, et al. Angiogenesis in Synchronous and Metachronous Colorectal Liver Metastases: The Liver as a Permissive Soil. Ann Surg. 2012 January; 255(1):86-94.
111. van der Wal G E, Gouw A S H, Kamps JAAM, Moorlag H E, Bulthuis M L C, Molema G, et al. Reply to Letter: "Markers of Angiogenesis in Synchronous and in Metachronous Colorectal Hepatic Metastases." Ann Surg. 2015 January; 261(1):e20-1.
112. Eveno C, Hainaud P, Rampanou A, Bonnin P, Bakhouche S, Dupuy E, et al. Proof of prometastatic niche induction by hepatic stellate cells. J Surg Res. 2015 April; 194(2):496-504.
113 Hoshino A, Costa-Silva B, Shen T-L, Rodrigues G, Hashimoto A, Tesic Mark M, et al. Tumour exosome integrins determine organotropic metastasis. Nature. 2015; 1-19.
114. Costa-Silva B, Aiello N M, Ocean A J, Singh S, Zhang H, Thakur B K, et al. Pancreatic cancer exosomes initiate pre-metastatic niche formation in the liver. Nat Cell Biol. 2015; 17(6):1-7.
115 Lorenz M, Müller H H, Schramm H, Gassel H J, Rau H G, Ridwelski K, et al. Randomized trial of surgery versus surgery followed by adjuvant hepatic arterial infusion with 5-fluorouracil and folinic acid for liver metastases of colorectal cancer. German Cooperative on Liver Metastases (Arbeitsgruppe Lebermetastasen). Ann Surg. 1998 December; 228(6):756-62.
116. Yamaguchi T, Mori T, Takahashi K, Matsumoto H, Miyamoto H, Kato T. A new classification system for liver metastases from colorectal cancer in Japanese multicenter analysis. Hepatogastroenterology. 2008 February; 55(81): 173-8.
117. Iwatsuki S, Dvorchik I, Madariaga J R, Marsh J W, Dodson F, Bonham A C, et al. Hepatic resection for metastatic colorectal adenocarcinoma: a proposal of a prognostic scoring system. J Am Coll Surg. 1999 September; 189(3):291-9.
118. Kanemitsu Y, Kato T. Prognostic models for predicting death after hepatectomy in individuals with hepatic metastases from colorectal cancer. World J Surg. 2008 June; 32(6):1097-107.
119. Lehmann K, Rickenbacher A, Weber A, Pestalozzi B C, Clavien P-A. Chemotherapy Before Liver Resection of Colorectal Metastases: Friend or Foe? Ann Surg 2012 February; 255(2):237-47.
120. Allen P J, Kemeny N, Jarnagin W, DeMatteo R, Blumgart L, Fong Y. Importance of response to neoadjuvant chemotherapy in patients undergoing resection of synchronous colorectal liver metastases. J Gastrointest Surg Off J Soc Surg Aliment Tract. 2003 January; 7(1): 109-15; discussion 116-7.
121. N. Howlader, A. M. Noone, M. Krapcho, J. Garshell, D. Miller, S. F. Altekruse, C. Kosary, M. Yu, J. Ruhl, Z. Tatalovich, A. Mariotto, D. R. Lewis, H. S. Chen, E. J. Feuer, and C. K. (eds), "SEER cancer statistics review, 1975-2012, National Cancer Institute."
122. A. C. Society, "Cancer facts & figures, 2014," Atlanta American Cancer Society (2014).
123. M. F. Brennan, M. W. Kattan, D. Klimstra, and K. Conlon, "Prognostic nomogram for patients undergoing resection for adenocarcinoma of the pancreas," Annals of Surgery 240(2), 293-298 (2011).
124. C. L. Hallemeier, M. Botros, M. M. Corsini, M. G. Haddock, L. L. Gunderson, and R. C. Miller, "Preoperative C A 19-9 level is an important prognostic factor in patients with pancreatic adenocarcinoma treated with surgical resection and adjuvant concurrent chemoradiotherapy," American Journal of Clinical Oncology 34(6), 567-572 (2011).
125. A. Bilici, "Prognostic factors related with survival in patients with pancreatic adenocarcinoma," World Journal of Gastroenterology 20(31), 10802-10812 (2014).
126. M. M. Al-Hawary, I. R. Francis, S. T. Chari, E K. Fishman, D. M. Hough, D. S. Lu, M. Macari, A. J. Megibow, F. H. Miller, K. J. Mortele, N. B. Merchant, R. M. Minter, E. P. Tamm, D. V. Sahani, and D. M. Simeone, "Pancreatic ductal adenocarcinoma radiology reporting template: consensus statement of the society of abdominal radiology and the american pancreatic association," Radiology 270(1), 248-260 (2014).
127. S. H. Yoon, J. M. Lee, J. Y. Cho, K. B. Lee, J. E. Kim, S. K. Moon, S. J. Kim, J. H. Baek, S. H. Kim, S. H. Kim, J. Y. Lee, J. K. Han, and D. I. Choi, "Small ($r$=20 mm)

127. (cont.) pancreatic adenocarcinomas: Analysis of enhancement patterns and secondary signs with multiphasic multidetector CT," Radiology 259(2), 442-452 (2011).
128. M. Erkan, C. R. Erkan, C. W. Michalski, S. Deucker, D. Sauliunaite, S. Streit, I. Esposito, H. Friess, and J. Kleeff, "Cancer-stellate cell interactions perpetuate the hypoxia-fibrosis cycle in pancreatic ductal adenocarcinoma," Neoplasia 11(5), 497-508 (2009).
129. R. A. Gatenby, O. Grove, and R. J. Gillies, "Quantitative imaging in cancer evolution and ecology," Radiology 269(1), 8-15 (2013).
130. F. Ng, B. Ganeshan, R. Kozarski, K. A. Miles, and V. Goh, "Assessment of primary colorectal cancer heterogeneity by using whole-tumor texture analysis: contrast-enhanced ct texture as a biomarker of 5-year survival," Radiology 266(1), 177-184 (2013).
131. Y. Balagurunathan, Y. Gu, H. Wang, V. Kumar, O. Grove, S. Hawkins, J. Kim, D. B. Goldgof, L. O. Hall, R. A. Gatenby, and R. J. Gillies, "Reproducibility and prognosis of quantitative features extracted from ct images," Translational Oncology 7(1), 72-87 (2014).
132. M. C. Lloyd, P. A.-Nandyala, C. N. Purohit, N. Burke, D. Coppola, and M. M. Bui, "Using image analysis as a tool for assessment of prognostic and predictive biomarkers for breast cancer: How reliable is it?," Journal of Pathology Informatics 1, 1-29 (2013).
133. K. K. Pang and T. Hughes, "MR imaging of the musculoskeletal soft tissue mass: is heterogeneity a sign of malignancy?," Journal of the Chinese Medical Association 66(11), 655-661 (2003).
134. J. Chakrabortya, L. Langdon-Embrya, J. G. Escalonb, P. J. Allena, M. A. Loweryc, E. M. O'Reillyc, R. K. G. Dob, and A. L. Simpsona, "Texture analysis for survival prediction of pancreatic ductal adenocarcinoma patients with neoadjuvant chemotherapy," in SPIE Medical Imaging-2015, accepted.
135. E. M. O'Reilly, A. Perelshteyn, W. R. Jarnagin, M. Schattner, H. Gerdes, M. Capanu, L. H. Tang, J. LaValle, C. Winston, R. P. DeMatteo, M. D'Angelica, R. C. Kurtz, G. K. AbouAlfa, a S. Klimstra, M. A. Lowery, M. F. Brennan, D. G. Coit, D. L. Reidy, T. P. Kingham, and P. J. Allen, "A Single-Arm, Nonrandomized Phase II Trial of Neoadjuvant Gemcitabine and Oxaliplatin in Patients With Resectable Pancreas Adenocarcinoma," Annals of Surgery 260(1), 142-8 (2014).
136. R. M. Haralick, K. Shanmugam, and I. Dinstein, "Textural features for image classification," IEEE Transactions on Systems, Man, Cybernetics 3(6), 610-622 (1973).
137. X. Tang, "Texture information in run-length matrices," IEEE Transactions on Image Processing 7(11), 1602-1609 (1998).
138. T. Ojala, M. Pietikinen, and D. Harwood, "A comparative study of texture measures with classification based on feature distributions," Pattern Recognition 29, 51-59 (1996).
139. M. Pietikinen, A. Hadid, G. Zhao, and T. Ahonen, "Local binary patterns for still images," in Computer Vision Using Local Binary Patterns, Computational Imaging and Vision 40, 13-47, Springer London (2011).
140. S. Buczkowski, S. Kyriacos, F. Nekka, and L. Cartilier, "The modified boxcounting method: Analysis of some characteristic parameters," Pattern Recognition 31, 411-418 (1998).
141. J. Chakraborty, R. M. Rangayyan, S. Banik, S. Mukhopadhyay, and J. E. L. Desautels, "Statistical measures of orientation of texture for the detection of architectural distortion in prior mammograms of interval cancer," Journal of Electronic Imaging 1(3) (2012).
142. A. Midya and J. Chakraborty, "Classification of benign and malignant masses in mammograms using multi-resolution analysis of oriented patterns," in IEEE 12th International Symposium on Biomedical Imaging (ISBI), 2015, 411-414 (2015).
143. X. Yang, S. Tridandapani, J. J. Beitler, D. S. Yu, E. J. Yoshida, W. J. Curran, and T. Liu, "Ultrasound GLCM texture analysis of radiation-induced parotid-gland injury in head-and-neck cancer radiotherapy: An in vivo study of late toxicity," Medical physics 39(9), 5732-5739 (2012).
144. R. N. Khushaba, S. Kodagoa, S. Lal, and G. Dissanayake, "Measures of angular spread and entropy for the detection of architectural distortion in prior mammograms," International Journal of Computer assisted Radiology and Surgery 8(1), 121-134 (2013).
145. S. Banik, R. M. Rangayyan, and J. E. L. Desautels, "Detection of architectural distortion in prior mammograms," IEEE Transactions of Medical Imaging 30(2), 279-294 (2011).
146. T. Ahonen, J. Matas, C. He, and M. Pietikinen, "Rotation invariant image description with local binary pattern histogram fourier features," in Proceedings of 16th Scandinavian Conference on Image Analysis (SCIA 2009), 5575, 61-70 (2009).
147. O. S. Al-Kadi and D. Watson, "Texture analysis of aggressive and nonaggressive lung tumor CE CT images," IEEE Transactions on Biomedical Engineering 55(7), 1822-1830 (2008).
148. S. M. Prigarin, K. Sandau, M. Kazmierczak, and K. Hahn, "Estimation of fractal dimension: A survey with numerical experiments and software description," International Journal of Biomathematics and Biostatistics 2(1), 167-180 (2013).
149. A. F. Costa, G. H. Mamani, and A. J. M. Traina, "An efficient algorithm for fractal analysis of textures," in Proceedings of the 25th SIBGRAPI Conference on Graphics, Patterns and Images (SIBGRAPI 2012), 39-46 (2012).
150. R. N. Khushaba, S. Kodagoa, S. Lal, and G. Dissanayake, "Driver drowsiness classification using fuzzy wavelet packet based feature extraction algorithm," IEEE Transaction on Biomedical Engineering 58(1), 121-131 (2011).
151. R. N. K. A. Al-Ani, "A population based feature subset selection algorithm guided by fuzzy feature dependency," in Advanced Machine Learning Technologies and Applications, 322, 430-438 (2012).
152. H. Peng, F. Long, and C. Ding, "Feature selection based on mutual information: criteria of max-dependency, max-relevance, and min-redundancy," IEEE Transactions on Pattern Analysis and Machine Intelligence 27(8), 1226-1238 (2005).
153. M. Antonelli, P. Ducange, and F. Marcelloni, "Feature selection based on fuzzy mutual information," in Fuzzy Logic and Applications, F. Masulli, G. Pasi, and R. Yager, Eds., Lecture Notes in Computer Science 8256, 36-43, Springer International Publishing (2013).
154. R. O. Duda, P. E. Hart, and D. G. Stork, Pattern Classification, Wiley-Interscience, New York, N.Y., 2nd ed. (2001).
155. M. Spiteri, D. Windridge, S. Avula, R. Kumar, and E. Lewisa, "Pancreatic cancer early detection: expanding higher-risk group with clinical and metabolomics parameters," Journal of Medical Imaging 2(4), 044502-1-044502-9 (2015).

156. M. P. Callery, K. Chang, E. K. Fishman, M. S. Talamonti, L. T. William, and D. C. Linehan, "Pretreatment assessment of resectable and borderline resectable pancreatic cancer; expert consensus statement," Annals of Surgical *Oncology* 16(7), 1727-1733 (2009).

157. D'Angelica M I, Correa-Gallego C, Paty P B, Cercek A, Gewirtz A N, Chou J F, et al. Phase II trial of hepatic artery infusional and systemic chemotherapy for patients with unresectable hepatic metastases from colorectal cancer: conversion to resection and long-term outcomes. Arm Surg. 2015; 261(2):353-60.

158. Kemeny N, Jarnagin W, Paty P, Gönen M, Schwartz L, Morse M, et al. Phase I Trial of Systemic Oxaliplatin Combination Chemotherapy With Hepatic Arterial Infusion in Patients With Unresectable Liver Metastases From. Colorectal Cancer. J Clin Oncol. 2005 June; 23(22):4888-96.

What is claimed is:

1. A non-transitory computer-accessible medium having stored thereon computer-executable instructions for determining a pixel variation of at least one tissue in at least one image, wherein, when a computer arrangement executes the instructions, the computer arrangement is programmed and configured to perform procedures comprising:
   a) receiving first imaging information related to the at least one image;
   b) segmenting at least one region of interest from the at least one image;
   c) generating second imaging information by subtracting at least one structure from the at least one region of interest;
   d) determining the pixel variation based on the second imaging information using at least one gray-level co-occurrence matrix (GLCM);
   e) extracting at least one feature of the at least one tissue as further information based on the GLCM, wherein the GLCM includes at least four texture feature statistics;
   f) determining third imaging information related to at least one volume of the at least one region of interest based on the second information, wherein values of at least one pixel of the at least one volume are expressed in Hounsfield units (HU); and
   g) generating fourth imaging information by removing pixels from the third imaging information that have a HU value in a particular range.

2. The computer-accessible medium of claim 1, wherein the at least one tissue includes at least one of a liver or a pancreas.

3. The computer-accessible medium of claim 1, wherein the computer arrangement is further configured to determine at least one of (i) at least one treatment characteristic based on the pixel variation, or (ii) an image quality of the at least one image of the at least one tissue associated with the first imaging information based on the pixel variation.

4. The computer-accessible medium of claim 3, wherein the at least one treatment characteristic includes at least one of (i) a sufficiency of the at least one tissue, (ii) a response to chemotherapy by the at least one tissue, (iii) a recurrence of cancer in the at least one tissue, or (iv) a measure of a genomic expression of the at least one tissue.

5. The computer-accessible medium of claim 1, wherein the first imaging information includes at least one computed tomography (CT) image of the at least one tissue.

6. The computer-accessible medium of claim 5, wherein the computer arrangement is further configured to pre-process the at least one CT image to determine the at least one region of interest.

7. The computer-accessible medium of claim 1, wherein the at least one feature extracted by the computer arrangement includes at least one of (i) an entropy of the at least one tissue, or (ii) at least one quantitative predictor of an outcome of a cancer treatment.

8. The computer-accessible medium of claim 7, wherein the at least one quantitative predictor includes at least one of a survival rate of a patient to whom the at least one tissue belongs or complications associated with the patient to whom the at least one tissue belongs.

9. The computer-accessible medium of claim 1, wherein the at least one region of interest includes at least one of a tumor or parenchyma.

10. The computer-accessible medium of claim 1, wherein the at least one structure includes at least one of at least one bile duct or at least one vessel.

11. The computer-accessible medium of claim 1, wherein the particular range is from about 0 HU to about 300 HU.

12. The computer-accessible medium of claim 1, wherein the computer arrangement is further configured to determine the pixel variation based on the third imaging information.

13. The computer-accessible medium of claim 1, wherein the computer arrangement is further configured to scale the third imaging information.

14. A computer-accessible medium having stored thereon computer-executable instructions for determining a pixel variation of at least one tissue in at least one image, wherein, when a computer arrangement executes the instructions, the computer arrangement is programmed and configured to perform procedures comprising:
   a) receiving first imaging information related to the at least one image;
   b) segmenting at least one region of interest from the at least one image;
   c) generating second imaging information by subtracting at least one structure from the at least one region of interest;
   d) determining the pixel variation based on the second imaging information;
   e) determining at least one of (i) at least one treatment characteristic based on the pixel variation, (ii) an image quality of the at least one image of the at least one tissue associated with the first imaging information based on the pixel variation, (iii) the pixel variation using at least one gray-level co-occurrence matrix (GLCM), or (iv) third imaging information related to at least one volume of the at least one region of interest based on the second information, and wherein values of pixel of the at least one volume are expressed in Hounsfield units (HU);
   f) extracting at least one feature of the at least one tissue as further information based on the GLCM, wherein the GLCM includes at least four texture feature statistics; and
   g) generating fourth imaging information by removing pixels from the third imaging information that have a HU value in a particular range.

15. The computer-accessible medium of claim 1, wherein the at least four texture feature statistics include (i) a contrast, (ii) a correlation, (iii) an energy, and (iv) a homogeneity.

16. The computer-accessible medium of claim 15, wherein the computer arrangement is configured to determine each of the texture feature statistics in at least four directions.

17. The computer-accessible medium of claim 16, wherein the at least four directions include, substantially, (i) 0°, (ii) 45°, (iii) 90°, and (iv) 135°.

18. A method for determining a pixel variation of at least one tissue in at least one image, comprising:
   a) receiving first imaging information related to the at least one image;
   b) segmenting at least one region of interest from the at least one image;
   c) generating second imaging information by subtracting at least one structure from the at least one region of interest;
   d) using a computer hardware arrangement, determining the pixel variation based on the second imaging information using at least one gray-level co-occurrence matrix (GLCM);
   e) extracting at least one feature of the at least one tissue as further information based on the GLCM, wherein the GLCM includes at least four texture feature statistics;
   f) determining third imaging information related to at least one volume of the at least one region of interest based on the second information, wherein values of at least one pixel of the at least one volume are expressed in Hounsfield units (HU); and
   g) using the computer hardware arrangement, generating fourth imaging information by removing pixels from the third imaging information that have a HU value in a particular range.

19. A system for determining a pixel variation of at least one tissue in at least one image, comprising:
   a computer hardware arrangement configured to:
      a) receive first imaging information related to the at least one image;
      b) segmenting at least one region of interest from the at least one image;
      c) generate second imaging information by subtracting at least one structure from the at least one region of interest;
      d) determine the pixel variation based on the second imaging information_using at least one gray-level co-occurrence matrix (GLCM);
      e) extract at least one feature of the at least one tissue as further information based on the GLCM, wherein the GLCM includes at least four texture feature statistics;
      f) determine third imaging information related to at least one volume of the at least one region of interest based on the second information, wherein values of at least one pixel of the at least one volume are expressed in Hounsfield units (HU); and
      g) generate fourth imaging information by removing pixels from the third imaging information that have a HU value in a particular range.

20. A non-transitory computer-accessible medium having stored thereon computer-executable instructions for determining a sufficiency of at least one tissue, wherein, when a computer arrangement executes the instructions, the computer arrangement is programmed and configured to perform procedures comprising:
   a computer hardware arrangement configured to:
      receive information related to the at least one tissue;
      perform a texture analysis using at least one gray-level co-occurrence matrix (GLCM), wherein the GLCM includes at least four texture feature statistics;
      extract at least one feature of the at least one tissue based on the at least one GLCM;
      determine the sufficiency based on the at least one feature;
      determine first imaging information related to at least one volume of the at least one region of interest, wherein values of at least one pixel of the at least one volume are expressed in Hounsfield units (HU); and
      generate second imaging information by removing pixels from the first imaging information that have a HU value in a particular range.

21. The computer-accessible medium of claim 20, wherein the at least one tissue includes at least one of a liver or a pancreas.

22. The computer-accessible medium of claim 20, wherein information includes at least one computed tomography (CT) scan of the at least one tissue.

23. The computer-accessible medium of claim 22, wherein the computer arrangement is further configured to control the at least one CT scan of the at least one tissue using a CT scanning arrangement.

24. The computer-accessible medium of claim 20, wherein the at least one feature includes at least one of a contrast of an image of the at least one tissue or entropy of the image of the at least one tissue.

25. A method for determining a sufficiency of at least one tissue, comprising:
   a) receive information related to the at least one tissue;
   b) perform a texture analysis using at least one gray-level co-occurrence matrix (GLCM), wherein the GLCM includes at least four texture feature statistics;
   c) extract at least one feature of the at least one tissue based on the at least one GLCM;
   d) using a specifically programmed and configured computer hardware arrangement, determining the sufficiency based on the at least one feature;
   e) determine first imaging information related to at least one volume of the at least one region of interest, wherein values of at least one pixel of the at least one volume are expressed in Hounsfield units (HU); and
   f) using the computer hardware arrangement, generate second imaging information by removing pixels from the first imaging information that have a HU value in a particular range.

26. A system for determining a sufficiency of at least one tissue, comprising:
   a computer hardware arrangement configured to:
      receive information related to the at least one tissue;
      perform a texture analysis using at least one gray-level co-occurrence matrix (GLCM), wherein the GLCM includes at least four texture feature statistics;
      extract at least one feature of the at least one tissue based on the at least one GLCM;
      determine the sufficiency based on the at least one feature;
      determine first imaging information related to at least one volume of the at least one region of interest, wherein values of at least one pixel of the at least one volume are expressed in Hounsfield units (HU); and
      generate second imaging information by removing pixels from the first imaging information that have a HU value in a particular range.

* * * * *